US006586621B2

(12) United States Patent
Leiber et al.

(10) Patent No.: US 6,586,621 B2
(45) Date of Patent: Jul. 1, 2003

(54) USE OF A SUPPLEMENTAL PROMOTER IN CONJUNCTION WITH A CARBON-SUPPORTED, NOBLE-METAL CONTAINING CATALYST IN LIQUID PHASE OXIDATION REACTIONS

(75) Inventors: Mark A. Leiber, St. Peters, MO (US); Jerry R. Ebner, St. Peters, MO (US); Kam-To Wan, Manchester, MO (US); Anthony Woods, Ossett (GB); Peter Rogers, Des Peres, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/746,186

(22) Filed: Dec. 21, 2000

(65) Prior Publication Data

US 2002/0016503 A1 Feb. 7, 2002

Related U.S. Application Data

(60) Provisional application No. 60/171,313, filed on Dec. 21, 1999.

(51) Int. Cl.$^7$ ............................... C07F 9/22; C07F 9/28
(52) U.S. Cl. ......................................................... 562/17
(58) Field of Search .................. 562/8, 16, 17

(56) References Cited

U.S. PATENT DOCUMENTS

| | | | |
|---|---|---|---|
| 3,799,758 A | | 3/1974 | Franz |
| 3,950,402 A | | 4/1976 | Franz |
| 3,969,398 A | | 7/1976 | Hershman |
| 4,351,962 A | | 9/1982 | Gradeff et al. |
| 4,582,650 A | | 4/1986 | Felthouse |
| 4,624,937 A | | 11/1986 | Chou |
| 4,696,772 A | | 9/1987 | Chou |
| 5,091,561 A | * | 2/1992 | Riley et al. ............. 562/17 |
| 5,179,228 A | | 1/1993 | Martin Ramon et al. |
| 5,292,936 A | * | 3/1994 | Franczyk ............. 562/526 |
| 5,500,485 A | | 3/1996 | Hodgkinson |
| 5,606,107 A | | 2/1997 | Smith |
| 5,739,390 A | * | 4/1998 | Franczyk ............. 562/526 |

FOREIGN PATENT DOCUMENTS

| | | |
|---|---|---|
| DE | 196 00 741 A1 | 7/1996 |
| EP | 1 067 108 A2 | 1/2001 |
| GB | 1 601 715 | 11/1981 |
| WO | WO 99/03402 | 1/1999 |
| WO | WO 99/43430 | 9/1999 |
| WO | WO 00/01707 * | 1/2000 |
| WO | WO 00/09517 | 2/2000 |

OTHER PUBLICATIONS

US 6,337,298, 1/2002, Ebner et al. (withdrawn)*
D.S. Cameron, S.J. Cooper, I.L. Dodgson, B. Harrison and J.W. Jenkins, Carbons As Supports For Precious Metal Catalysts, *Catalysis Today*, 1990, 113–137, Elsevier Science Publishers B.V., Amsterdam—Printed in the Netherlands.
Vladimir Ponec and Geoffrey C. Bond, Catalysis by Metals and Alloys, pp. 320–356, vol. 95, Elsevier, New York, 1995.

* cited by examiner

Primary Examiner—Jean F. Vollano
(74) Attorney, Agent, or Firm—Senniger, Powers, Leavitt & Roedel; Joseph A. Schaper

(57) ABSTRACT

This invention relates to the use of a supplemental promoter in conjunction with a noble-metal-containing catalyst comprising a carbon support in catalyzing liquid phase oxidation reactions, a process for making of an improved catalyst comprising such a supplemental promoter, and an improved catalyst comprising such a supplemental promoter.

In a particularly preferred embodiment, a supplemental promoter (most preferably bismuth or tellurium) is used in conjunction with a noble-metal-containing catalyst comprising a carbon support in a liquid phase oxidation process wherein N-(phosphonomethyl) iminodiacetic acid (i.e., "PMIDA") or a salt thereof is oxidized to form N-(phosphonomethyl) glycine (i.e., "glyphosate") or a salt thereof. The benefits of such a process include increased oxidation of the formaldehyde and formic acid by-products, and, consequently, decreased final concentrations of those by-products as well as other undesirable by-products, most notably N-methyl-N-(phosphonomethyl) glycine (i.e., "NMG").

27 Claims, 16 Drawing Sheets

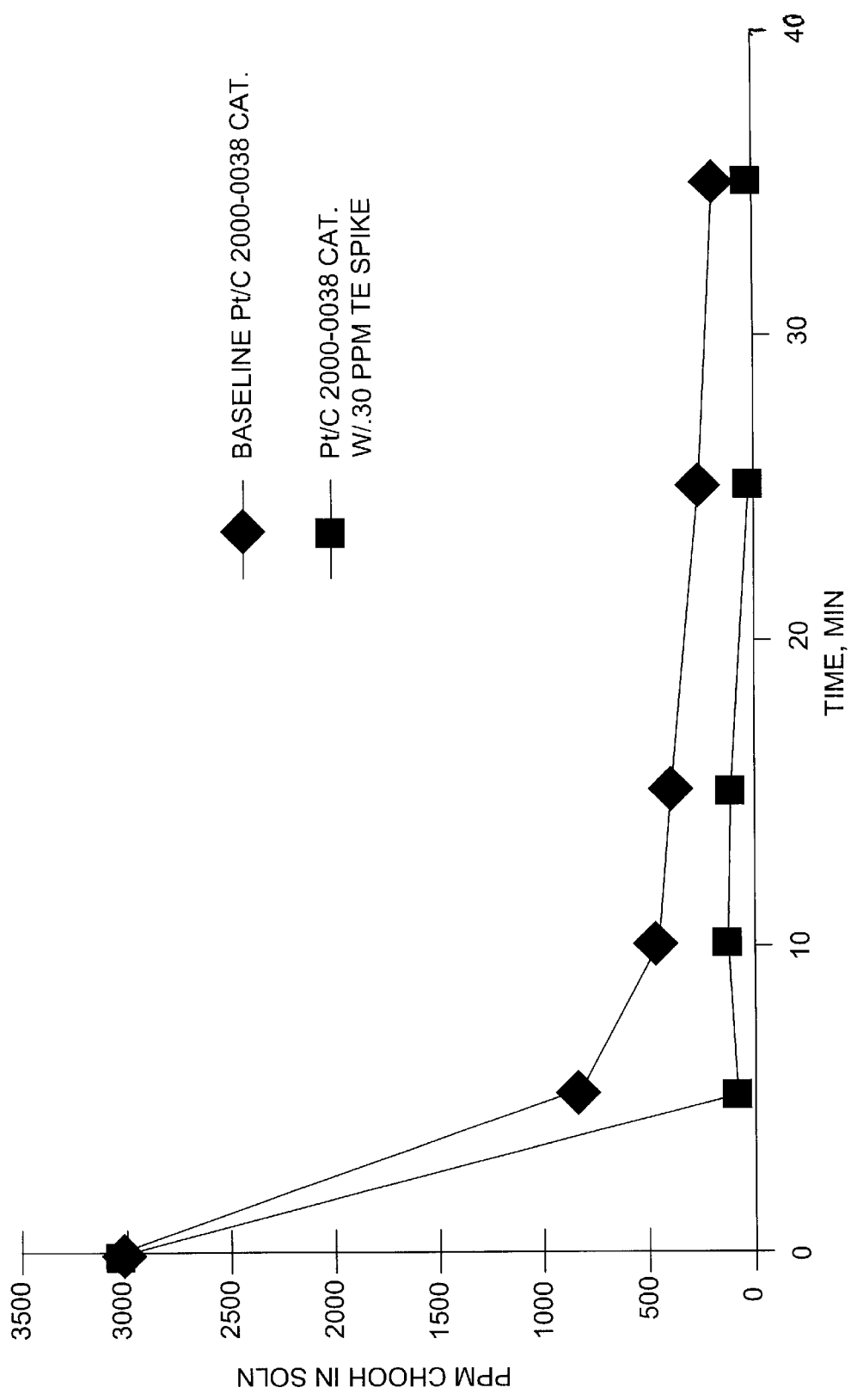

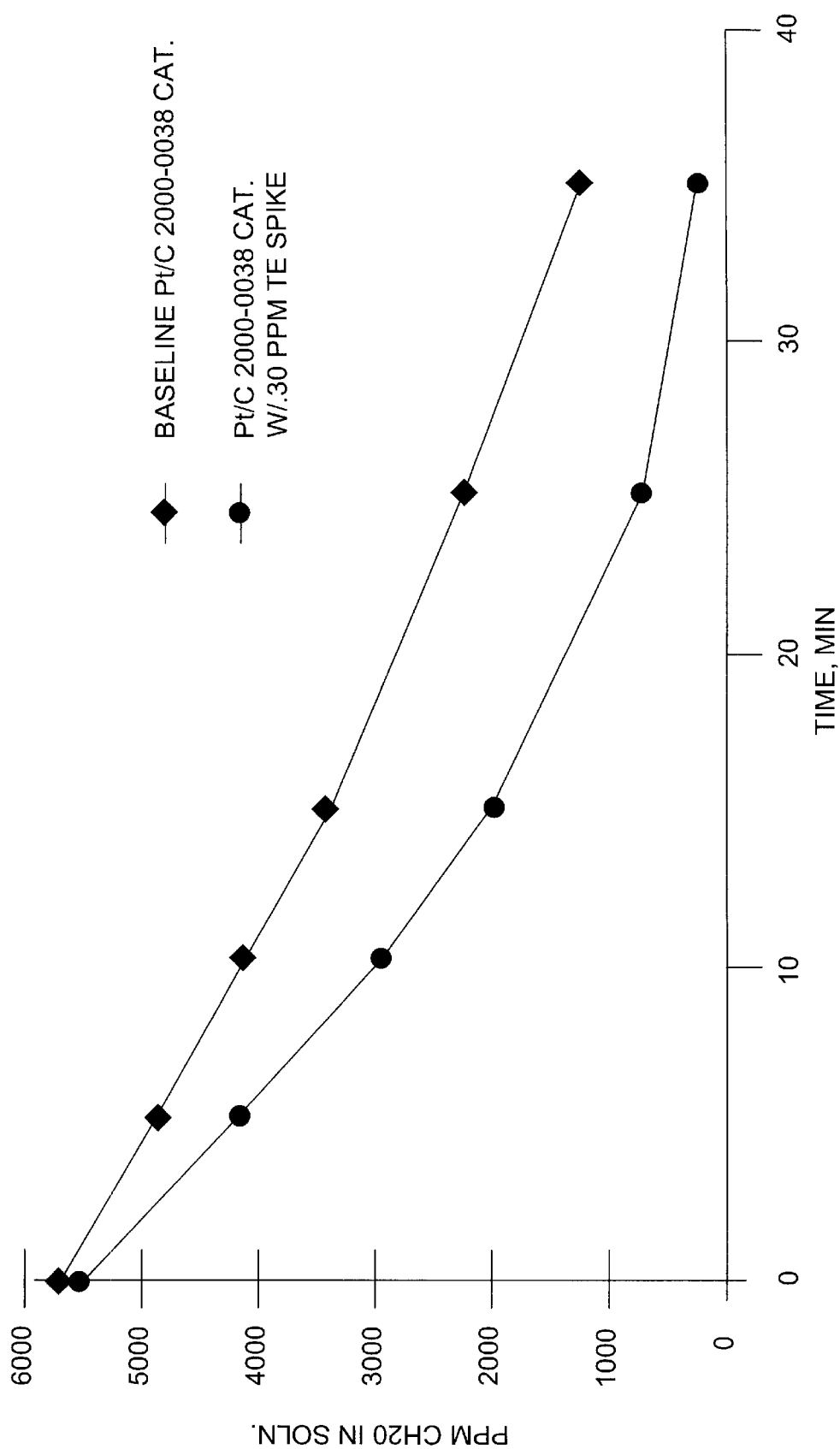

USE OF A SUPPLEMENTAL PROMOTER IN CONJUNCTION WITH A CARBON-SUPPORTED, NOBLE-METAL CONTAINING CATALYST IN LIQUID PHASE OXIDATION REACTIONS

CROSS-REFERENCE TO RELATED APPLICATIONS

This application claims priority from U.S. provisional patent application Ser. No. 60/171,313 filed Dec. 21, 1999, which is hereby incorporated by reference in its entirety.

FIELD OF THE INVENTION

This invention generally relates to liquid phase oxidation processes using a carbon-supported, noble-metal-containing catalyst (particularly a deeply reduced catalyst) in conjunction with a supplemental promoter (e.g., bismuth or tellurium). In an especially preferred embodiment, this invention relates to such a process wherein N-(phosphonomethyl)iminodiacetic acid ("PMIDA") or a salt thereof is oxidized to form N-(phosphonomethyl)glycine (also known in the agricultural chemical industry as "glyphosate") or a salt thereof. This invention also generally relates to enhancing the activity, selectivity, and/or stability of a carbon-supported, noble-metal-containing catalyst (particularly a deeply reduced catalyst) using a supplemental promoter.

BACKGROUND OF THE INVENTION

N-(phosphonomethyl)glycine is described in Franz, U.S. Pat. No. 3,799,758. N-(phosphonomethyl)glycine and its salts are conveniently applied as a post-emergent herbicide in an aqueous formulation. Glyphosate is a highly effective and commercially important broad-spectrum herbicide useful in killing or controlling the growth of a wide variety of plants, including germinating seeds, emerging seedlings, maturing and established woody and herbaceous vegetation, and aquatic plants.

Various methods for making N-(phosphonomethyl) glycine are known in the art. Franz (U.S. Pat. No. 3,950,402) discloses that N-(phosphonomethyl)glycine may be prepared by the liquid phase oxidative cleavage of PMIDA with oxygen in the presence of a catalyst comprising a noble metal deposited on the surface of an activated carbon support:

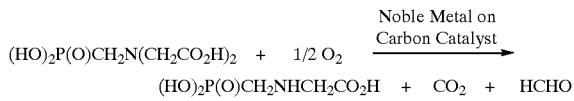

$(HO)_2P(O)CH_2N(CH_2CO_2H)_2 + 1/2 O_2 \xrightarrow{\text{Noble Metal on Carbon Catalyst}}$
$(HO)_2P(O)CH_2NHCH_2CO_2H + CO_2 + HCHO$ Other by-products also typically form, such as formic acid ($HCO_2H$), which is formed by the oxidation of the formaldehyde by-product; and aminomethylphosphonic acid ("AMPA"), which is formed by the oxidation of N-(phosphonomethyl)glycine. Even though the Franz method produces an acceptable yield and purity of N-(phosphonomethyl)glycine, high losses of the costly noble metal into the reaction solution (i.e., "leaching") result because, under the oxidation conditions of the reaction, some of the noble metal is oxidized into a more soluble form, and both PMIDA and N-(phosphonomethyl)glycine act as ligands which solubilize the noble metal.

In U.S. Pat. No. 3,969,398, Hershman discloses that activated carbon alone, without the presence of a noble metal, may be used to effect the oxidative cleavage of PMIDA to form N-(phosphonomethyl)glycine. In U.S. Pat. No. 4,624,937, Chou further discloses that the activity of the carbon catalyst disclosed by Hershman may be increased by removing the oxides from the surface of the carbon catalyst before using it in the oxidation reaction. See also, U.S. Pat. No. 4,696,772, which provides a separate discussion by Chou regarding increasing the activity of the carbon catalyst by removing oxides from the surface of the carbon catalyst. Although these processes obviously do not suffer from noble metal leaching, they do tend to produce greater concentrations of formic acid and formaldehyde by-product when used to effect the oxidative cleavage of N-phosphonomethyliminodiacetic acid. These byproducts are particularly undesirable because they react with N-(phosphonomethyl)glycine to produce unwanted by-products (mainly N-methyl-N-(phosphonomethyl) glycine, sometimes referred to as "NMG") which reduce the N-(phosphonomethyl)glycine yield. In addition, the formaldehyde by-product itself is undesirable because of its potential toxicity. See Smith, U.S. Pat. No. 5,606,107.

Optimally, therefore, it has been suggested that the formic acid and formaldehyde be simultaneously oxidized to carbon dioxide and water as the PMIDA is oxidized to N-(phosphonomethyl)glycine in a single reactor, thus giving the following net reaction:

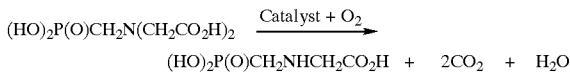

$(HO)_2P(O)CH_2N(CH_2CO_2H)_2 \xrightarrow{\text{Catalyst} + O_2}$
$(HO)_2P(O)CH_2NHCH_2CO_2H + 2CO_2 + H_2O$ As the above references suggest, such a process requires the presence of both carbon (which primarily effects the oxidation of PMIDA to form N-(phosphonomethyl)glycine and formaldehyde) and a noble metal (which primarily effects the oxidation of formaldehyde and formic acid to form carbon dioxide and water). Previous attempts to develop a stable catalyst for such an oxidation process, however, have not been entirely satisfactory.

Like Franz, Ramon et al. (U.S. Pat. No. 5,179,228) disclose using a noble metal deposited on the surface of a carbon support. To reduce the problem of leaching (which Ramon et al. report to be as great as 30% noble metal loss per cycle), however, Ramon et al. disclose flushing the reaction mixture with nitrogen under pressure after the oxidation reaction is completed to cause re-deposition of the noble metal onto the surface of the carbon support. According to Ramon et al., nitrogen flushing reduces the noble metal loss to less than 1%. Still, the amount of noble metal loss incurred with this method is unacceptable. In addition, re-depositing the noble metal can lead to loss of noble metal surface area which, in turn, decreases the activity of the catalyst.

Using a different approach, Felthouse (U.S. Pat. No. 4,582,650) discloses using two catalysts: (i) an activated carbon to effect the oxidation of PMIDA into N-(phosphonomethyl)glycine, and (ii) a co-catalyst to concurrently effect the oxidation of formaldehyde into carbon dioxide and water. The co-catalyst consists of an aluminosilicate support having a noble metal located within its pores. The pores are sized to exclude N-(phosphonomethyl) glycine and thereby prevent the noble metal of the co-catalyst from being poisoned by N-(phosphonomethyl) glycine. According to Felthouse, use of these two catalysts together allows for the simultaneous oxidation of PMIDA to N-(phosphonomethyl)glycine and of formaldehyde to carbon dioxide and water. This approach, however, suffers from several disadvantages: (1) it is difficult to recover the costly noble metal from the aluminosilicate support for re-use; (2) it is difficult to design the two catalysts so that the rates between them are matched; and (3) the carbon support, which has no noble metal deposited on its surface, tends to deactivate at a rate which can exceed 10% per cycle.

In PCT/US99/03402, Ebner et al. disclose a reaction process for making N-(phosphonomethyl)glycine compounds from PMIDA compounds using a deeply reduced, carbon-supported, noble metal catalyst which exhibits improved resistance to noble metal leaching and increased destruction of undesirable byproducts (e.g., formaldehyde). Still, this reaction process typically does not eliminate all the formaldehyde and formic acid byproduct, and, consequently, also does not eliminate all the N-methyl-N-(phosphonomethyl)glycine byproduct.

Thus, a need continues to exist for an improved reaction process for oxidizing PMIDA to N-(phosphonomethyl) glycine using a catalyst which exhibits resistance to noble metal leaching and increased oxidation of formic acid and formaldehyde into carbon dioxide and water (i.e., increased formic acid and formaldehyde activity).

SUMMARY OF THE INVENTION

This invention provides, in part, for an improved process for oxidizing PMIDA, salts of PMIDA, and esters of PMIDA to form N-(phosphonomethyl)glycine, salts of N-(phosphonomethyl)glycine, and esters of N-(phosphonomethyl)glycine, particularly such a process which uses a catalyst (or catalyst system) that (a) exhibits resistance to noble metal leaching, and (b) exhibits increased oxidation of formic acid and/or formaldehyde, and consequent decreased formation of NMG; an improved process for oxidizing a substrate in general wherein the activity, selectivity, and/or stability of a carbon-supported, noble-metal-containing catalyst used to catalyze the oxidation is enhanced by merely mixing the catalyst with a supplemental promoter (rather than using a catalyst which already contains the promoter, and, consequently, is more costly to manufacture); an improved process for making an oxidation catalyst system (particularly an oxidation catalyst system for oxidizing PMIDA compounds) having enhanced activity, selectivity, and/or stability; and an oxidation catalyst system (particularly an oxidation catalyst system for oxidizing PMIDA compounds) having enhanced activity, selectivity, and/or stability.

Briefly, therefore, the present invention is directed to a process for oxidizing formic acid or formaldehyde in the presence of a catalyst and a supplemental promoter. Here, the catalyst comprises a noble metal and a carbon support; and the mass ratio of the supplemental promoter to the catalyst is at least about 1:15,000.

The present invention is also directed to a process for oxidizing a substrate in general using a catalyst comprising a carbon support and a noble metal. In this embodiment, the process comprises contacting the substrate with oxygen in the presence of the catalyst and a supplemental promoter. Here, the mass ratio of the supplemental promoter to the catalyst is at least about 1:15,000. And, before the catalyst is used in the oxidation of the substrate, the catalyst:

A. comprises a non-graphitic carbon support having a noble metal at a surface of the non-graphitic carbon support; and
   is identifiable as yielding no greater than about 0.7 mmole of carbon monoxide per gram of catalyst when a dry sample of the catalyst in a helium atmosphere is heated from about 20° to about 900° C. at a rate of about 10° C. per minute, and then at about 900° C. for about 30 minutes; or B. comprises a non-graphitic carbon support having a noble metal and a catalyst-surface promoter at a surface of the non-graphitic carbon support; and
   is identifiable as yielding no greater than about 0.7 mmole of carbon monoxide per gram of catalyst when a dry sample of the catalyst, after being heated at a temperature of about 500° C. for about 1 hour in a hydrogen atmosphere and before being exposed to an oxidant following the heating in the hydrogen atmosphere, is heated in a helium atmosphere from about 20° to about 900° C. at a rate of about 10° C. per minute, and then at about 900° C. for about 30 minutes; or C. comprises a non-graphitic carbon support having a noble metal, carbon, and oxygen at a surface of the non-graphitic carbon support, the ratio of carbon atoms to oxygen atoms at the surface being at least about 30:1, as measured by x-ray photoelectron spectroscopy; or D. comprises a non-graphitic carbon support having a noble metal, a catalyst-surface promoter, carbon, and oxygen at a surface of the non-graphitic carbon support; and
   is identifiable as having a ratio of carbon atoms to oxygen atoms at the surface which is at least about 30:1, as measured by x-ray photoelectron spectroscopy after the catalyst is heated at a temperature of about 500° C. for about 1 hour in a hydrogen atmosphere and before the catalyst is exposed to an oxidant following the heating in the hydrogen atmosphere; or E. comprises a non-graphitic carbon support having (i) a noble metal at a surface of the non-graphitic carbon support; and (ii) a surface layer having a thickness of about 50 Å as measured inwardly from the surface and comprising oxygen and carbon, the ratio of carbon atoms to oxygen atoms in the surface layer being at least about 30:1, as measured by x-ray photoelectron spectroscopy; or F. comprises a non-graphitic carbon support having: (a) a noble metal and a catalyst-surface promoter at a surface of the non-graphitic carbon support; and (b) a surface layer having a thickness of about 50 Å as measured inwardly from the surface and comprising carbon and oxygen; and
   is identifiable as having a ratio of carbon atoms to oxygen atoms in the surface layer of at least about 30:1, as measured by x-ray photoelectron spectroscopy after the catalyst is heated at a temperature of about 500° C. for about 1 hour in a hydrogen atmosphere and before the catalyst is exposed to an oxidant following the heating in the hydrogen atmosphere;

G. is formed by a process comprising depositing a noble metal at a surface of a non-graphitic carbon support, and then heating the surface at a temperature of at least about 400° C., wherein, before the noble metal deposition, the ratio of carbon atoms to oxygen atoms at the surface of the non-graphitic carbon support is at least about 20:1, as measured by x-ray photoelectron spectroscopy; or H. is formed by a process comprising depositing a noble metal at a surface of a carbon support, and then exposing the surface to a reducing environment, wherein, before the noble metal deposition, the carbon support has carbon atoms and oxygen atoms at the surface of the carbon support in amounts such that the ratio of carbon atoms to oxygen atoms at the surface is at least about 20:1, as measured by x-ray photoelectron spectroscopy; or I. is formed by a process comprising depositing a noble metal at a surface of a non-graphitic carbon support, and then heating the surface at a temperature greater than about 500° C.

The present invention is also directed to a process for making an oxidation catalyst system.

In one embodiment directed to a process for making an oxidation catalyst system, the process comprises mixing a noble-metal-containing catalyst with a supplemental promoter in the presence of formic acid or formaldehyde. Here, the noble-metal-containing catalyst comprises a noble metal and a carbon support; and the mass ratio of the supplemental promoter to the noble-metal-containing catalyst is at least about 1:15,000.

In another embodiment directed to a process for making an oxidation catalyst system, the catalyst system is prepared using a carbon support having carbon atoms and oxygen atoms at a surface of the non-graphitic carbon support. In this process, a noble metal is deposited at the surface of the carbon support to form a noble-metal-containing catalyst. Oxygen-containing functional groups are subsequently removed from the surface of the noble-metal-containing catalyst to form a noble-metal-containing catalyst comprising a deoxygenated surface. This removal of oxygen-containing functional groups comprises:

(i) heating the surface of the noble-metal-containing catalyst at a temperature of greater than about 500° C.; or (ii) heating the surface of the noble-metal-containing catalyst at a temperature of at least about 400° C., wherein, before the noble metal deposition, the ratio of carbon atoms to oxygen atoms at the surface of the non-graphitic carbon support is at least about 20:1, as measured by x-ray photoelectron spectroscopy; or (iii) exposing the surface of the noble-metal-containing catalyst to a reducing environment, wherein, before the noble metal deposition, the ratio of carbon atoms to oxygen atoms at the surface of the non-graphitic carbon support is at least about 20:1, as measured by x-ray photoelectron spectroscopy; or (iv) exposing the surface of the noble-metal-containing catalyst to a reducing environment so that the ratio of carbon atoms to oxygen atoms at the deoxygenated surface of the noble-metal-containing catalyst comprising the deoxygenated surface is at least about 30:1, as measured by x-ray photoelectron spectroscopy; or (v) exposing the surface of the noble-metal-containing catalyst to a reducing environment so that no greater than about 0.7 mmole of carbon monoxide per gram of the noble-metal-containing catalyst comprising the deoxygenated surface desorb from the deoxygenated surface when a dry sample of the noble-metal-containing catalyst comprising the deoxygenated surface is heated in a helium atmosphere from about 20° to about 900° C. at a rate of about 10° C. per minute, and then at about 900° C. for about 30 minutes.

After removing oxygen-containing functional groups from the surface of the noble-metal-containing catalyst, the noble-metal-containing catalyst is mixed with a supplemental promoter. Here, the mass ratio of the supplemental promoter to the noble-metal-containing catalyst is at least about 1:15,000.

This invention is also directed to an oxidation catalyst system.

In one embodiment directed to an oxidation catalyst system, the oxidation catalyst system is prepared by a process comprising mixing a noble-metal-containing catalyst with a supplemental promoter in the presence of formic acid or formaldehyde. Here, the noble-metal-containing catalyst comprises a noble metal and a carbon support; and the mass ratio of the supplemental promoter to the noble-metal-containing catalyst is at least about 1:15,000.

In another embodiment directed to an oxidation catalyst system, the oxidation catalyst system is prepared using a carbon support. When preparing this catalyst system, a noble metal is deposited onto a surface of the carbon support to form a noble-metal-containing catalyst. Oxygen-containing functional groups are subsequently removed from the surface of the noble-metal-containing catalyst to form a noble-metal-containing catalyst comprising a deoxygenated surface. This removal of oxygen-containing functional groups comprises:

(i) heating the surface of the noble-metal-containing catalyst at a temperature of greater than about 500° C.; or (ii) heating the surface of the noble-metal-containing catalyst at a temperature of at least about 400° C., wherein, before the noble metal deposition, the non-graphitic carbon support has carbon atoms and oxygen atoms at the surface in amounts such that the ratio of carbon atoms to oxygen atoms at the surface is at least about 20:1, as measured by x-ray photoelectron spectroscopy; or (iii) exposing the surface of the noble-metal-containing catalyst to a reducing environment, wherein, before the noble metal deposition, the non-graphitic carbon support has carbon atoms and oxygen atoms at the surface in amounts such that the ratio of carbon atoms to oxygen atoms at the surface is at least about 20:1, as measured by x-ray photoelectron spectroscopy; or (iv) exposing the surface of the noble-metal-containing catalyst to a reducing environment so that the ratio of carbon atoms to oxygen atoms at the deoxygenated surface of the noble-metal-containing catalyst comprising the deoxygenated surface is at least about 30:1, as measured by x-ray photoelectron spectroscopy; or (v) exposing the surface of the noble-metal-containing catalyst to a reducing environment so that no greater than about 0.7 mmole of carbon monoxide per gram of the noble-metal-containing catalyst comprising the deoxygenated carbon support surface desorb from the deoxygenated surface when a dry sample of the noble-metal-containing catalyst comprising the deoxygenated surface is heated in a helium atmosphere from about 20° to about 900° C. at a rate of about 10° C. per minute, and then at about 900° C. for about 30 minutes.

After oxygen-containing functional groups have been removed from the surface of the noble-metal-containing catalyst, the noble-metal-containing catalyst is mixed with a supplemental promoter. Here, the mass ratio of the supplemental promoter to the noble-metal-containing catalyst is at least about 1:15,000.

This invention also is directed to a general process for making N-(phosphonomethyl)glycine, a salt of N-(phosphonomethyl)glycine, or an ester of N-(phosphonomethyl)glycine. This process comprises oxidizing N-(phosphonomethyl)iminodiacetic acid, a salt of N-(phosphonomethyl)iminodiacetic acid, or an ester of N-(phosphonomethyl)iminodiacetic acid in the presence of an oxidation catalyst. Before the oxidation, this oxidation catalyst:

A. comprises a carbon support having a noble metal at a surface of the carbon support; and
   is identifiable as yielding no greater than about 1.2 mmole of carbon monoxide per gram of catalyst when a dry sample of the catalyst in a helium atmosphere is heated from about 20° to about 900° C. at a rate of about 10° C. per minute, and then at about 900° C. for about 30 minutes; or
B. comprises a carbon support having a noble metal, carbon, and oxygen at a surface of the carbon support, the ratio of carbon atoms to oxygen atoms at the surface being at least about 20:1, as measured by x-ray photoelectron spectroscopy; or
C. comprises a carbon support comprising: (a) a noble metal at a surface of the carbon support; and (b) a surface layer having a thickness of about 50 Å as measured inwardly from the surface and comprising carbon and oxygen, the ratio of carbon atoms to oxygen atoms in the surface layer being at least about 20:1, as measured by x-ray photoelectron spectroscopy; or
D. is formed by a process comprising depositing a noble metal at a surface of a carbon support, and then heating the surface at a temperature of at least about 400° C.; or
E. is formed by a process comprising:
depositing a noble metal at a surface of a carbon support, and then exposing the surface to a reducing environment, wherein, before the noble metal deposition, the carbon support has carbon atoms and oxygen atoms at the surface in amounts such that the ratio of carbon atoms to oxygen atoms at the surface is at least about 20:1, as measured by x-ray photoelectron spectroscopy; or
F. comprises a carbon support having a noble metal, a promoter, carbon, and oxygen at a surface of the carbon support; or
G. comprises a carbon support having: (a) a noble metal and a promoter at a surface of the carbon support; and (b) a surface layer having a thickness of about 50 Å as measured inwardly from the surface and comprising carbon and oxygen, the catalyst being identifiable as having a ratio of carbon atoms to oxygen atoms in the surface layer which is at least about 20:1, as measured by x-ray photoelectron spectroscopy after the catalyst is heated at a temperature of about 500° C. for about 1 hour in a hydrogen atmosphere and before the catalyst is exposed to an oxidant following the heating in the hydrogen atmosphere.

Other features of this invention will be in part apparent and in part pointed out hereinafter.

BRIEF DESCRIPTION OF THE DRAWINGS

FIG. 16 shows the effect of a supplemental promoter in oxidizing an aqueous stream of formic acid and formaldehyde by a comparison of formic acid oxidation activity when tellurium is used as a supplemental promoter.

FIG. 17 shows the effect of a supplemental promoter in oxidizing an aqueous stream of formic acid and formaldehyde by a comparison of formaldehyde oxidation activity when tellurium is used as a supplemental promoter.

DETAILED DESCRIPTION OF THE PREFERRED EMBODIMENTS

A. The Oxidation Catalyst

Figure 1:
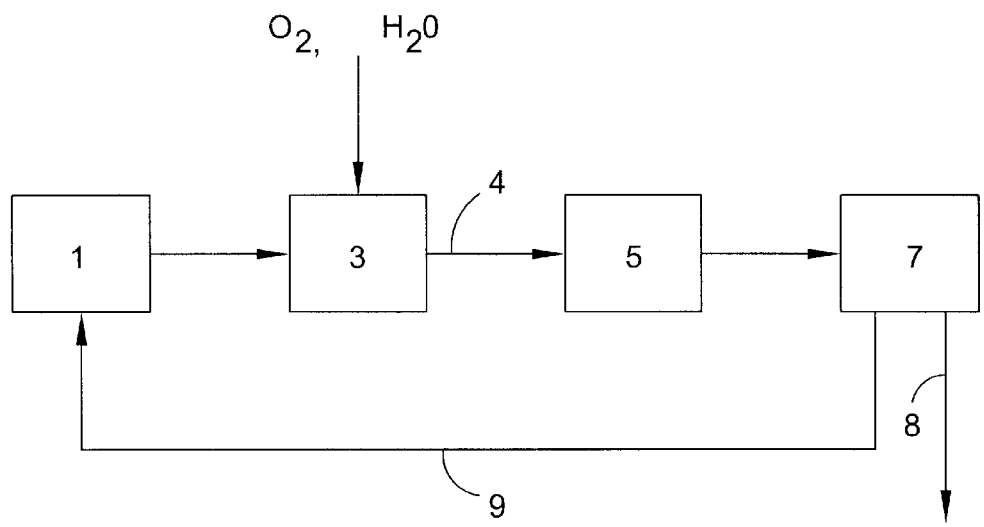
FIG. 1 shows one example of a batch-reaction embodiment that may be used in accordance with this invention.

The catalyst used in the present invention may be used to catalyze liquid phase (i.e., in an aqueous solution or an organic solvent) oxidation reactions, especially in acidic oxidative environments and in the presence of solvents, reactants, intermediates, or products which solubilize noble metals. The catalyst exhibits resistance to noble metal leaching from the catalyst surface under these conditions.

The noble metal component of the catalyst serves various functions. For example, depositing a noble metal onto the surface of a catalyst consisting of a carbon support alone tends to reduce the rate of deactivation of the catalyst. To illustrate, when N-(phosphonomethyl)glycine is prepared by the liquid phase oxidative cleavage of PMIDA with oxygen in the presence of a catalyst consisting of an activated carbon support without a noble metal, the activated carbon is found to deactivate as much as 10% per cycle or more. Without being bound by any particular theory, it is believed that the deactivation of the activated carbon arises because the surface of the carbon support oxidizes under the reaction conditions. See Chou, U.S. Pat. No. 4,624,937. See also, Chou, U.S. Pat. No. 4,696,772, which provides a separate discussion related to deactivation of activated carbon by oxidation of the surface of the carbon. In the presence of the noble metal, however, the rate of deactivation of the activated carbon is diminished. It is believed that the noble metal can react with the oxidant at a faster rate than the activated carbon surface, and, thus, preferentially removes the oxidant from solution before extensive oxidation of the carbon surface can occur. Further, unlike many oxide species which form at activated carbon surfaces and require high temperature treatments to be reduced, oxide species which form at the surface of a noble metal typically are easily reduced by the reducing agents present in or added to the reaction mixture (e.g., the amine fragment cleaved, formaldehyde, formic acid, $H_2$, etc.), thus restoring the noble metal surface to a reduced state. In this manner, the catalyst of this invention advantageously exhibits significantly longer life as long as the noble metal is not lost by leaching, or sintered (i.e., in the form of undesirably thick layers or clumps) by processes such as dissolution and re-deposition or noble metal agglomeration.

Also, depending on the particular oxidation reaction, a noble metal may be more effective than carbon at effecting the oxidation. For example, in the context of the oxidative cleavage of PMIDA to form N-(phosphonomethyl)glycine, although a carbon catalyst can be used in the oxidation of PMIDA to N-(phosphonomethyl)glycine, it is the noble metal component that primarily effects the oxidation of the undesirable formaldehyde and formic acid by-products into the more preferred by-products, carbon dioxide and water.

Oxygen-containing functional groups (e.g., carboxylic acids, ethers, alcohols, aldehydes, lactones, ketones, esters, amine oxides, and amides) at the surface of the carbon support tend to increase noble metal leaching and potentially increase noble metal sintering during liquid phase oxidation reactions, and, thus, reduce the ability of the catalyst to oxidize oxidizable substrates, particularly formaldehyde and formic acid during the PMIDA oxidation reaction. As used herein, an oxygen-containing functional group is "at the surface of the carbon support" if it is bound to an atom of the carbon support and is able to chemically or physically interact with compositions within the reaction mixture or with the metal atoms deposited on the carbon support.

Many of the oxygen-containing functional groups that reduce noble metal resistance to leaching and sintering and reduce the activity of the catalyst desorb from the carbon support as carbon monoxide when the catalyst is heated at a high temperature (e.g., 900° C.) in an inert atmosphere (e.g., helium or argon). Thus, measuring the amount of CO desorption from a fresh catalyst (i.e., a catalyst that has not previously been used in a liquid phase oxidation reaction) under high temperatures is one method that may be used to analyze the surface of the catalyst to predict noble metal retention and maintenance of catalyst activity. One way to measure CO desorption is by using thermogravimetric analysis with in-line mass spectroscopy ("TGA-MS"). Preferably, no greater than about 1.2 mmole of carbon monoxide per gram of catalyst desorb from the catalyst when a dry, fresh sample of the catalyst in a helium atmosphere is subjected to a temperature which is increased from about 20° to about 900° C. at about 10° C. per minute, and then held constant at about 900° C. for about 30 minutes. More preferably, no greater than about 0.7 mmole of carbon monoxide per gram of fresh catalyst desorb under those conditions, even more preferably no greater than about 0.5 mmole of carbon monoxide per gram of fresh catalyst desorb, and most preferably no greater than about 0.3 mmole of carbon monoxide per gram of fresh catalyst desorb. A catalyst is considered "dry" when the catalyst has a moisture content of less than 1% by weight. Typically, a catalyst may be dried by placing it into a $N_2$ purged vacuum of about 25 inches of Hg at a temperature of about 120° C. for about 16 hours.

Measuring the number of oxygen atoms at the surface of a fresh catalyst support is another method which may be used to analyze the catalyst to predict noble metal retention and maintenance of catalytic activity. Using, for example, x-ray photoelectron spectroscopy, a surface layer of the support which is about 50 Å in thickness is analyzed. Presently available equipment used for x-ray photoelectron spectroscopy typically is accurate to within ±20%. Typically, a ratio of carbon atoms to oxygen atoms at the surface (as measured by presently available equipment for x-ray photoelectron spectroscopy) of at least about 20:1 (carbon atoms:oxygen atoms) is suitable. Preferably, however, the ratio is at least about 30:1, more preferably at least about 40:1, even more preferably at least about 50:1, and most preferably at least about 60:1. In addition, the ratio of oxygen atoms to metal atoms at the surface (again, as measured by presently available equipment for x-ray photoelectron spectroscopy) preferably is less than about 8:1 (oxygen atoms:metal atoms). More preferably, the ratio is less than 7:1, even more preferably less than about 6:1, and most preferably less than about 5:1.

In general, the carbon supports used in the present invention are well known in the art. Activated, non-graphitized carbon supports are preferred. These supports are characterized by high adsorptive capacity for gases, vapors, and colloidal solids and relatively high specific surface areas. The support suitably may be a carbon, char, or charcoal produced by means known in the art, for example, by destructive distillation of wood, peat, lignite, coal, nut shells, bones, vegetable, or other natural or synthetic carbonaceous matter, but preferably is "activated" to develop adsorptive power. Activation usually is achieved by heating to high temperatures (from about 800° to about 900° C.) with steam or with carbon dioxide which brings about a porous particle structure and increased specific surface area. In some cases, hygroscopic substances, such as zinc chloride and/or phosphoric acid or sodium sulfate, are added before the destructive distillation or activation, to increase adsorptive capacity. Preferably, the carbon content of the carbon support ranges from about 10% for bone charcoal to about 98% for some wood chars and nearly 100% for activated carbons derived from organic polymers. The non-carbonaceous matter in commercially available activated carbon materials normally will vary depending on such factors as precursor origin, processing, and activation method. Many commercially available carbon supports contain small amounts of metals. Carbon supports having the fewest oxygen-containing functional groups at their surfaces are most preferred.

The form of the carbon support is not critical. In one embodiment of this invention, the support is a monolithic support. Suitable monolithic supports may have a wide variety of shapes. Such a support may be, for example, in the form of a screen or honeycomb. Such a support may also, for example, be in the form of a reactor impeller.

In a particularly preferred embodiment, the support is in the form of particulates. Because particulate supports are especially preferred, most of the following discussion focuses on embodiments which use a particulate support. It should be recognized, however, that this invention is not limited to the use of particulate supports.

Suitable particulate supports may have a wide variety of shapes. For example, such supports may be in the form of granules. Even more preferably, the support is in the form of a powder. These particulate supports may be used in a reactor system as free particles, or, alternatively, may be bound to a structure in the reactor system, such as a screen or an impeller.

Typically, a support which is in particulate form comprises a broad size distribution of particles. For powders, preferably at least about 95% of the particles are from about 2 to about 300 $\mu$m in their largest dimension, more preferably at least about 98% of the particles are from about 2 to about 200 $\mu$m in their largest dimension, and most preferably about 99% of the particles are from about 2 to about 150 $\mu$m in their largest dimension with about 95% of the particles being from about 3 to about 100 $\mu$m in their largest dimension. Particles being greater than about 200 $\mu$m in their largest dimension tend to fracture into super-fine particles (i.e., less than 2 $\mu$m in their largest dimension), which are difficult to recover.

The specific surface area of the carbon support, measured by the BET (Brunauer-Emmett-Teller) method using $N_2$, is preferably from about 10 to about 3,000 $m^2/g$ (surface area of carbon support per gram of carbon support), more preferably from about 500 to about 2,100 $m^2/g$, and still more preferably from about 750 to about 2,100 $m^2/g$. In some embodiments, the most preferred specific surface area is from about 750 to about 1,750 $m^2/g$.

The pore volume of the support may vary widely. Using the measurement method described in Example 1, the pore volume preferably is from about 0.1 to about 2.5 ml/g (pore volume per gram of catalyst), more preferably from about 0.2 to about 2.0 ml/g, and most preferably from about 0.4 to about 1.7 ml/g. Catalysts comprising supports with pore volumes greater than about 2.5 ml/g tend to fracture easily. On the other hand, catalysts comprising supports having pore volumes less than 0.1 ml/g tend to have small surface areas and therefore low activity.

Carbon supports for use in the present invention are commercially available from a number of sources. The following is a listing of some of the activated carbons which may be used with this invention: Darco G-60 Spec and Darco X (ICI-America, Wilmington, Del.); Norit SG Extra, Norit EN4, Norit EXW, Norit A, Norit Ultra-C, Norit ACX, and Norit 4×14 mesh (Amer. Norit Co., Inc., Jacksonville, Fla.); Gl-9615, VG-8408, VG-8590, NB-9377, XZ, NW, and JV (Barnebey-Cheney, Columbus, Ohio); BL Pulv., PWA Pulv., Calgon C 450, and PCB Fines (Pittsburgh Activated Carbon, Div. of Calgon Corporation, Pittsburgh, Pa.); P-100 (No. Amer. Carbon, Inc., Columbus, Ohio); Nuchar CN, Nuchar C-1000 N, Nuchar C-190 A, Nuchar C-115 A, and Nuchar SA-30 (Westvaco Corp., Carbon Department, Covington, Va.); Code 1551 (Baker and Adamson, Division of Allied Amer. Norit Co., Inc., Jacksonville, Fla.); Grade 235, Grade 337, Grade 517, and Grade 256 (Witco Chemical Corp., Activated Carbon Div., New York, N.Y.); and Columbia SXAC (Union Carbide New York, N.Y.).

The catalyst of this invention preferably has one or more noble metal(s) at its surface. Preferably, the noble metal(s) is selected from the group consisting of platinum (Pt), palladium (Pd), ruthenium (Ru), rhodium (Rh), iridium (Ir), silver (Ag), osmium (Os), and gold (Au). In general, platinum and palladium are more preferred, and platinum is most preferred. Because platinum is presently the most preferred noble metal, the following discussion will be directed primarily to embodiments using platinum. It should be understood, however, that the same discussion is generally applicable to the other noble metals and combinations thereof. It also should be understood that the term "noble metal" as used herein means the noble metal in its elemental state as well as the noble metal in any of its various oxidation states.

The concentration of the noble metal deposited at the surface of the carbon support may vary within wide limits. Preferably, it is in the range of from about 0.5 to about 20 wt. % ([mass of noble metal÷total mass of catalyst]×100%), more preferably from about 2.5 to about 10 wt. %, and most preferably from about 3 to about 7.5 wt. %. If concentrations less than 0.5 wt. % are used during the PMIDA oxidation reaction, there tends to be less formaldehyde oxidized, and therefore a greater amount of NMG produced, thereby reducing the N-(phosphonomethyl)glycine yield. On the other hand, at concentrations greater than about 20 wt. %, layers and clumps of noble metal tend to form. Thus, there are fewer surface noble metal atoms per total amount of noble metal used. This tends to reduce the activity of the catalyst and is an uneconomical use of the costly noble metal.

The dispersion of the noble metal at the surface of the carbon support preferably is such that the concentration of surface noble metal atoms is from about 10 to about 400 $\mu$mole/g ($\mu$mole of surface noble metal atoms per gram of catalyst), more preferably, from about 10 to about 150 $\mu$mole/g, and most preferably from about 15 to about 100 $\mu$mole/g. This may be determined, for example, by measuring chemisorption of $H_2$ or CO using a Micromeritics ASAP 2010C (Micromeritics, Norcross, Ga.) or an Altamira AMI100 (Zeton Altamira, Pittsburgh, Pa.).

Preferably, the noble metal is at the surface of the carbon support in the form of metal particles. At least about 90% (number density) of the noble metal particles at the surface of the carbon support are preferably from about 0.5 to about 35 nm in their largest dimension, more preferably from about 1 to about 20 nm in their largest dimension, and most preferably from about 1.5 to about 10 nm in their largest dimension. In a particularly preferred embodiment, at least about 80% of the noble metal particles at the surface of the carbon support are from about 1 to about 15 nm in their largest dimension, more preferably from about 1.5 to about 10 nm in their largest dimension, and most preferably from about 1.5 to about 7 nm in their largest dimension. If the noble metal particles are too small, there tends to be an increased amount of leaching when the catalyst is used in an environment that tends to solubilize noble metals, as is the case when oxidizing PMIDA to form N-(phosphonomethyl) glycine. On the other hand, as the particle size increases, there tends to be fewer noble metal surface atoms per total amount of noble metal used. As discussed above, this tends to reduce the activity of the catalyst and is also an uneconomical use of the costly noble metal.

In addition to the noble metal, at least one promoter may be at the surface of the carbon support. As defined herein, a "promoter" is a metal that tends to increase catalyst selectivity, activity, and/or stability. A promoter additionally may reduce noble metal leaching. Although the promoter usually is deposited onto the surface of the carbon support in a promoter deposition step, the carbon support itself may also (or alternatively) naturally contain a promoter. A promoter which is deposited or exists naturally on the catalyst surface before the carbon support surface is finally reduced (see Section (B) (4) below) is referred to herein as a "catalyst-surface promoter."

The catalyst-surface promoter may, for example, be an additional noble metal(s) at the surface of the carbon support. For example, depending on the application, ruthenium and palladium may act as catalyst-surface promoters on a catalyst comprising platinum deposited at a carbon support surface. The catalyst-surface promoter(s) alternatively may be, for example, a metal selected from the group consisting of tin (Sn), cadmium (Cd), magnesium (Mg), manganese (Mn), nickel (Ni), aluminum (Al), cobalt (Co), bismuth (Bi), lead (Pb), titanium (Ti), antimony (Sb), selenium (Se), iron (Fe), rhenium (Re), zinc (Zn), cerium (Ce), zirconium (Zr), tellurium (Te), and germanium (Ge). Preferably, the catalyst-surface promoter is selected from the group consisting of bismuth, iron, tin, titanium and tellurium. In a particularly preferred embodiment, the catalyst-surface promoter is tin. In another particularly preferred embodiment, the catalyst-surface promoter is iron. In an additional preferred embodiment, the catalyst-surface promoter is titanium. In a further particularly preferred embodiment, the catalyst comprises both iron and tin at its surface. Use of iron, tin, or both generally (1) reduces noble metal leaching for a catalyst used over several cycles, and (2) tends to increase and/or maintain the activity of the catalyst when the catalyst is used to effect the oxidation of PMIDA. Catalysts comprising iron generally are most preferred because they tend to have the greatest activity and stability with respect to formaldehyde and formic acid oxidation.

In a preferred embodiment, the catalyst-surface promoter is more easily oxidized than the noble metal (in instances where the catalyst-surface promoter is a noble metal as well, the catalyst-surface promoter noble metal preferably is more easily oxidized than the non-promoter noble metal). A promoter is "more easily oxidized" if it has a lower first ionization potential than the noble metal. First ionization potentials for the elements are widely known in the art and may be found, for example, in the *CRC Handbook of Chemistry and Physics* (CRC Press, Inc., Boca Raton, Fla.).

The amount of catalyst-surface promoter at the surface of the carbon support (whether associated with the carbon surface itself, metal, or a combination thereof) may vary within wide limits depending on, for example, the noble metal(s) and catalyst-surface promoter(s) used. Typically, the weight percentage of the catalyst-surface promoter is at least about 0.05% ([mass of catalyst-surface promoter÷total mass of the catalyst]×100%). The weight percent of the catalyst-surface promoter preferably is from about 0.05 to about 10%, more preferably from about 0.1 to about 10%, still more preferably from about 0.1 to about 2%, and most preferably from about 0.2 to about 1.5%. When the catalyst-surface promoter is tin, the weight percent most preferably is from about 0.5 to about 1.5%. Catalyst-surface promoter weight percentages less than 0.05% generally do not promote the activity of the catalyst over an extended period of time. On the other hand, weight percents greater than about 10% tend to decrease the activity of the catalyst.

The molar ratio of noble metal to catalyst-surface promoter (and, in instances where the catalyst-surface promoter is a noble metal as well, the molar ratio of the non-promoter noble metal to the catalyst-surface promoter noble metal) may also vary widely, depending on, for example, the noble metal(s) and catalyst-surface promoter(s) used. Preferably, the ratio is from about 1000:1 to about 0.01:1; more preferably from about 150:1 to about 0.05:1; still more preferably from about 50:1 to about 0.05:1; and most preferably from about 10:1 to about 0.05:1. For example, a catalyst comprising platinum and iron preferably has a molar ratio of platinum to iron of about 3:1.

In a particularly preferred embodiment of this invention, the noble metal (e.g., Pt) is alloyed with at least one catalyst-surface promoter (e.g., Sn, Fe, or both) to form alloyed metal particles (and, in instances where the catalyst-surface promoter is a noble metal as well, the non-promoter noble metal preferably is alloyed with the catalyst-surface promoter noble metal). A catalyst comprising a noble metal alloyed with at least one catalyst-surface promoter tends to have all the advantages discussed above with respect to catalysts comprising a catalyst-surface promoter in general. Catalysts comprising a noble metal alloyed with at least one catalyst-surface promoter also tend to exhibit greater resistance to catalyst-surface promoter leaching and further stability from cycle to cycle with respect to formaldehyde and formic acid oxidation. See, e.g., Example 17.

The term "alloy" encompasses any metal particle comprising a noble metal and at least one catalyst-surface promoter, irrespective of the precise manner in which the noble metal and catalyst-surface promoter atoms are disposed within the particle (although it is generally preferable to have a portion of the noble metal atoms at the surface of the alloyed metal particle). The alloy may be, for example, any of the following:

1. An intermetallic compound. An intermetallic compound is a compound comprising a noble metal and a promoter (e.g., $Pt_3Sn$).
2. A substitutional alloy. A substitutional alloy has a single, continuous phase, irrespective of the concentrations of the noble metal and promoter atoms. Typically, a substitutional alloy contains noble metal and promoter atoms which are similar in size (e.g., platinum and silver; or platinum and palladium). Substitutional alloys are also referred to as "monophasic alloys."
3. A multiphasic alloy. A multiphasic alloy is an alloy that contains at least two discrete phases. Such an alloy may contain, for example $Pt_3Sn$ in one phase, and tin dissolved in platinum in a separate phase.
4. A segregated alloy. A segregated alloy is a metal particle wherein the particle stoichiometry varies with distance from the surface of the metal particle.
5. An interstitial alloy. An interstitial alloy is a metal particle wherein the noble metal and promoter atoms are combined with non-metal atoms, such as boron, carbon, silicon, nitrogen, phosphorus, etc.

Preferably, at least about 80% (number density) of the alloyed metal particles are from about 0.5 to about 35 nm in their largest dimension, more preferably from about 1 to about 20 nm in their largest dimension, still more preferably from about 1 to about 15 nm in their largest dimension, and most preferably from about 1.5 to about 7 nm in their largest dimension.

The alloyed metal particles need not have a uniform composition; the compositions may vary from particle to particle, or even within the particles themselves. In addition, the catalyst may further comprise particles consisting of the noble metal alone or the catalyst-surface promoter alone. Nevertheless, it is preferred that the composition of metal particles be substantially uniform from particle to particle and within each particle, and that the number of noble metal atoms in intimate contact with catalyst-surface promoter atoms be maximized. It is also preferred, although not essential, that the majority of noble metal atoms be alloyed with a catalyst-surface promoter, and more preferred that substantially all of the noble metal atoms be alloyed with a catalyst-surface promoter. It is further preferred, although not essential, that the alloyed metal particles be uniformly distributed at the surface of the carbon support.

Regardless of whether the catalyst-surface promoter is alloyed to the noble metal, it is presently believed that the catalyst-surface promoter tends to become oxidized if the catalyst is exposed to an oxidant over a period of time. For example, an elemental tin catalyst-surface promoter tends to oxidize to form $Sn(II)O$, and $Sn(II)O$ tends to oxidize to form $Sn(IV)O_2$. This oxidation may occur, for example, if the catalyst is exposed to air for more than about 1 hour. Although such catalyst-surface promoter oxidation has not been observed to have a significant detrimental effect on noble metal leaching, noble metal sintering, catalyst activity, or catalyst stability, it does make analyzing the concentration of detrimental oxygen-containing functional groups at the surface of the carbon support more difficult. For example, as discussed above, the concentration of detrimental oxygen-containing functional groups (i.e., oxygen-containing functional groups that reduce noble metal resistance to leaching and sintering, and reduce the activity of the catalyst) may be determined by measuring (using, for example, TGA-MS) the amount of CO that desorbs from the catalyst under high temperatures in an inert atmosphere. However, it is presently believed that when an oxidized catalyst-surface promoter is present at the surface, the oxygen atoms from the oxidized catalyst-surface promoter tend to react with carbon atoms of the support at high temperatures in an inert atmosphere to produce CO, thereby creating the illusion of more detrimental oxygen-containing functional groups at the surface of the support than actually exist. Such oxygen atoms of an oxidized catalyst-surface promoter also can interfere with obtaining a reliable prediction of noble metal leaching, noble metal sintering, and catalyst activity from the simple measurement (via, for example, x-ray photoelectron spectroscopy) of oxygen atoms at the catalyst surface.

Thus, when the catalyst comprises at least one catalyst-surface promoter which has been exposed to an oxidant and thereby has been oxidized (e.g., when the catalyst has been exposed to air for more than about 1 hour), it is preferred that the catalyst-surface promoter first be substantially reduced (thereby removing the oxygen atoms of the oxidized catalyst-surface promoter from the surface of the catalyst) before attempting to measure the amount of detrimental oxygen-containing functional groups at the surface of the carbon support. This reduction preferably is achieved by heating the catalyst to a temperature of about 500° C. for about 1 hour in an atmosphere consisting essentially of $H_2$. The measurement of detrimental oxygen-containing functional groups at the surface preferably is performed (a) after this reduction, and (b) before the surface is exposed to an oxidant following the reduction. Most preferably, the measurement is taken immediately after the reduction.

The preferred concentration of metal particles at the surface of the carbon support depends, for example, on the size of the metal particles, the specific surface area of the carbon support, and the concentration of noble metal on the catalyst. It is presently believed that, in general, the preferred concentration of metal particles is roughly from about 3 to about 1,500 particles/$\mu m^2$ (i.e., number of metal particles per $\mu m^2$ of surface of carbon support), particularly where: (a) at least about 80% (number density) of the metal particles are from about 1.5 to about 7 nm in their largest dimension, (b) the carbon support has a specific surface area of from about 750 to about 2100 $m^2/g$ (i.e., $m^2$ of surface of carbon support per gram of carbon support), and (c) the concentration of noble metal at the carbon support surface is from about 1 to about 10 wt. % ([mass of noble metal÷total mass of catalyst]×100%). In more preferred embodiments, narrower ranges of metal particle concentrations and noble metal concentrations are desired. In one such embodiment, the concentration of metal particles is from about 15 to about 800 particles/$\mu m^2$, and the concentration of noble metal at the carbon support surface is from about 2 to about 10 wt. %. In an even more preferred embodiment, the concentration of metal particles is from about 15 to about 600 particles/$\mu m^2$, and the concentration of noble metal at the carbon support surface is from about 2 to about 7.5 wt. %. In the most preferred embodiment, the concentration of the metal particles is from about 15 to about 400 particles/$\mu m^2$, and the concentration of noble metal at the carbon support surface is about 5 wt. %. The concentration of metal particles at the surface of the carbon support may be measured using methods known in the art.

B. Process for the Preparation of the Oxidation Catalyst

1. Deoxygenation of the Carbon Support

The surface of the carbon support preferably is deoxygenated before the noble metal is deposited onto it. Preferably, the surface is deoxygenated using a high-temperature deoxygenation treatment. Such a treatment may be a single-step or a multi-step scheme which, in either case, results in an overall chemical reduction of oxygen-containing functional groups at the surface of the carbon support.

In a two-step high-temperature deoxygenation treatment, the carbon support preferably is first treated with a gaseous or liquid phase oxidizing agent to convert oxygen-containing functionalities in relatively lower oxidation states (e.g., ketones, aldehydes, and alcohols) into functionalities in relatively higher oxidation states (e.g., carboxylic acids), which are easier to cleave from the surface of the catalyst at high temperatures. Representative liquid phase oxidizing agents include nitric acid, $H_2O_2$, chromic acid, and hypochlorite, with concentrated nitric acid comprising from about 10 to about 80 grams of $HNO_3$ per 100 grams of aqueous solution being preferred. Representative gaseous oxidants include molecular oxygen, ozone, nitrogen dioxide, and nitric acid vapors. Nitric acid vapors are the preferred oxidizing agent. With a liquid oxidant, temperatures in the range of from about 60° to about 90° C. are appropriate, but with gaseous oxidants, it is often advantageous to use temperatures of from about 50° to about 500° C. or even greater. The time during which the carbon is treated with the oxidant can vary widely from about 5 minutes to about 10 hours. Preferably, the reaction time is from about 30 minutes to about 6 hours. Experimental results indicate that carbon load, temperature, oxidant concentration, etc. in the first treatment step are not narrowly critical to achieving the desired oxidation of the carbon material and thus may be governed by convenience over a wide range. The highest possible carbon load is preferred for economic reasons.

In the second step, the oxidized carbon support is pyrolyzed (i.e., heated) at a temperature preferably in the range of from about 500° to about 1500° C., and more preferably from about 600° to about 1,200° C., in a nitrogen, argon, helium, or other non-oxidizing environment (i.e., an environment consisting essentially of no oxygen) to drive off the oxygen-containing functional groups from the carbon surface. At temperatures greater than about 500° C., an environment may be used which comprises a small amount of ammonia (or any other chemical entity which will generate $NH_3$ during pyrolysis), steam, or carbon dioxide, all of which may aid in the pyrolysis. As the temperature of the carbon support is cooled to temperatures less than about 500° C., however, the presence of oxygen-containing gases such as steam or carbon dioxide may lead to the re-formation of surface oxides and thus, is preferably avoided. Accordingly, the pyrolysis is preferably conducted in a non-oxidizing atmosphere (e.g., nitrogen, argon, or helium). In one embodiment, the non-oxidizing atmosphere comprises ammonia, which tends to produce a more active catalyst in a shorter time as compared to pyrolysis in the other atmospheres. The pyrolysis may be achieved, for example, using a rotary kiln, a fluidized bed reactor, or a conventional furnace.

The carbon support generally is pyrolyzed for a period of from about 5 minutes to about 60 hours, preferably from about 10 minutes to about 6 hours. Shorter times are preferred because prolonged exposure of the carbon at elevated temperatures tends to reduce the activity of the catalyst. Without being bound to any particular theory, it is presently believed that prolonged heating at pyrolytic temperatures favors the formation of graphite, which is a less preferred form of a carbon support because it normally has less surface area. As discussed above, a more active catalyst typically may be produced in a shorter time by using an atmosphere which comprises ammonia.

In a preferred embodiment of this invention, high-temperature deoxygenation is carried out in one step. This one-step treatment may consist of merely performing the pyrolysis step of the two-step high-temperature deoxygenation treatment discussed above. More preferably, however, the single-step treatment consists of pyrolyzing the carbon support as described above while simultaneously passing a gas stream comprising $N_2$, $NH_3$ (or any other chemical entity which will generate $NH_3$ during pyrolysis), and steam over the carbon. Although it is not a critical feature of this invention, the flow rate of the gas stream preferably is fast enough to achieve adequate contact between the fresh gas reactants and the carbon surface, yet slow enough to prevent excess carbon weight loss and material waste. A non-reactive gas may be used as a diluent to prevent severe weight loss of the carbon.

2. Deposition of the Noble Metal(s)

Methods used to deposit the noble metal onto the surface of the carbon support are generally known in the art, and include liquid phase methods such as reaction deposition techniques (e.g., deposition via reduction of noble metal compounds, and deposition via hydrolysis of noble metal compounds), ion exchange techniques, excess solution impregnation, and incipient wetness impregnation; vapor phase methods such as physical deposition and chemical deposition; precipitation; electrochemical deposition; and electroless deposition. See generally, Cameron, D. S., Cooper, S. J., Dodgson, I. L., Harrison, B., and Jenkins, J. W. "Carbons as Supports for Precious Metal Catalysts," *Catalysis Today*, 7, 113–137 (1990). Catalysts comprising noble metals at the surface of a carbon support also are commercially available, e.g., Aldrich Catalog No. 20,593-1, 5% platinum on activated carbon (Aldrich Chemical Co., Inc., Milwaukee, Wis.); Aldrich Catalog No. 20,568-0, 5% palladium on activated carbon.

Preferably, the noble metal is deposited via a reactive deposition technique comprising contacting the carbon support with a solution comprising a salt of the noble metal, and then hydrolyzing the salt. An example of a suitable platinum salt which is relatively inexpensive is hexachloroplatinic acid ($H_2PtCl_6$). The use of this salt to deposit platinum onto a carbon support via hydrolytic deposition is illustrated in Example 3.

In one embodiment of this invention, the noble metal is deposited onto the surface of the carbon support using a solution comprising a salt of a noble metal in one of its more reduced oxidation states. For example, instead of using a salt of Pt(IV) (e.g., $H_2PtCl_6$), a salt of Pt(II) is used. In another embodiment, platinum in its elemental state (e.g., colloidal platinum) is used. Using these more reduced metal precursors leads to less oxidation of the carbon support and, therefore, less oxygen-containing functional groups being formed at the surface of the support while the noble metal is being deposited onto the surface. One example of a Pt(II) salt is $K_2PtCl_4$. Another potentially useful Pt(II) salt is diamminedinitrito platinum(II). Example 11 shows that using this salt to deposit the noble metal produces a catalyst which is more resistant to leaching than a catalyst prepared using $H_2PtCl_6$ as the metal precursor. Without being bound by any particular theory, it is believed that this is due to the fact that diamminedinitrito platinum(II) generates ammonia in-situ during reduction which further promotes removal of the oxygen-containing functional groups at the surface of the carbon support. This benefit, however, should be weighed against a possible explosion danger associated with the use of diamminedinitrito platinum(II).

3. Deposition of a Catalyst-Surface Promoter(s)

A catalyst-surface promoter(s) may be deposited onto the surface of the carbon support before, simultaneously with, or after deposition of the noble metal onto the surface. Methods used to deposit a promoter onto the surface of the carbon support are generally known in the art, and include the same methods used to deposit a noble metal discussed above. In one embodiment, a salt solution comprising a promoter is used to deposit the catalyst-surface promoter. A suitable salt that may be used to deposit bismuth is $Bi(NO_3)_3.5H_2O$, a suitable salt that may be used to deposit iron is $FeCl_3.6H_2O$, and a suitable salt that may be used to deposit tin is $SnCl_2.2H_2O$. It should be recognized that more than one catalyst-surface promoter may be deposited onto the surface of the carbon support. Examples 13, 14, 15, and 17 demonstrate depositing a promoter onto a carbon surface with a salt solution comprising a promoter. Example 18 demonstrates depositing more than one promoter (i.e., iron and Sn) onto a carbon surface using salt solutions comprising the promoters.

As noted above, a catalyst comprising a noble metal alloyed with at least one catalyst-surface promoter is particularly preferred. There are a variety of possible preparative techniques known in the art which may be used to form a multi-metallic alloy at support surfaces. See, e.g., V. Ponec & G. C. Bond, *Catalysis by Metals and Alloys,* "Studies in Surface Science and Catalysis," Vol. 95 (B. Delmon. & J. T. Yates, advisory eds., Elsevier Science B. V., Amsterdam, Netherlands).

In one of the more preferred embodiments, reactive deposition is used to form metal particles containing a noble metal alloyed with a catalyst-surface promoter. Reactive deposition may comprise, for example, reductive deposition wherein a surface of a carbon support is contacted with a solution comprising: (a) a reducing agent; and (b) (i) a compound comprising the noble metal and a compound comprising the promoter, or (ii) a compound comprising both the noble metal and the promoter. A wide range of reducing agents may be used, such as sodium borohydride, formaldehyde, formic acid, sodium formate, hydrazine hydrochloride, hydroxylamine, and hypophosphorous acid. Compounds comprising a noble metal and/or a promoter include, for example:

1. Halide compounds. These include, for example, $H_2PtCl_6$, $K_2PtCl_4$, $Pt_2Br_6^{2-}$, $K_2PdCl_4$, $AuCl_4^{1-}$, $RuCl_3$, $RhCl_3 \cdot 3H_2O$, $K_2RuCl_6$, $FeCl_3 \cdot 6H_2O$, $(SnCl_3)^{1-}$, $SnCl_4$, $ReCl_6$, $FeCl_2$, and $TiCl_4$.
2. Oxide and oxy chloride compounds. These include, for example, $RuO_4^{2-}$ and $M_2SnO_4$.
3. Nitrate compounds. These include, for example, $Fe(NO_3)_3$.
4. Amine complexes. These include, for example, [Pt$(NH_3)_4$]Cl$_2$, [Pd$(NH_3)_4$]Cl$_2$, Pt $(NH_3)_2Cl_2$, Pt $(NH_3)_4$] $PtCl_4$, $Pd(NH_2CH_2CH_2NH_2)Cl_2$, $Pt(NH_2CH_2CH_2NH_2)_2Cl_2$, and [Ru$(NH_3)_5$Cl]Cl$_2$.
5. Phosphine complexes. These include, for example, $Pt(P(CH_3)_3)_2Cl_2$; $IrClCO(P(C_6H_5)_3)_2$; $PtClH(PR_3)_2$, wherein each R is independently a hydrocarbyl, such as methyl, ethyl, propyl, phenyl, etc.
6. Organometallic complexes. These include, for example, $Pt_2(C_3H_6)_2Cl_4$; $Pd_2(C_2H_4)_2Cl_4$; $Pt(CH_3COO)_2$, $Pd(CH_3COO)_2$; $K[Sn(HCOO)_3]$; $Fe(CO)_5$; $Fe_3(CO)_{12}$; $Fe_4(CO)_{16}$; $Sn_3(CH_3)_4$; and $Ti(OR)_4$, wherein each R is independently a hydrocarbyl, such as methyl, ethyl, propyl, phenyl, etc.
7. Noble metal/promoter complexes. These include, for example, $Pt_3 (SnCl_3)_2(C_8H_{12})_3$ and $[Pt(SnCl_3)_5]^{3-}$.

In a particularly preferred embodiment, hydrolysis reactions are used to deposit a noble metal alloyed with a catalyst-surface promoter. In this instance, ligands containing the noble metal and promoter are formed, and then hydrolyzed to form well-mixed, metal oxide and metal hydroxide clusters at the surface of the carbon support. The ligands may be formed, for example, by contacting the surface of the support with a solution comprising (a) a compound comprising the noble metal and a compound comprising the promoter, or (b) a compound comprising both the noble metal and the promoter. Suitable compounds comprising a noble metal and/or a promoter are listed above with respect to reductive deposition. Hydrolysis of the ligands may be achieved, for example, by heating (e.g., at a temperature of at least about 60° C.) the mixture. Example 17 further demonstrates the use of hydrolysis reactions to deposit a noble metal (i.e., platinum) alloyed with a catalyst-surface promoter (i.e., iron).

In addition to the above-described reactive deposition techniques, there are many other techniques which may be used to form the alloy. These include, for example:

1. Forming the alloy by introducing metal compounds (which may be simple or complex, and may be covalent or ionic) to the surface of the support via impregnation, adsorption from a solution, and/or ion exchange.
2. Forming the alloy by vacuum co-deposition of metal vapors containing the noble metal and promoter onto the surface.
3. Forming the alloy by depositing one or more metals onto a pre-deposited metal belonging to Group 8, 9, or 10 of the Periodic Table of the Elements (i.e., Fe, Co, Ni, Ru, Rh, Pd, Os, Ir, and Pt) via, for example, electrolytic or electroless plating.
4. Forming the alloy by: (a) depositing metal complexes containing metals in the zero valence state (e.g., carbonyl, pi-allyl, or cyclopentadienyl complexes of the noble metal and of the promoter) at the surface of the carbon support; and (b) removing the ligands by, for example, heating or reduction to form the alloy particles at the surface.
5. Forming the alloy by contacting a solution containing a metal compound (e.g., a metal chloride or a metal alkyl compound) with a pre-deposited metal hydride containing a metal belonging to Group 8, 9, or 10 of the Periodic Table of the Elements.
6. Forming the alloy by co-depositing, either simultaneously or sequentially, metal complexes (either pre-formed or formed in situ) containing the noble metal(s) and promoter(s) at the surface of the carbon support.
7. Forming the alloy by pre-forming alloy particles as colloids or aerosols, and then depositing the pre-formed alloy particles at the surface of the carbon support. To illustrate, colloidal particles containing platinum and iron may be easily formed by boiling a dilute solution of $H_2PtCl_6$ and $SnCl_2.2H_2O$ with a sodium citrate solution. Protecting agents (e.g., carbohydrates, polymers, lipophilic quaternary nitrogen salts) may be used to effectively control metal alloy particle growth. This technique, therefore, is often useful to form a narrow distribution of alloy particle sizes.

It should be recognized that the above-discussed techniques for forming an alloy are simply illustrative, and not exhaustive. Using the teachings of this specification and the general knowledge of the art, one of ordinary skill in the art may routinely determine which of the numerous alloy preparation techniques known in the art are suitable to a particular use.

Regardless of the technique used to form the alloy, after the metals have been deposited at the surface of the carbon support, it is often preferable to dry the support using, for example, a sub-atmospheric, non-oxidizing environment (preferably, $N_2$, a noble gas, or both). Use of a drying step is particularly preferred where the surface of the support is to be subsequently reduced by heating the surface (and even more preferred where the heating is to be conducted in a non-oxidizing environment). Preferably, the support is dried to reduce the moisture content of the support to less than about 5% by weight.

It should be recognized that reducing the surface of the carbon support after deposition of the noble metal(s) and catalyst-surface promoter(s) typically increases the extent of noble metal alloyed with a catalyst-surface promoter. Such reduction also often tends to increase the number of particles falling within the preferred size range.

4. Reduction of the Carbon Support Surface

After the carbon support has been impregnated with the noble metal(s) (and catalyst-surface promoter(s), if any), the surface of the catalyst preferably is reduced. The surface of the catalyst suitably may be reduced, for example, by heating the surface at a temperature of at least about 400° C. It is especially preferable to conduct this heating in a non-oxidizing environment (e.g., nitrogen, argon, or helium). It is also more preferred for the temperature to be greater than about 500° C. Still more preferably, the temperature is from about 550° to about 1,200° C., and most preferably from about 550° to about 900° C. Temperatures less than 400° C. tend to be unsatisfactory for removing the oxygen-containing functional groups from the surface of the carbon support. On the other hand, temperatures greater than 1,200° C. tend to reduce the activity of the catalyst. Temperatures of from about 400° to about 500° C. preferably are used only if the surface of the carbon support has a carbon atom to oxygen atom ratio of at least about 20:1 before the noble metal is deposited onto the surface.

In a particularly preferred embodiment, the surface of the catalyst is reduced by a process comprising exposing the surface to a reducing environment. For example, before the heating, the catalyst sample may be pre-treated with a liquid-phase reducing agent, such as formaldehyde or formic acid. Even more preferably, the heating is conducted in the presence of a gas-phase reducing agent (the method of heating the catalyst in the presence of a gas-phase reducing agent will sometimes be referred to as "high-temperature gas-phase reduction"). Various gas-phase reducing agents may be used during the heating, including but not limited to $H_2$, ammonia, and carbon monoxide. Hydrogen gas is most preferred because the small molecular size of hydrogen allows better penetration into the deepest pores of the carbon support. Preferably, the remainder of the gas consists essentially of a non-oxidizing gas, such as nitrogen, argon, or helium. The gas may comprise any finite concentration of $H_2$, although $H_2$ concentrations of less than about 1.0% are disadvantageous because of the time they tend to require to reduce the surface of the support. Preferably, the gas comprises from about 5 to about 50 volume % $H_2$, and most preferably from about 5 to about 25 volume % $H_2$.

The preferred amount of time that the catalyst surface is heated depends on the rate of mass transfer of the reducing agent to the catalyst surface. When the reducing agent is a non-oxidizing gas comprising from about 10 to about 20 volume % $H_2$, the surface preferably is heated for a time of from about 15 minutes to about 24 hours at a temperature of from about 550° to about 900° C. with a space velocity within the range of from about 1 to about 5,000 hour$^{-1}$. More preferably, the space velocity is from about 10 to about 2,500 hour$^{-1}$, and even more preferably from about 50 to about 750 hour$^{-1}$. In the most preferred embodiment, the heat-treatment is conducted at the above preferred temperatures and space velocities for a time of from about 1 to about 10 hours. Heating the surface at space velocities of less than about 1 hour$^{-1}$ is disadvantageous because the oxygen-containing functional groups at the surface of the carbon support may not be sufficiently destroyed. On the other hand, heating the surface at space velocities greater than about 5,000 hour$^{-1}$ is not economical.

Pre-existing oxygen-containing functional groups at the surface of the carbon support generally are not necessary, or even desired, to obtain adequate noble metal dispersion and retention. Without being bound by any particular theory, it is believed that this heating step enhances the platinum-carbon interaction on the catalyst by removing oxygen-containing functional groups at the surface of the carbon support, including those formed by depositing the noble metal onto the surface. It is believed that these oxygen-containing functional groups are unstable anchor sites for the noble metal because they tend to interfere with the potentially stronger n interactions between the noble metal and the carbon support. Heating alone will decompose and thereby remove many of the oxygen-containing functional groups at the surface of the carbon support. However, by heating the surface in the presence of a reducing agent (e.g., $H_2$), more oxygen-containing functional groups are able to be eliminated.

If the carbon atom to oxygen atom ratio at the surface of the carbon support is less than about 20:1 before the noble metal is deposited onto the surface of the support, the surface preferably is reduced using the above-described high-temperature gas-phase reduction treatment at a temperature greater than about 500° C., although the surface may optionally be treated with other reducing environments in addition to high-temperature gas-phase reduction. On the other hand, if the surface of the carbon support has a carbon atom to oxygen atom ratio which is at least about 20:1 before the noble metal is deposited onto the surface, various alternative reducing environments may be used instead of high-temperature gas-phase reduction.

The surface of the catalyst may be reduced, at least in part, by treating it with an amine, such as urea, a solution comprising ammonium ions (e.g., ammonium formate or ammonium oxalate), or ammonia gas, with ammonia gas or a solution comprising ammonium ions being most preferred. This amine treatment preferably is used in addition to other reduction treatments, and most preferably is used before high-temperature gas-phase reduction. In one such embodiment, the noble metal is deposited onto the surface by treating it with a noble metal precursor solution comprising ammonium ions. Alternatively, after the noble metal is deposited onto the surface of the support, the support may be washed with a solution comprising ammonium ions or placed into contact with a gas comprising ammonia. Most preferably, the catalyst surface is washed with diluted aqueous ammonia after depositing the noble metal. In this instance, the catalyst is added to pure water and stirred for a few hours to wet the surface of the catalyst. Next, while continuing to stir the catalyst slurry, a solution comprising ammonium ions is added to the catalyst slurry in an amount sufficient to produce a pH of greater than about 7, more preferably from about 8 to about 12, and most preferably from about 9.5 to about 11.0. Because the temperature and pressure are not critical, this step preferably is performed at room temperature and atmospheric pressure. Example 10 further demonstrates this reduction treatment.

Sodium borohydride ($NaBH_4$) also may be used to reduce the surface of the catalyst. As with the amine treatment, this treatment preferably is used in addition to other reduction treatments, and most preferably is used before high-temperature gas-phase reduction. Preferably, after depositing the noble metal onto the surface of the support, the support is washed with a solution of $NaBH_4$ in the presence of NaOH at a pH of from about 8 to about 14 for a period of time of from about 15 to about 180 minutes. The amount of $NaBH_4$ used preferably is sufficient to reduce all the noble metal. Because the temperature and pressure are not critical, this step preferably is performed at room temperature and atmospheric pressure. Example 12 further demonstrates this reduction treatment.

It should be recognized that any of the above treatments which may be used to reduce the surface of the catalyst also may be used to deoxygenate the surface of the carbon support before the noble metal is deposited onto the surface.

C. Use of the Oxidation Catalyst

The above-described catalyst may be used for liquid phase oxidation reactions. Examples of such reactions include the oxidation of alcohols and polyols to form aldehydes, ketones, and acids (e.g., the oxidation of 2-propanol to form acetone, and the oxidation of glycerol to form glyceraldehyde, dihydroxyacetone, or glyceric acid); the oxidation of aldehydes to form acids (e.g., the oxidation of formaldehyde to form formic acid, and the oxidation of furfural to form 2-furan carboxylic acid); the oxidation of tertiary amines to form secondary amines (e.g., the oxidation of nitrilotriacetic acid ("NTA") to form iminodiacetic acid ("IDA")); the oxidation of secondary amines to form primary amines (e.g., the oxidation of IDA to form glycine); and the oxidation of various acids (e.g., formic acid or acetic acid) to form carbon dioxide and water.

The above-described catalyst is especially useful in liquid phase oxidation reactions at pH levels less than 7, and in particular, at pH levels less than 3. It also is especially useful in the presence of solvents, reactants, intermediates, or products which solubilize noble metals. One such reaction is the oxidation of PMIDA, a salt of PMIDA, or an ester of PMIDA to form N-(phosphonomethyl)glycine, a salt of N-(phosphonomethyl)glycine, or an ester of N-(phosphonomethyl)glycine in an environment having pH levels in the range of from about 1 to about 2. The description below will disclose with particularity the use of the above-described catalyst to effect the oxidative cleavage of PMIDA, a salt of PMIDA, or an ester of PMIDA to form N-(phosphonomethyl)glycine, a salt of N-(phosphonomethyl)glycine, or an ester of N-(phosphonomethyl)glycine. It should be recognized, however, that the principles disclosed below are generally applicable to other liquid phase oxidative reactions, especially those at pH levels less than 7 and those involving solvents, reactants, intermediates, or products which solubilize noble metals.

To begin the PMIDA oxidation reaction, it is preferable to charge the reactor with the PMIDA substrate (i.e., PMIDA, a salt of PMIDA, or an ester of PMIDA), catalyst, and a solvent in the presence of oxygen. The solvent is most preferably water, although other solvents (e.g., glacial acetic acid) are suitable as well.

The reaction may be carried out in a wide variety of batch, semi-batch, and continuous reactor systems. The configuration of the reactor is not critical. Suitable conventional reactor configurations include, for example, stirred tank reactors, fixed bed reactors, trickle bed reactors, fluidized bed reactors, bubble flow reactors, plug flow reactors, and parallel flow reactors, with stirred tank reactors often being most preferred.

FIG. 1 shows one example of a batch-type embodiment that may be used in accordance with this invention. In this particular embodiment, the oxidation substrate (e.g., PMIDA, a salt of PMIDA, and/or an ester of PMIDA) is introduced into a stirred-tank reactor 3, along with a solvent (most preferably water) and oxygen (e.g., pure oxygen or air). The catalyst is maintained in a catalyst holding tank 1 (also called a "catalyst recycle tank"), and then moved to the stirred-tank reactor 3 to catalyze the oxidation reaction. After essentially all the oxidation substrate has been consumed by the oxidation reaction, the reaction mixture 4 (including the reaction product and the catalyst) is transferred to a filter holding tank 5, and then to a filter 7 where substantially all the catalyst is separated from substantially all the reaction product to form a catalyst stream 9 (containing the catalyst, and, typically, a residual amount of the reaction product) and a product stream 8 containing substantially all the reaction product. The catalyst stream 9 is directed to the catalyst holding tank 1, while the reaction product stream 8 is carried forward for further processing for commercial use. It should be recognized, however, that a portion of the product stream 8 may alternatively, for example, be recycled back to the stirred-tank reactor 3 to supply formaldehyde and/or formic acid to act as a sacrificial reducing agent during a subsequent batch oxidation reaction, as discussed below. For example, the reaction product stream 8 can be passed through an evaporator (not shown) where essentially all the N-(phosphonomethyl) glycine product is precipitated and a separate stream (not shown) is formed containing evaporated formaldehyde, formic acid, and water which is recycled (in whole or in part) back to the stirred-tank reactor 3. Because water is also being recycled, this recycle scheme has the additional benefit of conserving water and reducing waste volume.

When the oxidation reaction is conducted in a continuous reactor system, the residence time in the reaction zone can vary widely depending on the specific catalyst and conditions employed. Typically, the residence time can vary over the range of from about 3 to about 120 minutes. Preferably, the residence time is from about 5 to about 90 minutes, and more preferably from about 5 to about 60 minutes. When the oxidation reaction is conducted in a batch reactor, the reaction time typically varies over the range of from about 15 to about 120 minutes. Preferably, the reaction time is from about 20 to about 90 minutes, and more preferably from about 30 to about 60 minutes.

In a broad sense, the oxidation reaction may be practiced in accordance with the present invention at a wide range of temperatures, and at pressures ranging from sub-atmospheric to super-atmospheric. Use of mild conditions (e.g., room temperature and atmospheric pressure) have obvious commercial advantages in that less expensive equipment may be used. However, operating at higher temperatures and super-atmospheric pressures, while increasing plant costs (equipment and operating costs), tends to improve phase transfer between the liquid and gas phase (e.g., the oxygen source) and increase the PMIDA oxidation reaction rate.

Preferably, the PMIDA reaction is conducted at a temperature of from about 20° to about 180° C., more preferably from about 50° to about 140° C., and most preferably from about 80° to about 110° C. At temperatures greater than about 180° C., the raw materials tend to slowly decompose.

The pressure used during the PMIDA oxidation generally depends on the temperature used. Preferably, the pressure is sufficient to prevent the reaction mixture from boiling. If an oxygen-containing gas is used as the oxygen source, the pressure also preferably is adequate to cause the oxygen to dissolve into the reaction mixture at a rate sufficient such that the PMIDA oxidation is not limited due to an inadequate oxygen supply. The pressure preferably is at least equal to atmospheric pressure. More preferably, the pressure is from about 30 to about 500 psig (about 206 to about 3447 kPa), and most preferably from about 30 to about 130 psig (about 206 to about 896 kPa).

The catalyst concentration preferably is from about 0.1 to about 10 wt. % ([mass of catalyst÷total reaction mass]× 100%). More preferably, the catalyst concentration is from about 0.2 to about 5 wt. %, even more preferably from about 0.3 to about 1.5 wt. %, still even more preferably from about 0.5 to about 1.0 wt. %, and most preferably about 0.75 wt. %. Concentrations greater than about 10 wt. % are difficult to filter. On the other hand, concentrations less than about 0.1 wt. % tend to produce unacceptably low reaction rates.

The concentration of the PMIDA substrate in the feed stream is not critical. Use of a saturated solution of PMIDA substrate in water is preferred, although for ease of operation, the process is also operable at lesser or greater PMIDA substrate concentrations in the feed stream. If the catalyst is present in the reaction mixture in a finely divided form, it is preferred to use a concentration of reactants such that all reactants and the N-(phosphonomethyl)glycine product remain in solution so that the catalyst can be recovered for re-use, for example, by filtration. On the other hand, greater concentrations tend to increase reactor throughput. Alternatively, if the catalyst is present as a stationary phase through which the reaction medium and oxygen source are passed, it may be possible to use greater concentrations of reactants such that a portion of the N-(phosphonomethyl) glycine product precipitates.

It should be recognized that, relative to many commonly-practiced commercial processes, this invention allows for greater temperatures and PMIDA substrate concentrations to be used to prepare N-(phosphonomethyl)glycine while minimizing by-product formation. In the commonly practiced commercial processes using a carbon-only catalyst, it is economically beneficial to minimize the formation of the NMG by-product formed by the reaction of N-(phosphonomethyl)glycine with the formaldehyde by-product. With those processes and catalysts, temperatures of from about 60° to about 90° C. and PMIDA substrate concentrations below about 9.0 wt. % ([mass of PMIDA substrate÷total reaction mass]×100%) typically are used to achieve cost effective yields and to minimize the generation of waste. At such temperatures, the maximum N-(phosphonomethyl)glycine solubility typically is less than about 6.5%. However, with the oxidation catalyst and reaction process of the present invention, the loss of noble metal from the catalyst and catalyst deactivation are minimized and the formaldehyde is more effectively oxidized, thereby allowing for reaction temperatures as high as 180° C. or greater with PMIDA solutions and slurries of the PMIDA substrate. The use of greater temperatures and reactor concentrations permits reactor throughput to be increased, reduces the amount of water that must be removed before isolation of the solid N-(phosphonomethyl)glycine, and reduces the cost of manufacturing N-(phosphonomethyl) glycine. This invention thus provides economic benefits over many commonly-practiced commercial processes.

Normally, a PMIDA substrate concentration of up to about 50 wt. % ([mass of PMIDA substrate÷total reaction mass]×100%) may be used (especially at a reaction temperature of from about 20° to about 180° C.). Preferably, a PMIDA substrate concentration of up to about 25 wt. % is used (particularly at a reaction temperature of from about 60° to about 150° C.). More preferably, a PMIDA substrate concentration of from about 12 to about 18 wt. % is used (particularly at a reaction temperature of from about 100° to about 130° C.). PMIDA substrate concentrations below 12 wt. % may be used, but their use is less economical because less N-(phosphonomethyl)glycine product is produced in each reactor cycle and more water must be removed and energy used per unit of N-(phosphonomethyl)glycine product produced. Lower temperatures (i.e., temperatures less than 100° C.) often tend to be less advantageous because the solubility of the PMIDA substrate and N-(phosphonomethyl)glycine product are both reduced at such temperatures.

The oxygen source for the PMIDA oxidation reaction may be any oxygen-containing gas or a liquid comprising dissolved oxygen. Preferably, the oxygen source is an oxygen-containing gas. As used herein, an "oxygen-containing gas" is any gaseous mixture comprising molecular oxygen which optionally may comprise one or more diluents which are non-reactive with the oxygen or with the reactant or product under the reaction conditions. Examples of such gases are air, pure molecular oxygen, or molecular oxygen diluted with helium, argon, nitrogen, or other non-oxidizing gases. For economic reasons, the oxygen source most preferably is air or pure molecular oxygen.

The oxygen may be introduced by any conventional means into the reaction medium in a manner which maintains the dissolved oxygen concentration in the reaction mixture at the desired level. If an oxygen-containing gas is used, it preferably is introduced into the reaction medium in a manner which maximizes the contact of the gas with the reaction solution. Such contact may be obtained, for example, by dispersing the gas through a diffuser such as a porous frit or by stirring, shaking, or other methods known to those skilled in the art.

The oxygen feed rate preferably is such that the PMIDA oxidation reaction rate is not limited by oxygen supply. If the dissolved oxygen concentration is too high, however, the catalyst surface tends to become detrimentally oxidized, which, in turn, tends to lead to more leaching and decreased formaldehyde activity (which, in turn, leads to more NMG being produced).

Generally, it is preferred to use an oxygen feed rate such that at least about 40% of the oxygen is utilized. More preferably, the oxygen feed rate is such that at least about 60% of the oxygen is utilized. Even more preferably, the oxygen feed rate is such that at least about 80% of the oxygen is utilized. Most preferably, the rate is such that at least about 90% of the oxygen is utilized. As used herein, the percentage of oxygen utilized equals: (the total oxygen consumption rate÷oxygen feed rate)×100%. The term "total oxygen consumption rate" means the sum of: (i) the oxygen consumption rate ("$R_i$") of the oxidation reaction of the PMIDA substrate to form the N-(phosphonomethyl)glycine product and formaldehyde, (ii) the oxygen consumption rate ("$R_{ii}$") of the oxidation reaction of formaldehyde to form formic acid, and (iii) the oxygen consumption rate ("$R_{iii}$") of the oxidation reaction of formic acid to form carbon dioxide and water.

In one embodiment of this invention, oxygen is fed into the reactor as described above until the bulk of PMIDA substrate has been oxidized, and then a reduced oxygen feed rate is used (by, for example, using a reduced feed rate of the oxygen source, or using an oxygen source having a reduced $O_2$ concentration (e.g. air) at a volumetric feed rate which preferably is no greater than the volumetric feed rate of the initial oxygen source). This reduced feed rate preferably is used after about 75% of the PMIDA substrate has been consumed. More preferably, the reduced feed rate is used after about 80% of the PMIDA substrate has been consumed. The reduced oxygen feed rate preferably is maintained for a time of from about 2 to about 40 min., more preferably from about 5 to about 30 min., and most preferably from about 5 to about 20 min. While the oxygen is being fed at the reduced rate, the temperature preferably is maintained at the same temperature or at a temperature less than the temperature at which the reaction was is conducted before the air purge. Likewise, the pressure is maintained at the same pressure or at a pressure less than the pressure at which the reaction was conducted before the air purge. Use of a reduced oxygen feed rate near the end of the PMIDA reaction tends to reduce the amount of residual formaldehyde present in the reaction solution without producing detrimental amounts of AMPA by oxidizing the N-(phosphonomethyl)glycine product.

Reduced losses of noble metal may be observed with this invention if a sacrificial reducing agent is maintained or introduced into the reaction solution. Suitable reducing agents include formaldehyde, formic acid, and acetaldehyde. Most preferably, formic acid, formaldehyde, or mixtures thereof (which, for example, may often advantageously be obtained from waste streams of this process) are used. If small amounts of formic acid, formaldehyde, or a combination thereof are added to the reaction solution, the catalyst will often preferentially effect the oxidation of the formic acid or formaldehyde before it effects the oxidation of the PMIDA substrate, and subsequently will be more active in effecting the oxidation of formic acid and formaldehyde during the PMIDA oxidation. Preferably from about 0.01 to about 5.0 wt. % ([mass of formic acid, formaldehyde, or a combination thereof÷total reaction mass]×100%) of sacrificial reducing agent is added, more preferably from about 0.01 to about 3.0 wt. % of sacrificial reducing agent is added, and most preferably from about 0.01 to about 1.0 wt. % of sacrificial reducing agent is added.

In one embodiment, following the PMIDA oxidation, the catalyst preferably is separated by filtration. The N-(phosphonomethyl)glycine product may then be isolated by precipitation, for example, by evaporation of a portion of the water and cooling. Unreacted formaldehyde and formic acid are recovered from the N-(phosphonomethyl)glycine product mixture in an evaporator to form an overhead vapor stream containing evaporated formaldehyde and formic acid which is condensed and recycled (in whole or in part) back into the reaction mixture for use in subsequent cycles. In this instance, the recycle stream also may be used to solubilize the PMIDA substrate in the subsequent cycles.

Typically, the concentration of N-(phosphonomethyl) glycine in the product mixture may be as great as 40% by weight, or greater. Preferably, the N-(phosphonomethyl) glycine concentration is from about 5 to about 40%, more preferably from about 8 to about 30%, and still more preferably from about 9 to about 15%. Concentrations of formaldehyde in the product mixture are typically less than about 0.5% by weight, more preferably less than about 0.3%, and still more preferably less than about 0.15%.

It should be recognized that the catalyst of this invention has the ability to be reused over several cycles (i.e., it may be used to catalyze multiple batches of substrate), depending on how oxidized its surface becomes with use. Even after the catalyst becomes heavily oxidized, it may be reused by being reactivated. To reactivate a catalyst having a heavily oxidized surface, the surface preferably is first washed to remove the organics from the surface. It then preferably is reduced in the same manner that a catalyst is reduced after the noble metal is deposited onto the surface of the support, as described above.

D. Use of a Supplemental Promoter

In many conventional processes, when it is desirable for a catalyst to contain a promoter, the promoter is pre-deposited onto the catalyst surface by, for example, the promoter deposition techniques described above (this deposition step is often performed by the manufacturer of the catalyst). This promoter deposition step, however, tends to add costs to the catalyst preparation process. To avoid these additional costs, it has been found that the benefits of a promoter (e.g., increased selectivity, activity, and/or catalyst stability) may be obtained by merely mixing a promoter (i.e., a "supplemental promoter") directly with a carbon-supported, noble-metal-containing catalyst (particularly with the reduced catalysts described above). This mixing may, for example, be conducted directly in a reaction mixture where an oxidation reaction being catalyzed by the catalyst is taking place. Alternatively, for example, this mixing may take place separately from the oxidation reaction, such as in a catalyst holding tank.

In accordance with the present invention, it has been discovered that certain metals and/or metal compounds function as supplemental promoters in an oxidation reaction catalyzed by a carbon-supported, noble-metal-containing catalyst. More particularly, it has been found that such supplemental promoters are effective in enhancing the capability of noble metal on carbon catalysts for catalyzing the oxidation of such substrates such as formaldehyde, formic acid, and N-(phosphonomethyl)iminodiacetic acid. The supplemental promoters have been found especially useful in the oxidation of N-(phosphonomethyl)iminodiacetic acid to N-(phosphonomethyl)glycine (glyphosate) wherein they are effective in enhancing catalysis of the desired conversion to glyphosate, the oxidation of by-product formaldehyde to formic acid, and the oxidation of by-product formic acid to carbon dioxide. The supplemental promoters have been found useful both in the in situ oxidation of these by-products in the N-(phosphonomethyl)iminodiacetic acid oxidation reaction zone, and in the oxidation of aqueous formaldehyde and formic acid fractions obtained by distillation or evaporation from the glyphosate reaction mass.

Depending on the application, the supplemental promoter(s) may be, for example, tin, cadmium, magnesium, manganese, ruthenium, nickel, copper, aluminum, cobalt, bismuth, lead, titanium, antimony, selenium, iron, rhenium, zinc, cerium, zirconium, tellurium, sodium, potassium, vanadium, gallium, Ta, Nb, rubidium, cesium, lanthanum, and/or germanium. It is often more preferred for the supplemental promoter(s) to be bismuth, lead, germanium, tellurium, titanium, copper and/or nickel.

In an especially preferred embodiment, the supplemental promoter is bismuth. It has been found in accordance with this invention that the presence of bismuth is especially effective in enhancing the selectivity of a carbon-supported, noble-metal-containing catalyst (particularly the reduced catalyst described above) when it is used to catalyze the oxidation of a PMIDA substrate (e.g., PMIDA or a salt thereof) to form an N-(phosphonomethyl)glycine product (e.g., N-(phosphonomethyl)glycine or a salt thereof). More specifically, it has been found that the presence of bismuth causes an increase in the amount of formic acid byproduct that is catalytically oxidized. In some instances (particularly where the catalyst comprises tin as a catalyst-surface promoter), the presence of bismuth also has been found to cause an increase in the amount of formaldehyde byproduct that is catalytically oxidized. This increased destruction of one or both of these byproducts, in turn, causes less NMG byproduct to be formed (it is believed that this stems from the fact that the formation of each molecule of NMG byproduct requires either (a) two formaldehyde molecules, or (b) a formic acid molecule and a formaldehyde molecule). Further, it has been found that in some instances (particularly where more than one supplemental promoter is used) that the presence of bismuth may also reduce the amount of noble metal that leaches from the carbon support of the catalyst during the oxidation of a PMIDA substrate.

In another preferred embodiment of this invention, tellurium is used as a supplemental promoter. As in the above embodiment incorporating bismuth as a supplemental promoter, it has been found in accordance with this invention that the presence of tellurim is also effective in enhancing the selectivity of a carbon-supported, noble-metal-containing catalyst (particularly the reduced catalyst described above) when it is used to catalyze the oxidation of a PMIDA substrate (e.g., PMIDA or a salt thereof) to form an N-(phosphonomethyl)glycine product (e.g., N-(phosphonomethyl)glycine or a salt thereof). More particularly, applicants have further found that tellurium may increase the activity of the catalyst in the oxidation of PMIDA. Further, applicants have found that noble metal leaching from the carbon support of the catalyst may be reduced during the oxidation of a PMIDA substrate by the presence of tellurium in the reaction medium (particularly when bismuth is also present).

In a most preferred embodiment, two supplemental both bismuth and tellurium are used as supplemental promoters.

The mixing of the supplemental promoter and catalyst preferably is conducted in a liquid medium. As noted above, this mixing may, for example, be conducted directly in a reaction medium where an oxidation reaction being catalyzed by the catalyst is taking place. Where, however, the oxidation reaction is carried out under pressure, the reaction vessel is normally sealed and it is consequently often more preferred to mix the catalyst with the supplemental promoter separately from the reaction vessel, such as in a catalyst holding or recycle tank.

Typically, the supplemental promoter is introduced into the mixing liquid in the form of an inorganic or organic compound containing the supplemental promoter. The promoter-containing compound may be soluble or insoluble in the liquid, but most typically is at least partially soluble. The functional group attached to the supplemental promoter atom is generally not critical (although it preferably is an agronomically acceptable functional group). Typically, for example, suitable compounds include oxides, hydroxides, salts of inorganic hydracids, salts of inorganic oxy-acids, salts of aliphatic or aromatic organic acids, and phenates.

Suitable bismuth-containing compounds, for example, include inorganic or organic compounds wherein the bismuth atom(s) is at an oxidation level greater than 0 (e.g., 2, 3, 4 or 5), most preferably 3. Examples of such suitable bismuth compounds include:

1. Bismuth oxides. These include, for example, BiO, $Bi_2O_3$, $Bi_2O_4$, $Bi_2O_5$, and the like.
2. Bismuth hydroxides. These include, for example, $Bi(OH)_3$ and the like.
3. Bismuth salts of inorganic hydracids. These include, for example, bismuth chloride (e.g., $BiCl_3$), bismuth bromide (e.g., $BiBr_3$), bismuth iodide (e.g., $BiI_3$), bismuth telluride (e.g., $Bi_2Te_3$), and the like. Bismuth halides are typically less preferred because they tend to be corrosive to the process equipment.
4. Bismuth salts of inorganic oxy-acids. These include, for example, bismuth sulphite (e.g., $Bi_2(SO_3)_3.Bi_2O_3.5H_2O$), bismuth sulphate (e.g., $Bi_2(SO_4)_3$), bismuthyl sulfate (e.g., $(BiO)HSO_4$), bismuthyl nitrite (e.g., $(BiO)NO_2.0.5H_2O$), bismuth nitrate (e.g., $Bi(NO_3)_3.5H_2O$, also known as "bismuth nitrate pentahydrate"), bismuthyl nitrate (e.g., $(BiO)NO_3$, also known as "bismuth subnitrate," "bismuth nitrate oxide," and "bismuth oxynitrate"), double nitrate of bismuth and magnesium (e.g., $2Bi(NO_3)_3.3Mg(NO_3)_2.24H_2O$), bismuth phosphite (e.g., $Bi_2(PO_3H)_3.3H_2O$), bismuth phosphate (e.g., $BiPO_4$), bismuth pyrophosphate (e.g., $Bi_4(P_2O_7)_3$), bismuthyl carbonate (e.g., $(BiO)_2CO_3$, also known as "bismuth subcarbonate"), bismuth perchlorate (e.g., $Bi(ClO_4)_3.5H_2O$), bismuth antimonate (e.g., $BiSbO_4$), bismuth arsenate (e.g., $Bi(AsO_4)_3$), bismuth selenite (e.g., $Bi_2(SeO_3)_3$), bismuth titanate (e.g., $Bi_2O_3.2TiO_2$), and the like. These salts also include bismuth salts of oxy-acids derived from transition metals, including, for example, bismuth vanadate (e.g., $BiVO_4$), bismuth niobate (e.g., $BiNbO_4$), bismuth tantalate (e.g., $BiTaO_4$), bismuth chromate (e.g., $Bi_2(CrO_4)$), bismuthyl dichromate (e.g., $(BiO)_2Cr_2O_7$), bismuthyl chromate (e.g., $H(BiO)CrO_4$), double chromate of bismuthyl and potassium (e.g., $K(BiO)CrO_4$), bismuth molybdate (e.g., $Bi_2(MoO_4)_3$), double molybdate of bismuth and sodium (e.g., $NaBi(MoO_4)_2$), bismuth tungstate (e.g., $Bi_2(WO_4)_3$), bismuth permanganate (e.g., $Bi_2O_2(OH)MnO_4$), bismuth zirconate (e.g., $2Bi_2O_3.3ZrO_2$), and the like.

5. Bismuth salts of aliphatic or aromatic organic acids. These include, for example, bismuth acetate (e.g., $Bi(C_2H_3O_2)_3$), bismuthyl propionate (e.g., $(BiO)C_3H_5O_2$), bismuth benzoate (e.g., $C_6H_5CO_2Bi(OH)_2$), bismuthyl salicylate (e.g., $C_6H_4CO_2(BiO)(OH)$), bismuth oxalate (e.g., $(C_2O_4)_3Bi_2$), bismuth tartrate (e.g., $Bi_2(C_4H_4O_6)_3.6H_2O$), bismuth lactate (e.g., $(C_6H_9O_5)OBi.7H_2O$), bismuth citrate (e.g., $C_6H_5O_7Bi$), and the like.
6. Bismuth phenates. These include, for example, bismuth gallate (e.g., $C_7H_7O_7Bi$), bismuth pyrogallate (e.g., $C_6H_3(OH)_2(OBi)(OH)$), and the like.
7. Miscellaneous other organic and inorganic bismuth compounds. These include, for example, bismuth phosphide (e.g., BiP), bismuth arsenide (e.g., $Bi_3As_4$), sodium bismuthate (e.g., $NaBiO_3$), bismuth-thiocyanic acid (e.g., $H_2(Bi(BNS)_5).H_3(Bi(CNS)_6)$), sodium salt of bismuth-thiocyanic acid, potassium salt of bismuth-thiocyanic acid, trimethylbismuthine (e.g., $Bi(CH_3)_3$), triphenylbismuthine (e.g., $Bi(C_6H_5)_3$), bismuth oxychloride (e.g., BiOCl), bismuth oxyiodide (e.g., BiOI), and the like.

In a preferred embodiment, the bismuth compound is a bismuth oxide, bismuth hydroxide, or bismuth salt of an inorganic oxy-acid. More preferably, the bismuth compound is bismuth nitrate (e.g., $Bi(NO_3)_3.5H_2O$), bismuthyl carbonate (e.g., $(BiO)_2CO_3$), or bismuth oxide (e.g., $Bi_2O_3$), with bismuth (III) oxide (i.e., $Bi_2O_3$) being most preferred because it contains no counterion which can contaminate the final reaction product.

Suitable tellurium-containing compounds, for example, include inorganic or organic compounds wherein the tellurium atom(s) is at an oxidation level greater than 0 (e.g., 2, 3, 4, 5 or 6), most preferably 4. Examples of such suitable tellurium compounds include:

1. Tellurium oxides. These include, for example, $TeO_2$, $Te_2O_3$, $Te_2O_5$, $TeO_3$, and the like.
2. Tellurium salts of inorganic hydracids. These include, for example, tellurium tetrachloride (e.g., $TeCl_4$), tellurium tetrabromide (e.g., $TeBr_4$), tellurium tetraiodide (e.g., $TeI_4$), and the like.
3. Tellurium salts of inorganic oxy-acids. These include, for example, tellurious acid (e.g., $H_2TeO_3$), telluric acid (e.g., $H_2TeO_4$ or $Te(OH)_6$) tellurium nitrate (e.g., $Te_2O_4.HNO_3$), and the like.
4. Miscellaneous other organic and inorganic tellurium compounds. These include, for example, dimethyl tellurium dichloride, lead tellurium oxide, tellurium isopropoxide, ammonium tellurate, tellurium thiourea, and the like.

In a preferred embodiment, the tellurium compound is a tellurium oxide or tellurium salt of an inorganic hydracid. More preferably, the tellurium compound is tellurium dioxide (e.g., $TeO_2$), tellurim tetrachloride (e.g., $TeCl_4$), or telluric acid (e.g., $Te(OH)_6$), with tellurium tetrachloride being most preferred.

The preferred amount of the supplemental promoter introduced into the reaction zone depends on, for example, the mass of the carbon-supported, noble-metal-containing catalyst (i.e., the total mass of the carbon support, noble metal, and any other component of the catalyst); mass of the total reaction feed mixture; and the concentration of the oxidation substrate.

In general, the ratio of the mass of the supplemental promoter to the mass of the carbon-supported, noble-metal-containing catalyst charged to the reactor is preferably at least about 1:15,000; more preferably at least about 1:5,000; even more preferably at least about 1:2500; and most preferably at least about 1:1000. Although it is feasible to practice the present invention without detriment to the oxidation reaction when ratios of the mass of supplemental promoter to the mass of the carbon-supported, noble-metal-containing catalyst are as great as about 1:750, about 1:500, about 1:300, and even greater than about 1:50 or 1:40, the preferred lower ratios described above have been found to be effective for most applications, and particularly for the specific embodiments described in the present invention while reducing the amount of supplemental promoter consumed.

The ratio of the mass of the supplemental promoter to the total reaction mass charged to the reactor is preferably at least about 1:1,000,000; more preferably at least about 1:100,000; even more preferably at least about 1:40,000; and most preferably from about 1:40,000 to about 1:15,000. Although ratios greater than 1:8,000 may normally be used without detriment to the oxidation reaction, it is generally preferred for the ratio to be less than 1:8,000 (particularly where bismuth is the supplemental promoter).

The ratio of the mass of the supplemental promoter to the mass of the oxidation substrate (e.g., PMIDA or a salt thereof) charged to the reactor is preferably at least about 1:100,000; more preferably 1:10,000; even more preferably at least about 1:4,000; and most preferably from about 1:4,000 to about 1:2,000. Although ratios greater than 1:1,000 may normally be used without detriment to the oxidation reaction, it is generally preferred for the ratio to be less than 1:1,000 (particularly where bismuth is the supplemental promoter).

Where a particulate noble metal on carbon catalyst is used for the reaction, both the catalyst and the supplemental promoter may be charged to a liquid reaction medium in which the reaction is conducted. For example, in the preparation of N-(phosphonomethyl)glycine (glyphosate), the catalyst and supplemental promoter may be charged to an aqueous reaction medium containing N-(phosphonomethyl) iminodiacetic acid (PMIDA), and oxygen then introduced to the reaction medium for catalytic oxidation of PMIDA to glyphosate. The supplemental promoter may be charged in a mass ratio to the catalyst charge of at least about 1:15,000, preferably at least about 1:5000, more preferably at least about 1:2500, and most preferably at least about 1:1000. As oxidation of PMIDA to glyphosate proceeds, formaldehyde and formic acid by-products are generated. The catalyst is effective to catalyze not only the oxidation of PMIDA but also the further oxidation of formaldehyde to formic acid, and formic acid to carbon dioxide. The presence of the supplemental promoter is effective to enhance the catalytic oxidation of these by-products, especially for the conversion of formic acid to $CO_2$.

Where the oxidation reactions are conducted in a stirred tank reactor in which catalyst is slurried in the reaction medium, the catalyst is separated from the reaction mixture, preferably by filtration, and recycled to the reactor for further oxidation of PMIDA and the aforesaid by-products. Such a stirred tank reactor system may be operated in either a batch or continuous mode. Alternatively, a fixed or fluid catalyst bed can be used. In a continuous process, PMIDA, formaldehyde and formic acid are all oxidized in a continuous reaction zone to which an aqueous reaction medium comprising PMIDA is continuously or intermittently supplied and a reaction mixture comprising glyphosate is continuously or intermittently withdrawn, the supplemental promoter being continuously or intermittently introduced into the reaction zone.

It has been observed that addition of a discrete charge of supplemental promoter to the first batch of series of successive batch reaction cycles is effective to enhance the activity of the catalyst for oxidation of formic acid and formaldehyde throughout the series of reaction cycles, without further addition of supplemental promoter from any external source. It has further been observed that the supplemental promoter is present in the recycled catalyst, apparently having been deposited thereon by adsorption to the noble metal and/or the carbon support. Only a fraction of the supplemental promoter added to the first batch of the series can be found on the catalyst after multiple cycles. However, when supplemental promoter is introduced into the first batch in the amounts described above, the fraction remaining on the catalyst is apparently sufficient for promoting the oxidation of formaldehyde and formic acid throughout the series of batches in which the catalyst recycled from an earlier batch is substantially the sole source of supplemental promoter for the successive batch reaction cycles of the series. It has been found that a single addition of supplemental promoter in a mass ratio to the catalyst of approximately 1:2500 is effective for promotion of by-product oxidation in series of 20 or more, typically 50 or more, more typically over 100, batch reaction cycles. Thereafter, a further discrete charge of supplemental promoter optionally may be added to the reaction medium for a subsequent batch constituting the first of another series of batch oxidation reaction cycles in which the recycle catalyst from an earlier batch of such further series becomes substantially the sole source of promoter for the successive batch reaction cycles of the further series of batch reactions.

Similarly, where supplemental promoter is added to the reaction medium in a continuous stirred tank reactor, addition of supplemental promoter in a single discrete amount is effective to enhance the effectiveness of the catalyst for formaldehyde and formic acid oxidation throughout multiple reactor turnovers of a continuous reaction run. No further addition of supplemental promoter is made until the start of a second reaction run. For this purpose, a reaction run consists of the period of oxidation of formaldehyde and formic acid from the time of any discrete addition of supplemental promoter to the reaction zone until the time of the next succeeding addition of supplemental promoter to the reaction zone, and may typically consist of 50 or more, more typically over 100, turnovers of the working volume of the reactor.

As noted, only a fraction of the supplemental promoter added to the first batch of a cycle remains on the catalyst after multiple cycles of a series of batch reaction runs, or after multiple turnovers of a continuous reaction run. However, the supplemental promoter remains effective to enhance the oxidation of a substrate comprising formaldehyde, or especially formic acid, if the substrate is contacted with the oxidizing agent in a reaction zone which comprises the liquid reaction medium and wherein the mass ratio of supplemental promoter to the catalyst in such reaction zone is at least about 1:200,000, preferably at least about 1:70,000, more preferably at least about 1:30,000, most preferably at least about 1:15,000. Inasmuch as substantially the sole source of supplemental promoter for the reactor may be recycle catalyst, it is further preferred that the supplemental promoter be present on or in the recycle catalyst in the same mass ratios, i.e., at least about 1:200,000, preferably at least about 1:70,000, more preferably at least about 1:30,000, most preferably at least about 1:15,000.

The supplemental promoter content of the reaction zone can also be expressed as a mass ratio to the noble metal component of the catalyst. For example, for a 5% noble metal on carbon catalyst, the ratio of supplemental promoter to noble metal should be at least about 1:10,000, more preferably 1:3500, more preferably 1:1800, most preferably 1:700. These preferences generally prevail over the range of noble metal content of the noble metal on carbon catalyst, which is typically from about 0.5 to 20% noble metal. However, where the noble metal content is relatively high, e.g., approaching 20%, the supplemental promoter may be effective in relatively lower mass ratios to the noble metal component, even as low as 1:40,000.

Where the supplemental promoter is added in a discrete charge at the start of a series of batch reaction cycles, or at the beginning of a continuous reaction run as defined above, it is added in a mass ratio to the noble metal component of the catalyst of at least about 1:750, preferably at least about 1:250, more preferably at least about 1:125, most preferably at least about 1:50. As indicated above, the preferred ratio of supplemental promoter to noble metal may vary with the noble metal content of the catalyst. Thus, e.g., when the noble metal content of the catalyst approaches 20% by weight, the supplemental promoter may be effective when added at a mass ratio to noble metal of 1:3000 or higher, more preferably at least about 1:1000, 1:500 or 1:200.

Periodic discrete additions of supplemental promoter may be advantageous because excessive proportions of supplemental promoter, while maximizing the effectiveness of the catalyst for the oxidation of formaldehyde and formic acid, may retard the oxidation of PMIDA. By adding supplemental promoter only periodically, the proportions of supplemental promoter deposited on the catalyst and present in the reaction zone may decay fairly rapidly to a residual quasi-steady state range wherein the supplemental promoter remains effective to enhance catalytic activity for the oxidation of formaldehyde or formic acid without significantly retarding the rate or extent of oxidation of PMIDA. In fact, while the mass ratio preferences stated above apply to the oxidation of formaldehyde and formic acid, the preferred ratio may fall in an intermediate optimum range for a reaction comprising the conversion of PMIDA to glyphosate. Thus, the optimum supplemental promoter content within the PMIDA oxidation reaction zone, and on the recycle catalyst for such reaction, may be lower than 1:15,000, for example, in a range of 1:65,000 to 1:25,000.

Deposit of supplemental promoter on the surface of a noble metal on carbon catalyst in the reaction medium results in formation of a novel catalyst complex comprising the catalyst and the promoter. The catalyst component of the catalyst complex may further comprise a surface promoter comprising a metal different from the supplemental promoter or, in some instances, comprising the same metal. The supplemental promoter is believed to be deposited by adsorption from the reaction medium, and remains desorbable from the catalyst surface into the catalyst medium. While an operative fraction of residual supplemental promoter resists desorption to remain adhered to the catalyst through multiple reaction cycles (or through an extended run of a continuous reaction system) as explained hereinabove, the supplemental promoter is typically more desorbable than the surface promoter which is applied in the catalyst preparation process.

As described above, the catalyst is prepared in the first instance by depositing noble metal and optionally surface promoter onto a carbon support to form a catalyst precursor, then reducing the catalyst precursor to produce the reaction catalyst. The novel catalyst complex is formed by subsequent deposition of supplemental promoter on the oxidation catalyst, typically by adsorption to the carbon or noble metal surface. Advantageously, the supplemental promoter is mixed with the oxidation catalyst in the reaction medium so that the promoter is deposited from the reaction medium onto the catalyst surface. However, it will be understood that, in the alternative, the supplemental promoter can be premixed with the oxidation catalyst in another liquid medium to form the catalyst complex, after which the catalyst complex may be introduced into the reaction medium for use in conducting the oxidation reaction.

It should be recognized that, depending on the desired effects, more than one supplemental promoter may be used. In addition, each supplemental promoter may come from more than one source. Further, the carbon-supported, noble-metal-containing catalyst may already contain an amount of metal on its surface which is the same metal as the supplemental promoter, such as where (a) the catalyst is manufactured with a such a metal on its surface to act as a catalyst-surface promoter, or (b) the catalyst is a used catalyst which has been recovered from a previous reaction mixture where the metal was present (e.g., as a supplemental promoter).

In a particularly preferred embodiment, the carbon-supported, noble-metal-containing catalyst itself also comprises one or more catalyst-surface promoters on its surface, as described above (see Sections A and B(3)). Where the catalyst is being used in the oxidation of a PMIDA compound and the supplemental promoter is bismuth, it is particularly preferred for the catalyst to contain tin and/or iron (the presence of tin tends to be particularly useful for increasing the oxidation of the formaldehyde byproduct in addition to increasing the oxidation of the formic acid byproduct).

In many instances, after a supplemental promoter and a carbon-supported, noble-metal-containing catalyst have been combined, at least a portion of the supplemental promoter deposits onto the surface of the carbon support and/or noble metal of the catalyst, and is consequently retained by the catalyst. Because the catalyst retains the promoter, the catalyst may typically be recycled for use in catalyzing the oxidation of subsequent amounts of the oxidation substrate (e.g., the catalyst may be used to oxidize additional batches of the oxidation substrate, or may be used in a continuous oxidation process) while still retaining the benefits of the supplemental promoter. And, as the effects of the supplemental promoter decrease over time with use, replenishing amounts of fresh supplemental promoter may periodically be mixed with the catalyst to revive the effects and/or achieve other desired results (e.g., decreased formic acid levels). Where, for example, the catalyst is used in multiple batch reactions, such periodic replenishing may, for example, be conducted after the catalyst has been used in at least about 20 batch oxidation reactions (more preferably after it has been used in at least about 30 batch oxidation reactions, and most preferably after it has been used in at least about 100 or more batch oxidation reactions). Where a catalyst is periodically replenished with fresh supplemental promoter, the mixing for replenishment may be conducted during, or, more preferably, separately from the oxidation reaction being catalyzed by the catalyst.

In a particularly preferred embodiment, a supplemental promoter is mixed with a used catalyst (i.e., a catalyst that has been used in one or more previous oxidation reactions). Typically, the activity and/or desired selectivity of a catalyst decreases with use over several cycles. Thus, for example, the activity of a carbon-supported, noble-metal-containing catalyst for oxidizing byproducts (e.g., formaldehyde and/or formic acid) of the PMIDA oxidation reaction often tends to decrease as the catalyst is used, thereby causing less formic acid and/or formaldehyde to be destroyed, and, consequently, a greater amount of NMG to be produced. Eventually, in fact, this activity will decrease to a level where an unacceptable amount of formic acid and/or formaldehyde is not oxidized, consequently often causing an unacceptable amount of NMG compounds to be produced (i.e., the selectivity of the catalyst for making N-(phosphonomethyl)glycine compounds from PMIDA compounds will decrease to an unacceptable level). Traditionally, when the catalyst activity for oxidizing the byproducts reaches such a point, the catalyst has been deemed unuseable, and, consequently, has either been recycled (i.e., reactivated) through a time-consuming and sometimes costly process, or discarded altogether. It has been discovered in accordance with this invention, however, that such a catalyst can be "revived" (i.e., the selectivity of the catalyst for making the N-(phosphonomethyl)glycine compound can be increased to an acceptable level) by mixing the catalyst with a supplemental promoter, particularly bismuth or tellurium. In other words, the supplemental promoter can be used to modify the catalyst performance and extend the life of the catalyst.

It has been observed that a supplemental promoter (particularly bismuth) may cause a slight decrease in the oxidation rate of PMIDA. In such an instance, the oxidation rate may typically be increased, at least in part, by increasing the amount of oxygen fed into the reacting mixture, maintaining a relatively high oxygen flowrate for an extended period during the reaction, and/or increasing the pressure. Where, however, the oxygen flow is increased, it preferably is not increased to an extent which causes the catalyst surface to become detrimentally over-oxidized. Thus, the increased oxygen feed rate preferably is maintained at a level such that at least about 40% (more preferably at least about 60%, even more preferably at least about 80%, and most preferably at least about 90%) of the fed oxygen is utilized.

E. Oxidation of Unreacted Formic Acid or Formaldehyde

As described above in Sections IV.C. and IV.D., the catalysts and supplemental promoters of the present invention are useful in a variety of liquid phase oxidation reactions including the oxidation of aldehydes to form acids (e.g., the oxidation of formaldehyde to form formic acid) and the oxidation of various acids (e.g., formic acid or acetic acid) to form carbon dioxide and water. Thus, in another particularly preferred embodiment of the present invention, it has been found that the catalysts and supplemental promoters disclosed herein may be employed for the catalytic oxidation of unreacted formic acid and/or formaldehyde recovered from the N-(phosphonomethyl)glycine product mixture produced in a process for the oxidation of N-(phosphonomethyl) iminodiacetic acid as described above.

Considerable quantities of formaldehyde and/or formic acid may be unreacted or generated as a waste stream from the manufacture of N-(phosphonomethyl)glycine by the oxidation of N-(phosphonomethyl)iminodiacetic acid. Typically, excess formaldehyde and/or formic acid are recovered from the N-(phosphonomethyl)glycine product mixture in an evaporator to form an overhead vapor stream comprising formaldehyde, formic acid and/or water. In one embodiment, as described above, the evaporated formaldehyde and formic acid in this overhead vapor stream may be condensed and recycled (in whole or in part) back into the PMIDA reaction mixture for use in subsequent cycles or to solubilize the PMIDA substrate. However, in other cases, it may be necessary or preferred to further treat the condensed formaldehyde or formic acid stream so as to comply with environmental regulations for disposal or to further reduce the costs of obtaining process water. For example, one method for treating an aqueous stream of formaldehyde or formic acid is disclosed in U.S. Pat. No. 5,606,107, which is hereby incorporated by reference.

Figure 2:
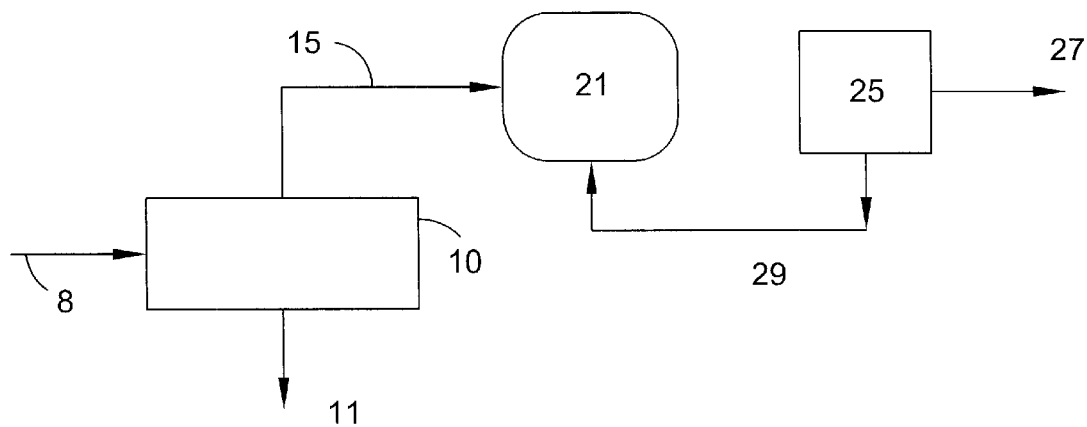
FIG. 2 shows one example of an embodiment that may be used in accordance with this invention for the oxidation of formic acid or formaldehyde contained in an aqueous waste stream generated from the oxidation of N-(phosphonomethyl)iminodiacetic acid for preparing N-(phosphonomethyl)glycine.

Referring now to FIG. 2, one embodiment for the oxidation of formic acid and/or formaldehyde produced as a byproduct from the production of N-(phosphonomethyl) glycine by the oxidation of N-(phosphonomethyl) iminodiacetic acid is illustrated. In this embodiment, for example, reaction product stream 8 from FIG. 1 is passed through an evaporator 10 where essentially all the N-(phosphonomethyl)glycine product 11 is precipitated and a overhead vapor stream 15, which contains evaporated formaldehyde, formic acid, and water is formed. The concentration of formaldehyde and/or formic acid in vapor stream 15 leaving the evaporator 10 may each be as high as about 7500 ppm, with typical average concentrations of formaldehyde of about 6000 ppm and typical average concentrations of formic acid of about 4000 ppm.

Vapor stream 15 is then condensed and the condensate is passed to an evaporator overhead recovery unit comprising an oxidation reactor 21 wherein formic acid and/or formaldehyde are oxidized with oxygen in the presence of a catalyst comprising a noble metal on a particulate carbon support. The oxidation reaction may be carried out in a wide variety of reactor systems including any conventional batch, semi-batch, or continuous reactor system, with a continuous reactor system being preferred. The configuration of the reactor is not critical. Suitable conventional reactor configurations include, for example, stirred tank reactors, fixed bed reactors, trickle bed reactors, fluidized bed reactors, bubble flow reactors, plug flow reactors, and parallel flow reactors, with continuous stirred tank reactors being preferred. Accordingly, it has been found that a single-stage continuous stirred tank reactor is especially effective and such a single-stage continuous reactor system is most preferred.

The oxidation reaction mixture is preferably circulated over a microfiltration unit 25 to separate a purified water stream 27 from the catalyst slurry 29. The purified water stream 27 may be discharged or preferably recycled back to the process for making N-(phosphonomethyl)glycine by the oxidation of N-(phosphonomethyl)iminodiacetic acid. The catalyst slurry 29 is preferably recycled for subsequent use in the oxidation reactor 21. Suitable microfiltration units 25 may include any conventional filtering apparatus for separating a slurry from an aqueous stream, with a preferred microfiltration unit comprising a cross flow filter such as a HyPulse® filter commercially available from Mott Metallurgical Corp. of Farmington, Conn.

In a typical embodiment utilizing a continuous oxidation reactor system, particulate catalyst is charged to the evaporator overhead recovery unit periodically. After about four months the catalyst mass in the oxidation reactor as well as the microfilters need to be replaced due to capacity-reduction caused by gradual microfilter plugging. Generally, this microfilter plugging is a result of an increase in dissolved oxygen in the reactor system. However, in accordance with the present invention, it has been found that the use of a supplemental promoter as described above (particularly bismuth, tellurium, or a combination of bismuth and tellurium) enhances the oxidation of formaldehyde and/or formic acid such that less catalyst has to be charged to the oxidation reactor over the standard four-month operation. Preferably, a supplemental promoter is sufficient to reduce the amount of catalyst charged to the oxidation reactor by about 20%, more preferably about 30% and most preferably about 40%. More importantly, it has been found that the use of a supplemental promoter as described above (particularly bismuth, tellurium, or a combination of bismuth and tellurium) enhances the activity and/or selectivity of the catalyst such that the life of the catalyst may be prolonged, thus reducing the amount of dissolved oxygen in the reactor system such that effective life between changing of the microfiltration unit is also prolonged. More particularly, use of a supplemental promoter in accordance with the present invention is sufficient to prolong the effective catalyst life by at least about is 10%, more preferably by at least about 15%, and most preferably by at least about 20%.

V. EXAMPLES

The following examples are simply intended to further illustrate and explain the present invention. This invention, therefore, should not be limited to any of the details in these examples.

Example 1

Measuring Pore Volume of Carbon Support

A Micromeritics ASAP 2000 surface area and pore volume distribution instrument was used to acquire the data. Total surface area determination involves exposing a known weight of a solid to some definite pressure of a non-specific adsorbate gas at a constant temperature, e.g., at the temperature of liquid nitrogen, $-196°$ C. During equilibration, gas molecules leave the bulk gas to adsorb onto the surface which causes the average number of molecules in the bulk gas to decrease which, in turn, decreases the pressure. The relative pressure at equilibrium, p, as a fraction of the saturation vapor pressure, $p_o$, of the gas is recorded. By combining this decrease in pressure with the volumes of the vessel and of the sample, the amount (i.e., the number of molecules) of gas adsorbed may be calculated by application of the ideal gas laws. These data are measured at relative pressures ($p/p_o$) of approximately 0.1 to 0.3 where the Brunauer, Emmett and Teller (BET) equation for multilayer adsorption typically applies. With the number of adsorbed gas molecules known, it is possible to calculate the surface area using the "known" cross-sectional area of the adsorbate. For cases where only physical adsorption due to Van der Waals forces occurs (i.e., Type I Langmuir isotherms) the determination of surface area from the observed changes in pressure is accomplished using the BET equation. Pore size and pore size distributions are calculated by obtaining relative pressure data approaching $p/p_o=1$, i.e., in the regime where multi-layer adsorption and capillary condensation occur. By applying the Kelvin equation and methods developed by Barrett, Joyner and Halenda (BJH), the pore volume and area may be obtained.

Example 2

High-temperature Deoxygenation of a Carbon Support

The high-temperature deoxygenation procedures described in the following examples may be used with any carbon support to produce a deoxygenated carbon support.

Single-Step Hiqh-Temperature Deoxygenation #1 Using $NH_3/H_2O$ Gas

An activated carbon support (2.5 g) was placed into a 1.9 cm I.D.×40.6 cm length quartz tube. The tube was connected to a gas stream resulting from sparging a 70 to 100 ml/min. $N_2$ stream through a 70° C., 10% $NH_4OH$ aqueous solution. The quartz tube then was placed into a preheated 30.5 cm tubular furnace and pyrolyzed at 930° C. for 60 min. and then cooled to room temperature under a dry $N_2$ atmosphere without contacting any air.

Single-Step High-Temperature Deoxygenation #2 Using $NH_3/H_2O$ Gas

An activated carbon support (3.55 g) was placed into a 1.9 cm I.D.×35.6 cm long quartz tube. The tube was connected to streams of 50 ml/min. of $NH_3$ gas and 89 ml/min. of steam and then placed into a preheated 30.5 cm tubular furnace and pyrolyzed at 930° C. for 30 minutes. The tube subsequently was cooled to room temperature under a dry $N_2$ atmosphere without any contact with air.

To show the advantages of deoxygenating the carbon support before dispersing the noble metal onto the surface of the support, the performances of the following two catalysts were compared: one having a carbon support, which was deoxygenated using the above treatment before platinum was dispersed onto its surface; and one having an SA-30 carbon support (Westvaco Corp. Carbon, Department Covington, Va.) which was used as received from Westvaco. Platinum was dispersed onto the surfaces of the carbon supports using the technique described in Example 3 below. The catalysts then were reduced. In one experiment, the catalysts were reduced using $NaBH_4$ (See Example 12 for protocol). In a second experiment, the catalysts were reduced by heating them in 20% $H_2$ and 80% argon for 8 hours at 640° C.

The reduced catalysts were used to catalyze the oxidation of PMIDA to N-(phosphonomethyl)glycine (i.e., "glyphosate") using the reaction conditions set forth in Example 5. Table 1 shows the results. Use of the deoxygenated carbon support resulted in smaller CO desorption values, less noble metal leaching, higher formaldehyde activity, and shorter reaction times.

TABLE 1

Effect of Deoxygenating the Carbon Support before Dispersing Noble Metal onto Its Surface

| Deoxygenation treatment | CO desorption from carbon support (mmole/g) | Reduction | Pt in soln. (µg/g glyph. prod.) | $CH_2O$ (mg/g glyph. prod.) | Reaction time[1] (min.) |
|---|---|---|---|---|---|
| Single-step high-temperature deoxygenation #2 | 0.23 | $NaBH_4$ Reduced (Ex. 12) | 8.6 | 28.5 | 35.1 |

TABLE 1-continued

Effect of Deoxygenating the Carbon Support before Dispersing Noble Metal onto Its Surface

| Deoxygenation treatment | CO desorption from carbon support (mmole/g) | Reduction | Pt in soln. (µg/g glyph. prod.) | $CH_2O$ (mg/g glyph. prod.) | Reaction time[1] (min.) |
|---|---|---|---|---|---|
| SA-30, used as received | 1.99 | same | 54.3 | 43.1 | 62.7 |
| Single-step high-temperature deoxygenation #2 | 0.23 | 8 hrs at 640° C. in 20% H2, 80% Ar | 4.8 | 15.6 | 29.8 |
| SA-30, used as received | 1.99 | same | 31 | 19.7 | 50.7 |

[1]When ≧98% of the PMIDA has been consumed.

Example 3

Depositing Platinum onto the Surface of a Carbon Support

Twenty grams of NUCHAR activated carbon SA-30 (Westvaco Corp. Carbon, Department Covington, Va.) was slurried in 2 L of water for 2 hours. Then, 2.81 grams of $H_2PtCl_6$ dissolved in about 900 ml of water was added dropwise over a period of 3 to 4 hours. After the $H_2PtCl_6$ solution was completely added, the slurry was stirred for 90 more minutes. The pH of the slurry then was readjusted to 10.5 using NaOH, and stirred for 10 to 14 more hours. The resulting slurry was filtered and washed with water until the filtrate reached a constant conductivity. The wet cake was dried at 125° C. under vacuum for 10 to 24 hours. This material produced 5% platinum on carbon upon reduction.

It should be recognized that the above procedure may be used to deposit platinum onto the surface of other carbon supports as well.

Example 4

High-temperature Hydrogen Reduction of a Carbon Support

Approximately 5.8 g of a dried, unreduced catalyst consisting of 5% platinum on a NUCHAR SA-30 carbon support (Westvaco Corp., Carbon Department, Covington, Va.) was dehydrated in-situ at 135° C. in argon for one hour before being reduced at 640° C. with 20% $H_2$ in argon for 11 hours. Upon cooling to room temperature under 20% $H_2$ in argon, the catalyst was ready to use.

It should be recognized that the above procedure may be used to heat other carbon supports as well.

Example 5

Use of the Catalyst to Oxidize PMIDA to N-(Phosphonomethyl)glycine

This example demonstrates the use of high-temperature gas-phase reduction to improve catalyst performance.

An Aldrich catalyst consisting of 5% platinum on an activated carbon support (catalog No. 20,593-1, Aldrich Chemical Co., Inc., Milwaukee, Wis.) was heated at 640° C. for 4–6 hours in the presence of 20% $H_2$ and 80% argon.

Subsequently, it was used to catalyze the oxidation of PMIDA to Glyphosate. Its performance was compared to the performance of a sample of the Aldrich catalyst which was used as received from Aldrich.

The PMIDA oxidation reaction was conducted in a 200 ml glass reactor using 11.48 g of PMIDA, 0.5% catalyst (dry basis), a total reaction mass of 140 g, a temperature of 90° C., a pressure of 50 psig, a stir rate of 900 rpm, and an oxygen flow rate of 100 ml/min.

Table 2 shows the results. The high-temperature hydrogen-reduced catalyst had less leaching, better formaldehyde activity, and produced less NMG. Also, reaction time was shortened by 30% when the high-temperature hydrogen-reduced catalyst was used.

TABLE 2

PMIDA Oxidation Results for 5% Pt on Activated Carbon (Aldrich Cat. No. 20, 593-1)

| Catalyst | As Received | High-Temp., $H_2$ Reduced |
|---|---|---|
| PMIDA (%) | 0.4619 | 0.4430 |
| N-(phosphonomethyl)glycine (%) | 5.58 | 5.54 |
| $HCO_2H$ (mg/g glyph. prod.) | 46.99 | 35.87 |
| $CH_2O$ (mg/g glyph. prod.) | 32.96 | 14.60 |
| NMG (mg/g glyph. prod.) | 3.58 | 1.32 |
| AMPA (ppm) | 172.5 | 182.0 |
| End Point (mm.) | 64.67 | 44.17 |
| Pt in soln. (µg/g glyph. prod.) | 32.26 | 10.50 |
| % of Pt Lost | 0.72 | 0.232 |

Example 6

Further Examples Showing Use of Catalyst to Oxidize PMIDA to N-(Phosphonomethyl)glycine This example demonstrates using the high-temperature, gas-phase reduction treatment and ammonia washing to improve catalyst performance.

The performances of six catalysts in catalyzing the PMIDA oxidation were compared. These catalysts were: (a) a catalyst consisting of 5% platinum on an activated carbon support (Catalog No. 33,015-9, Aldrich Chemical Co., Inc., Milwaukee, Wis.); (b) the catalyst after being washed with ammonia (ammonia washing was conducted using the same technique described in Example 10 except that the pH of the catalyst slurry was adjusted to and maintained at 11.0 rather than 9.5); (c) the catalyst after being heated at 75° C. in 20% $H_2$ and 80% argon for 4–6 hours (GPR @ 75° C.); (d) the catalyst after being heated at 640° C. for 4–6 hours in the presence of 20% $H_2$ and 80% argon (GPR @ 640° C.); and (e) two catalysts after being washed with ammonia and then heated at 640° C. for 4–6 hours in the presence of 20% $H_2$ and 80% argon. The PMIDA oxidation reaction conditions were the same as in Example 5.

Table 3 shows the results. The untreated catalyst showed relatively high leaching and poor formaldehyde activity. High-temperature gas-phase reduction at 640° C. in the presence of $H_2$ leads to the greatest decrease in leaching and increase in formaldehyde activity. Heating the catalyst at 75° C. in 20% $H_2$ at 75° C. decreased leaching to a lesser extent, but did not enhance the formaldehyde activity.

TABLE 3

PMIDA Oxidation Results for 5% Pt on Activated Carbon (Aldrich Cat. No. 33, 015-9)

| Catalyst | As-received | $NH_3$ wash w/o GPR[1] | GPR@ 75° C. | GPR@ 640° C. | $NH_3$ wash + GPR@ 640° C. | $NH_3$ wash + GPR@ 640° C. |
|---|---|---|---|---|---|---|
| PMIDA (%) | ND | ND | ND | 0.097 | 0.083 | ND |
| Glyphosate (%) | 5.87 | 5.65 | 5.81 | 5.89 | 5.85 | 5.91 |
| $HCO_2H$ (mg/g glyph. prod.) | 43.46 | 43.65 | 38.97 | 42.14 | 46.91 | 52.12 |
| $CH_2O$ (mg/g glyph. prod.) | 19.39 | 22.73 | 19.85 | 13.78 | 15.70 | 17.61 |
| NMG (mg/g glyph. prod.) | 1.27 | 0.89 | 0.89 | 1.00 | 1.31 | 1.68 |
| AMPA (ppm) | 149.4 | 147.6 | 134.6 | 349.8 | 324.8 | 283.8 |
| End Point (min.) | 39.33 | 44.33 | 38 | 31.42 | 34.33 | 33.33 |
| Pt in soln. (μg/g glyph. prod.) | 42.59 | 40.71 | 27.54 | 5.26 | 5.30 | 4.23 |
| % of Pt Lost | 1 | 0.92 | 0.64 | 0.12 | 0.12 | 0.1 |

[1]"GPR" means reduction in $H_2$
[2]"ND" means none detected.

In the next experiment, five catalysts were analyzed while catalyzing the PMIDA oxidation. These catalysts were: (a) a catalyst consisting of 5% platinum on NUCHAR SA-30 (Westvaco Corp., Carbon Department, Covington, Va.); (b) the catalyst after being treated with $NaBH_4$ (see Example 12 for protocol); (c) the catalyst after being heated at 75° C. in 20% $H_2$ and 80% argon for 4–6 hours (GPR@75° C.); (d) the catalyst after being heated at 640° C. in 20% $H_2$ and 80% argon for 4–6hours (GPR @ 640° C.); (e) the catalyst after being washed with ammonia (using the same technique described in Example 10) and then heated at 640° C. in 20% $H_2$ and 80% argon for 4–6hours. The reaction conditions were the same as those in Example 5.

Table 4 shows the results. The untreated catalyst showed relatively high platinum leaching and low formaldehyde activity. The catalyst also showed high leaching and low formaldehyde activity after being treated with $NaBH_4$, as did GPR @ 75° C. In contrast, GPR @ 640° C. showed a greater formaldehyde activity and less leaching.

TABLE 4

PMIDA Oxidation Results Using 5% Pt on NUCHAR SA-30

| Catalyst | Un-reduced | $NaBH_4$ red. | GPR @ 75° C. | GPR @ 640° C. | $NH_3$ wash + GPR @ 640° C. |
|---|---|---|---|---|---|
| Glyphosate (%) | 2.50 | 5.71 | 4.92 | 5.17 | 5.19 |
| $HCO_2H$ (mg/g glyph. prod.) | 59.56 | 51.14 | 57.85 | 30.85 | 38.21 |
| $CH_2O$ (mg/g glyph. prod.) | 115.28 | 43.13 | 48.52 | 19.67 | 20.79 |
| NMG (mg/g glyph. prod.) | 1.64 | 2.17 | 6.41 | 0.37 | 1.73 |
| AMPA (ppm) | 58.16 | 193.9 | 174.0 | 138.5 | 156.3 |
| End point (min.) | 62.67 | 62.67 | 70.67 | 50.67 | 59.33 |
| Pt in soln. (μg/g glyph. prod.) | 84.00 | 54.29 | 81.30 | 30.95 | 19.27 |
| % of Pt Lost | 0.84 | 1.24 | 1.6 | 0.64 | 0.4 |

Example 7

Effect of C/O and O/Pt Ratios at the Surface of the Catalyst

The carbon atom to oxygen atom ratio and the oxygen atom to platinum atom ratio at the surfaces of various fresh catalysts were analyzed using a PHI Quantum 2000 ESCA Microprobe Spectrometer (Physical Electronics, Eden Prairie, Minn.). The surface analysis was performed by electron spectroscopy for chemical analysis ("ESCA") with the instrument in a retardation mode with the analyzer at fixed band pass energy (constant resolution). The analysis entails irradiation of the sample with soft X-rays, e.g., Al $k_{60}$ (1486.6 eV), whose energy is sufficient to ionize core and valence electrons. The ejected electrons leave the sample with a kinetic energy that equals the difference between the exciting radiation and the "binding energy" of the electron (ignoring work function effects). Because only the elastic electrons, i.e., those that have not undergone energy loss by any inelastic event, are measured in the photoelectron peak, and because the inelastic mean free path of electrons in solids is short, ESCA is inherently a surface sensitive technique. The kinetic energy of the electrons is measured using an electrostatic analyzer and the number of electrons are determined using an electron multiplier. The data are presented as the number of electrons detected versus the binding energy of the electrons. ESCA survey spectra were taken using monochromatic Al $k_\alpha$ x-rays for excitation of the photoelectrons with the analyzer set for a 117 eV band pass energy. The X-ray source was operated at 40 watts power and data were collected from the 200 μm spot on the sample being irradiated. These conditions give high sensitivity but low energy resolution. The spectra were accumulated taking a 1.0 eV step size across the region from 1100 eV to 0 eV and co-adding repetitive scans to achieve acceptable signal/noise in the data. The elements present were identified and quantified using the standard data processing and analysis procedures provided with the instrumentation by the vendor. From the relative intensities of the photoelectron peaks, the relative atomic concentrations of the elements Pt/C/O are obtained. ESCA analysis is generally cited as having a precision of ±20% using tabulated response factors for a particular instrument configuration.

Table 5 shows the C/O and O/Pt ratios at the surface of each fresh catalyst, and the amount of leaching for each of the catalysts during a single-cycle PMIDA oxidation reaction.

TABLE 5

Effects of C/O and O/Pt Ratios During PMIDA Oxidation[1]

| Catalyst | Reduction Treatment After Depositing Noble Metal | C/O Ratio | O/Pt Ratio | Pt in Soln. (μg/g)[2] | $CH_2O$ (mg/g)[3] |
|---|---|---|---|---|---|
| 5% Pt on deoxygenated carbon[5] | $NaBH_4$ Reduced | 23.7 | 3 | ND[4] | |
| same | Pt(II)[6] | 35.3 | 17 | 1.2 | 24.44 |
| same | 640° C./9 hr/10% $H_2$ $NaBH_4$ Reduced | 21.1 | 3 | 6.9 | |
| Aldrich Cat. No. 33015-9 | 640° C./6 hr/20% $H_2$ | 67.9 | 3 | 5.2 | 13.78 |
| same | 75° C./6 hr/20% $H_2$ | 13.4 | 10 | 27.5 | 19.85 |
| same | Used as Received | 13.3 | 10 | 42.6 | 19.39 |
| Aldrich Cat. #20593-1 | 640° C./6 hr/20% $H_2$ $NH_3$ wash/pH = 11 | 45.2 | 7 | 10.5 | 21.90 |
| same | 640° C./6 hr/20% $H_2$ | 37.7 | 10 | 10.5 | 14.60 |
| same | Used as Received | 9.1 | 26 | 32.3 | 32.96 |
| 5% Pt on SA-30 Westvaco carbon | 640° C./7 hr/20% $H_2$ $NH_3$ wash/pH = 9.5 | 67.7 | 8 | 19.3 | 20.79 |

TABLE 5-continued

Effects of C/O and O/Pt Ratios During PMIDA Oxidation[1]

| Catalyst | Reduction Treatment After Depositing Noble Metal | C/O Ratio | O/Pt Ratio | Pt in Soln. (μg/g)[2] | $CH_2O$ (mg/g)[3] |
|---|---|---|---|---|---|
| same | 640° C./8 hr/20% $H_2$ | 63.3 | 8 | 30.9 | 19.67 |
| same | 75° C./7 hr/20% $H_2$ | 13.2 | 32 | 81.3 | 48.52 |

[1]The reaction conditions were the same as those used in Example 5.
[2]μg Pt which leached into solution per gram Glyphosate produced.
[3]mg formaldehyde per gram Glyphosate produced.
[4]"ND" means none detected.
[5]The carbon support was deoxygenated using the singe-step high-temperature deoxygenation technique #2 described in Example 2.
[6]The Pt was deposited using diamminedinitrito P(II) as described in Example 11.

Example 8

Analysis of Catalyst Surface using Thermogravimetric Analysis with in-line Mass Spectroscopy (TGA-MS)

The concentration of oxygen-containing functional groups at the surfaces of various fresh catalysts was determined by thermogravimetric analysis with in-line mass spectroscopy (TGA-MS) under helium. To perform this analysis, a dried sample (100 mg) of fresh catalyst is placed into a ceramic cup on a Mettler balance. The atmosphere surrounding the sample then is purged with helium using a flow rate 150 ml/min. at room temperature for 10 minutes. The temperature subsequently is raised at 10° C. per minute from 20 to 900° C., and then held at 900° C. for 30 minutes. The desorptions of carbon monoxide and carbon dioxide are measured by an in-line mass spectrometer. The mass spectrometer is calibrated in a separate experiment using a sample of calcium oxalate monohydrate under the same conditions.

Table 6 shows the amount of carbon monoxide desorbed per gram of each catalyst using TGA-MS, and the amount of leaching for each of the catalysts during a single-cycle PMIDA oxidation reaction using the same reaction conditions as in Example 5. As Table 6 shows, leaching tends to decrease as the amount of CO desorption decreases, and is particularly low when the desorption is no greater than 1.2 mmole/g (mmole CO desorbed per gram of catalyst).

TABLE 6

Effects of Oxygen-Containing Functional Groups Which Desorb from Catalyst Surface as CO during TGA-MS

| Catalyst | Reduction Treatment | TGA-MS (mmole/g)[1] | Pt in Soln. (μg/g)[2] | $CH_2O$ (mg/g)[3] |
|---|---|---|---|---|
| Aldrich Cat. #33015-9 | 640° C./6 hr/20% $H_2$ | 0.41 | 5.2 | 13.78 |
| same | 640° C./6 hr/20% $H_2$ $NH_3$ wash/pH = 9.5 | 0.38 | 5.3 | 15.70 |
| same | 75° C./6 hr/20% $H_2$ | 1.87 | 27.5 | 19.85 |
| same | $NH_3$ wash/pH = 9.5 | 1.59 | 40.7 | 22.73 |
| same | Used as Received | 1.84 | 42.6 | 19.39 |

[1]mmole of CO per gram of catalyst
[2]μg of noble metal which leaches into solution per gram of Glyphosate produced
[3]mg of formaldehyde per gram of Glyphosate produced

Example 9

Effect of Temperature During High-temperature Gas-phase Reduction

This example demonstrates the effects of using various temperatures when heating the catalyst in the presence of a reducing agent.

An unreduced catalyst having 5% platinum on an activated carbon support (which was deoxygenated using the single-step high-temperature deoxygenation technique #2 described in Example 2 before the platinum is deposited) was heated at various temperatures in 10% $H_2$ and 90% argon for about 2 hours. The catalyst then was used to catalyze the PMIDA oxidation reaction. The reaction was conducted in a 250 ml glass reactor using 5 g PMIDA, 0.157% catalyst (dry basis), 200 g total reaction mass, a temperature of 80° C., a pressure of 0 psig, and an oxygen flow rate of 150 ml/min.

The results are shown in Table 7. Increasing the reduction temperature from 125° C. to 600° C. reduces the amount of noble metal leaching and increases the formaldehyde oxidation activity during the oxidation reaction of PMIDA into Glyphosate.

TABLE 7

Effects of Reduction Temperature

| Reduction Temperature (° C.) | Pt in Soln. (normalized[1]) | $CH_2O$ (normalized[2]) | C/O Ratio | O/Pt Ratio |
|---|---|---|---|---|
| 125 | 1.00 | 0.41 | 26 | 13 |
| 200 | 0.44 | 0.80 | 27 | 14 |
| 400 | 0.18 | 0.93 | 42 | 10 |
| 500 | 0.14 | 0.95 | 32 | 14 |
| 600 | 0.06 | 1.00 | 40 | 11 |

[1]A normalized value of 1.00 corresponds to the highest amount of Pt observed in solution during this experiment.
[2]A normalized value of 1.00 corresponds to the highest formaldehyde activity during this experiment.

Example 10

Washing the Catalyst with Ammonia

An unreduced catalyst (6.22 g) consisting of 5% platinum on an activated carbon support (which was deoxygenated using the single-step high-temperature deoxygenation technique #2 described in Example 2 before the platinum was deposited onto the support) was slurried in 500 ml of water for 30 minutes. Afterward, the pH of the slurry was adjusted to 9.5 with diluted aqueous ammonia, and the slurry was stirred for one hour, with aqueous ammonia being periodically added to maintain the pH at 9.5. The resulting slurry was filtered and washed once with about 300 ml of water. The wet cake then was dried at 125° C. under vacuum for about 12 hours. This catalyst was heated at 640° C. for 11 hours in 10% $H_2$ and 90% argon, and then compared with two other catalysts consisting of 5% platinum on NUCHAR activated carbon: (a) one reduced at room temperature with $NaBH_4$ (see Example 12 for protocol), and (b) one heated at 640° C. in 10% $H_2$ and 90% argon for 11 hours. The reactions were the same as those in Example 5.

The results are shown in Table 8. Platinum leaching was the lowest with the catalyst which was washed with ammonia before high-temperature hydrogen reduction.

TABLE 8

Effects of Ammonia Washing

| Catalyst | $CH_2O$ (mg/g)[1] | $HCO_2H$ (mg/g) | NMG (mg/g) | Pt in soln. (μg/g) |
|---|---|---|---|---|
| $NH_3$-washed, High-Temp., $H_2$-reduced | 10.62 | 28.79 | 0.83 | 0.50 |
| High-temp., $H_2$-reduced | 14.97 | 27.82 | 1.38 | 4.64 |
| Room-Temp., $NaBH_4$-reduced | 28.51 | 70.16 | 2.59 | 8.64 |

[1]These quantities are per gram Glyphosate produced.

Example 11

Use of a Less Oxidizing Noble Metal Precursor

Platinum was deposited on an activated carbon support using diamminedinitrito platinum (II). Approximately 20 g of an activated carbon support was deoxygenated using the single-step high-temperature deoxygenation technique #2 described in Example 2. Next, it was slurried in 2 L of water for 2 hours. Approximately 51.3 g of a 3.4% solution of diamminedinitrito platinum (II), diluted to 400 g with water, then was added dropwise over a period of 3–4 hours. After addition was complete, stirring was continued for 90 more minutes. The pH was re-adjusted to 10.5 by adding diluted aqueous NaOH, and stirring was conducted for 10–14 more hours. The slurry then was filtered and washed with a plentiful amount of water until the filtrate reached constant conductivity. The wet cake was dried at 125° C. under vacuum for 10–24 hours. The resulting catalyst was heated at 640° C. for 4–6hours in 10% $H_2$ and 90% argon.

A control was prepared using $H_2PtCl_6$ to deposit platinum onto the same carbon. The control was heated under the same conditions as the catalyst prepared using diamminedinitrito platinum (II).

These catalysts were compared while catalyzing the PMIDA oxidation reaction. The reaction conditions were the same as those in Example 5.

The catalyst prepared using diamminedinitrito platinum (II) showed less leaching than the control. Only 1.21 μg platinum per gram of Glyphosate produced leached into solution, which was about three times better than the control.

Example 12

Reducing the Catalyst Surface using $NaBH_4$

The purpose of this example is to demonstrate the effects of reducing the catalyst using $NaBH_4$.

Approximately 5 g of an activated carbon support (which was deoxygenated using the single-step high-temperature deoxygenation technique #2 described in Example 2 before the platinum was deposited onto the support) was slurried with 85 ml of distilled water in a 250 ml round bottom flask. The slurry was stirred in a vacuum for about 1 hour. Next, 0.706 g of $H_2PtCl_6$ in 28 ml of distilled water was added to the slurry at a rate of about 1 ml per 100 seconds with the vacuum still being applied. After stirring overnight in the vacuum, the reactor was brought to atmospheric pressure by admitting a flow of $N_2$. After allowing the slurry to settle, approximately 30 ml of colorless supernatant was decanted. The remaining slurry was transferred to a 100 ml Teflon round bottom. At this point, the pH was adjusted to 12.2 with 0.3 g of NaOH. Then, 2.3 ml of $NaBH_4$ in 14 M NaOH was added at 0.075 ml/min. Subsequently, the resulting slurry was stirred for one hour, filtered, and washed five times with 50 ml of distilled water. The catalyst then was dried at 125° C. and 6 mmHg for 12 hours.

The resulting catalyst was used to catalyze the PMIDA oxidation. The reaction was conducted in a 300 ml stainless steel reactor using 0.5% catalyst, 8.2% PMIDA, a total reaction mass of 180 g, a pressure of 65 psig, a temperature of 90° C., an agitation rate of 900 rpm, and an oxygen feed rate of 72 ml/min.

A control experiment also was conducted at the same reaction conditions using 5.23% platinum on an activated carbon support (which was deoxygenated using the single-step high-temperature deoxygenation technique #2 described in Example 2 before the platinum was deposited onto the support).

Table 9 shows the results using the $NaBH_4$-reduced catalyst, and Table 10 shows the results of the control experiment. Reducing with $NaBH_4$ reduced the amount of noble metal leaching. It also reduced the amount of formaldehyde and NMG after a period of use.

TABLE 9

Results Using Catalyst Treated with $NaBH_4$

| Run # | 1 | 2 | 3 | 4 | 5 | 6 |
|---|---|---|---|---|---|---|
| Glyphosate (%) | 5.79 | 5.81 | 5.75 | 5.74 | 5.79 | 5.77 |
| PMIDA (%) | 0.23 | 0.08 | 0.13 | 0.22 | 0.13 | 0.13 |
| $CH_2O$ (mg/g glyph) | 28.5 | 31.5 | 47.8 | 38.8 | 41.6 | 45.8 |
| $HCO_2H$ (mg/g glyph) | 70.2 | 90.5 | 100.5 | 96.6 | 98.8 | 99.0 |
| AMPA/MAMPA (%) | 0.02 | 0.01 | 0.01 | 0.01 | 0.01 | 0.01 |
| NMG (mg/g glyph) | 2.6 | 3.6 | 3.6 | 4.2 | 4.7 | 4.7 |
| Pt in Soln. (μg/g glyph.) | 8.64 | 8.60 | 5.22 | 6.96 | 6.91 | 5.20 |
| % of Pt Lost | 0.20 | 0.20 | 0.12 | 0.16 | 0.16 | 0.12 |

TABLE 10

Results Using Catalyst which was not treated with $NaBH_4$

| Run # | 1 | 2 | 3 | 4 | 5 | 6 |
|---|---|---|---|---|---|---|
| Glyphosate (%) | 5.36 | 5.63 | 5.37 | 5.50 | 5.56 | 5.59 |
| PMIDA (%) | 0.18 | 0.15 | 0.25 | 0.21 | 0.18 | 0.23 |
| $CH_2O$ (%) | 20.9 | 23.6 | 38.4 | 44.2 | 47.7 | 58.3 |
| $HCO_2H$ (%) | 27.8 | 63.8 | 96.5 | 98.4 | 102.2 | 102.0 |
| AMPA/MAMPA (%) | 0.04 | 0.02 | 0.04 | 0.02 | 0.02 | 0.03 |
| NMG (mg/g glyph) | 1.5 | 3.0 | 5.4 | 6.9 | 10.6 | 7.3 |
| Pt in Soln (μg/g glyph.) | 63.6 | 62.2 | 44.7 | 34.6 | 28.8 | 28.6 |
| % of Pt Lost | 1.30 | 1.34 | 0.92 | 0.73 | 0.61 | 0.61 |

Example 13

Use of Bismuth as a Catalyst-surface Promoter

A 500 g solution was prepared consisting of $10^{-3}$ M $Bi(NO_3)_3 \cdot 5H_2O$ in $10^{-3}$ M formic acid solution. This solution was added to 500 g of a 5% formaldehyde solution containing 6.0 g of 5% platinum on an activated carbon support. The solution was stirred at 40° C. under $N_2$ overnight and then filtered with a Buchner funnel. An aliquot was dried and subsequently analyzed by X-ray fluorescence. The catalyst had a loss on drying ("LOD") of 63%. The dry catalyst was found to contain approximately 3% bismuth and 4% platinum.

The following were placed into a 300 ml stainless steel autoclave: 16.4 g of PMIDA; 4.16 g of an activated carbon catalyst, 0.68 g of the above catalyst consisting of 3% bismuth/4% platinum on its surface, and 179.4 g of water. The reaction was conducted at a pressure of 65 psig, a temperature of 90° C., an oxygen flow rate of 38 ml/min., and a stir rate of 900 rpm. The reaction was allowed to proceed until the PMIDA was depleted. The product solution was separated from the catalyst via filtration and the solution was neutralized with 6 g of 50% NaOH solution. The catalyst was recycled with no purge through 5 runs. Analysis of the product solution was done for each run. Two controls also were conducted in the same manner as above except that the 0.68 g of the Bi/Pt/carbon catalyst was omitted.

The results are shown in Table 11. The runs having the Bi/Pt/carbon catalyst produced lower levels of formaldehyde, formic acid, and NMG in the product.

dissolved in 75 ml of water. The solution was added dropwise to the carbon slurry. After all the solution was added, the slurry was stirred for two hours. The slurry then was filtered and washed with a plentiful amount of water until the filtrate reached a constant conductivity. The wet cake was dried at 125° C. under vacuum to give 1% iron on carbon. Following drying, the 1% iron on carbon was calcined in argon at about 500° C. for 8 hours.

To deposit platinum onto the surface of the carbon support, 2.5 g of the 1% iron on carbon first was slurried in about 180 ml of water. Then, 0.355 g of $H_2PtCl_6$ was dissolved in about 70 ml of water and added dropwise. After all the solution was added, the slurry was stirred for three more hours. The pH then was adjusted to about 10.0 with diluted NaOH and stirring was continued for a few more

TABLE 11

PMIDA Oxidation Results Using Pt/Bi/C Catalyst

|  | CONTROL #1 | CONTROL #2 | 1ST RUN | 2ND RUN | 3RD RUN | 4TH RUN | 5TH RUN |
|---|---|---|---|---|---|---|---|
| Glyphosate (%) | 5.7 | 5.59 | 5.69 | 5.72 | 5.87 | 5.74 | 5.68 |
| PMIDA (%) | ND | ND | 0.04 | 0.07 | 0.085 | 0.04 | 0.046 |
| AMPA (%) | 0.034 | 0.031 | 0.015 | 0.009 | 0.008 | DBNQ[1] | DBNQ |
| CH$_2$O (mg/g glyph. prod.) | 142 | 138 | 28 | 31 | 34 | 38 | 42 |
| HCO$_2$H (mg/g glyph. prod.) | 56 | 57 | DBNQ | 7 | 14 | 17 | 23 |
| AMPA/MAMPA (%) | 0.047 | 0.041 | 0.021 | 0.014 | 0.013 | 0.014 | 0.013 |
| NMG (mg/g glyph. prod.) | 16.3 | 19.3 | 0.7 | 0.9 | 1.4 | 2.3 | 2.6 |

[1]DBNQ = detectable, but not quantitated.

Example 14

Depositing a Tin Promoter on a Carbon Support

An activated carbon (20 g) was slurried in about 2 L of water. Next, 0.39 g of $SnCl_2.2H_2O$ was dissolved in 500 g of 0.5% $HNO_3$. The solution was added dropwise to the carbon slurry. After all the solution was added, the slurry was stirred for 2 hours. The pH then was adjusted to 9.5, and the slurry was stirred for a few more hours. Next, the slurry was filtered and washed with a plentiful amount of water until the filtrate reached a constant conductivity. The wet cake was dried at 125° C. under vacuum to give 1% tin on carbon. Following drying, the 1% tin on carbon was calcined in argon at 500° C. for 6 hours.

To deposit platinum onto the carbon support, 5 g of the 1% tin on carbon first was slurried in about 500 ml of water. Then 0.705 g of $H_2PtCl_6$ was dissolved in about 125 ml of water and added dropwise. After all the $H_2PtCl_6$ solution was added, the slurry was stirred for 2.5 hours. The pH then was adjusted to 9.5 with diluted NaOH and stirring was continued for a few more hours. The slurry then was filtered and washed with a plentiful amount of water until the filtrate reached constant conductivity. The wet cake was dried at 125° C. under vacuum.

This technique produced a catalyst comprising 5% platinum and 1% tin on carbon.

Example 15

Depositing an Iron Promoter onto a Carbon Support

Approximately 5 g of activated carbon was slurried in about 500 ml of water. Next, 0.25 g of $FeCl_3.6H_2O$ was hours. Next, the slurry was filtered and washed with a plentiful amount of water until the filtrate reached a constant conductivity. The wet cake was dried at 125° C. under vacuum.

This technique produces a catalyst comprising 5% platinum and 1% iron on carbon.

Example 16

Effect of Presence of Noble Metal on the Surface of the Carbon Support

This example shows the advantages of using a carbon support having a noble metal on its surface for effecting the oxidation of PMIDA rather than a carbon-only catalyst having no noble metal on its surface.

The PMIDA oxidation reaction was conducted in the presence of a carbon-only catalyst which was deoxygenated using the single-step high-temperature deoxygenation technique #2 described in Example 2. The reaction was carried out in a 300 ml stainless steel reactor using 0.365% catalyst, 8.2% PMIDA, a total reaction mass of 200 g a pressure of 65 psig, a temperature of 90° C., an agitation rate of 900 rpm, and an oxygen feed rate of 38 ml/min.

Table 12 shows the reaction times (i.e., the time for at least 98% of the PMIDA to be consumed) of 5 cycles for the carbon-only catalyst. Table 12 also shows the reaction times for the two Pt-on-carbon catalysts in Example 12 over 6 cycles under the reaction conditions described Example 12. As may be seen from Table 12, the deactivation of the carbon-only catalyst per cycle generally tends to be greater (i.e., the reaction times tend to increase more per cycle) than the deactivation of the carbon catalysts which had a noble metal on their surfaces. The deactivation particularly appears to be less where the catalyst has been reduced with NaBH$_4$ after the noble metal was deposited onto the surface. Without being bound by any particular theory, it is believed that the deactivation of the catalyst reduced with NaBH$_4$ was less than the deactivation of the other Pt-on-carbon catalyst because the platinum on the NaBH$_4$ catalyst leached less than the platinum on the other Pt-on-carbon catalyst. See Example 12, Tables 9 & 10.

TABLE 12

Results Using Catalyst which was not treated with NaBH$_4$

| Run # | 1 | 2 | 3 | 4 | 5 | 6 |
|---|---|---|---|---|---|---|
| Run Time for Carbon-Only Catalyst (min.) | 45.4 | 55.0 | 64.4 | 69.8 | 75.0 | |
| Run Time for 5% platinum on Carbon Catalyst which was Reduced w/ NaBH$_4$ (min.) | 35.1 | NA[1] | NA | 35.2 | 35.8 | 35.8 |
| Run Time for 5.23% platinum on Carbon Catalyst (min.) | 40.4 | 42.0 | 44.2 | 44.1 | 44.9 | 52.7 |

[1] Not available due to temperature problems.

Example 17

The Effect of Using a Catalyst Comprising a Noble Metal Alloyed with a Catalyst-Surface Promoter This example shows the advantages of a catalyst comprising platinum alloyed with iron.

1. Catalyst Comprising Platinum Alloyed with Iron

To prepare the catalyst comprising platinum alloyed with iron, approximately 10 grams of an activated carbon was slurried in about 180 ml of water. Next, 0.27 grams of FeCl$_3$.6H$_2$O and 1.39 grams of H$_2$PtCl$_6$ hydrate were co-dissolved in about 60 ml of water. This solution was added dropwise to the carbon slurry over a period of about 30 minutes. During the addition, the pH of the slurry dropped and was maintained at from about 4.4 to about 4.8 using a dilute NaOH solution (i.e., a 1.0 to 2.5 molar solution of NaOH). Afterward, the slurry was stirred for 30 more minutes at a pH of about 4.7. The slurry then was heated under N$_2$ to 70° C. at a rate of about 2° C./min. while maintaining the pH at about 4.7. Upon reaching 70° C., the pH was raised slowly over a period of about 30 minutes to 6.0 with addition of the dilute NaOH solution. The stirring was continued for a period of about 10 min. until the pH became steady at about 6.0. The slurry was then cooled under N$_2$ to about 35° C. Subsequently, the slurry was filtered, and the cake was washed with approximately 800 ml of water 3 times. The cake was then dried at 125° C. under a vacuum. This produced a catalyst containing 5 wt. % platinum and 0.5 wt. % iron on carbon upon heating at 690° C. in 20% H$_2$ and 80% Ar for 1–6 hr.

This catalyst was analyzed via electron microscopy, as described in more detail in Example 19. An image obtained through TEM of the carbon support showed that the alloyed metal particles were highly dispersed and uniformly distributed throughout the carbon support (the white dots represent the metal particles; and the variations in the background intensity are believed to represent the change of the local density of the porous carbon). The average size of the particles was about 3.5 nm, and the average distance between particles was about 20 nm. A high energy resolution X-ray spectra from an individual metal particle of the catalyst showed that both platinum and iron peaks were present (the copper peaks originated from the scattering of the copper grids). Quantitative analysis of the high energy resolution X-ray spectra from different individual metal particles showed that the composition of the particles, within experimental error, did not vary with the size or the location of the metal particles on the catalyst surface.

2. Catalyst in which Platinum was less Alloyed with Iron

To prepare the Pt/Fe/C catalyst in which the platinum was less alloyed with iron (i.e., this catalyst has less platinum alloyed with iron than does the first catalyst described in this example), the platinum and iron were deposited sequentially onto the surface of the carbon support. Approximately 5 grams of an activated carbon was slurried in about 500 ml of water. The pH was adjusted to about 5.0 with 1N HCl. Next, about 0.25 grams of FeCl$_3$.6H$_2$O was dissolved in 75 ml of water. This solution was added dropwise to the carbon slurry over a period of about 60 min. After all the solution was added, the slurry was stirred for about 2 hours. The pH was adjusted to 9.5 with the dilute NaOH solution, and the slurry was stirred for a few more hours. Afterward, the slurry was filtered and washed with a plentiful amount of water. The wet cake was dried at 125° C. under vacuum to produce 1 wt. % iron on carbon. Following drying, this 1 wt. % iron on carbon was reduced with an atmosphere containing 20% H$_2$ and 80% Ar at 635° C. for 1–6 hr. About 2.5 grams of this 1 wt. % iron on carbon was slurried in 250 ml of water. Next, about 0.36 grams of H$_2$PtCl$_6$ hydrate was dissolved in 65 ml of water, which, in turn, was added dropwise to the slurry over a period of about 60 min. After all the solution was added, the slurry was stirred for 2 hours. The slurry then was filtered and washed with a plentiful amount of water. The cake was then re-slurried in 450 ml of water. After adjusting the pH of the slurry to 9.5 with the dilute NaOH solution, the slurry was stirred for about 45 min. Next, the slurry was filtered and washed once with 450 ml of water. The wet cake was the dried at 125° C. under vacuum. This produced a catalyst containing 5 wt. % platinum and 1 wt. % iron on carbon upon reduction by heating to a temperature of 660° C. in an atmosphere containing 20% H$_2$ and 80% Ar for 1–6 hr.

3. Comparison of the Two Catalysts

These two catalysts were compared while catalyzing the PMIDA oxidation reaction. The reaction conditions were the same as those in Example 5. Table 13 shows the results. The first catalyst described in this example (i.e., the catalyst comprising a greater amount of platinum alloyed with iron) had greater stability with respect to CH$_2$O & HCO$_2$H activities; the second catalyst described in this example (i.e., the catalyst comprising a lower amount of platinum alloyed with iron) deactivated rapidly. In addition, the first catalyst retained almost half of its iron content over 25 cycles, while the second catalyst lost most of its iron in the first cycle.

TABLE 13

Comparison of Catalyst Having Pt/Fe Alloy with Catalyst Having Less Pt/Fe Alloy

| | cycle 1 | cycle 2 | cycle 3 | cycle 4 | cycle 5 | cycle 6 | cycle 7 | cycle 8 | cycle 9 | cycle 10 | cycle 11 | cycle 12 | cycle 13 |
|---|---|---|---|---|---|---|---|---|---|---|---|---|---|
| Alloyed Pt & Fe | | | | | | | | | | | | | |
| $CH_2O$ (mg/g glyph. prod.) | 10.49 | | 9.23 | | 6.04 | | 4.92 | | 4.44 | | 5.08 | | 5.24 |
| $HCO_2H$ (mg/g glyph. prod.) | 19.91 | | 29.64 | | 27.84 | | 25.62 | | 27.99 | | 29.73 | | 28.95 |
| NMG (mg/g glyph. prod.) | 0.22 | | 0.44 | | 0.28 | | 0 | | 0 | | 0 | | 0 |
| Pt in soln. (μg/g glyph. prod.) | 5.08 | | 4.87 | | 3.6 | | 3.06 | | | | | | |
| % of Fe Lost | 44 | | 1.9 | | 1.2 | | 0.8 | | | | | | |
| Less alloyed Pt & Fe | | | | | | | | | | | | | |
| $CH_2O$ (mg/g glyph. prod.) | 10.16 | 10.7 | 12.24 | 13.56 | 14.68 | | | | | | | | |
| $HCO_2H$ (mg/g glyph. prod.) | 27.23 | 37.72 | 45.01 | 54.57 | 61.14 | | | | | | | | |
| NMG (mg/g glyph. prod.) | 0 | 0.98 | 1.23 | 1.77 | 2 | | | | | | | | |
| Pt in soln. (μg/g glyph. prod.) | 3.83 | 3.36 | 3.54 | 3.44 | 3.32 | | | | | | | | |
| % of Fe Lost | 86 | 3.2 | 1.4 | 1.8 | 1.4 | | | | | | | | |

Example 18

Preparation of a Pt/Fe/Sn on Carbon Catalyst

Approximately 10 grams of an activated carbon was slurried in about 90 ml of water. Next, about 0.2 g of $SnCl_2 \cdot 2H_2O$ was dissolved in 250 ml of 0.025 M HCl. The solution was added dropwise to the carbon slurry. After all the solution was added, the slurry was stirred for 3 hr. The pH then was slowly adjusted to 9.0 with a diluted NaOH solution (i.e., a 1.0 to 2.5 molar solution of NaOH), and the slurry was stirred for a few more hours. Next, the slurry was filtered and washed with a plentiful amount of water until the filtrate reached a constant conductivity. The wet cake was dried at 125° C. under vacuum. This produced 0.9 wt. % tin on carbon. About 6 grams of this 0.9 wt. % tin on carbon was slurried in about 500 ml of water. Then approximately 0.23 grams of $Fe(NO_3)_3 \cdot 9H_2O$ and 0.85 grams of $H_2PtCl_6$ were co-dissolved in about 150 ml of water and added dropwise to the slurry. After all the solution was added, the slurry was stirred for 4 hours, and then filtered to remove excess iron (~80 wt. %). The wet cake was re-slurried in 480 ml of water. After the pH of the slurry was adjusted to 9–10 with the dilute NaOH solution, the slurry was stirred for a few more hours. Next, the slurry was filtered and washed with a plentiful amount of water until the filtrate reached a constant conductivity. The wet cake was dried at 125° C. under vacuum. This produced a catalyst containing 4.9 wt. % Pt, 0.9 wt. % tin and 0.1 wt. % iron on carbon upon high-temperature reduction by heating at 700–750° C. in 20% $H_2$ and 80% Ar for 1–6 hr.

Example 19

Electron Microscopy Characterization of Catalysts

Electron microscopy techniques were used to analyze the size, spacial distribution, and composition of the metal particles of catalysts prepared in Example 17. Before analyzing the catalyst, the catalyst was first embedded in an EM Bed 812 resin (Electron Microscopy Sciences, Fort Washington, Pa.). The resin was then polymerized at about 60° C. for approximately 24 hr. The resulting cured block was ultramicrotomed into slices having a thickness of about 50 nm. These slices were then transferred to 200 mesh copper grids for electron microscopy observation.

High-resolution analytical electron microscopy experiments were carried out in a Vacuum Generators dedicated scanning transmission electron microscope (model no. VG HB501, Vacuum Generators, East Brinstead, Sussex, England) with an image resolution of less than 0.3 nm. The microscope was operated at 100 kV. The vacuum in the specimen chamber area was below about $10^{-6}$ Pa. A digital image acquisition system (ES Vision Data Acquisition System, EmiSpec Sys., Inc., Tempe, Ariz.) was used to obtain high-resolution electron microscopy images. A windowless energy dispersive X-ray spectrometer (Link LZ-5 EDS Windowless Detector, Model E5863, High Wycombe, Bucks, England) was used to acquire high energy resolution X-ray spectra from individual metal particles. Because of its high atomic-number sensitivity, high-angle annular dark-field (HAADF) microscopy was used to observe the metal particles. An electron probe size of less than about 0.5 nm was used to obtain the HAADF images, and a probe size of less than about 1 nm was used to obtain high energy resolution X-ray spectra.

Example 20

Effect of a Supplemental Promoter

This example shows the use and advantages of mixing a supplemental promoter with a carbon-supported, noble-metal-containing oxidation catalyst.

A. Comparison of Effects on a PMIDA Oxidation Reaction caused by Mixing a Carbon-supported, Noble-metal-containing Catalyst with Various Amounts and Sources of Bismuth Several single batch PMIDA oxidation reactions were conducted. In each reaction, a different source and a different amount of bismuth were added to the reaction medium. The source of bismuth was either $(BiO)_2CO_3$, $Bi(NO_3)_3 \cdot 5H_2O$, or $Bi_2O_3$. The amount of bismuth used corresponded to a bismuth to PMIDA mass ratio of 1:10,000; 1:2,000; or 1:1,000. A control was also conducted wherein no bismuth was added.

Each PMIDA oxidation reaction was conducted in the presence of a catalyst containing 5% by weight platinum and 0.5% by weight iron (this catalyst was prepared using a method similar to that described in Example 17). The reaction was carried out in a 1000 ml stainless steel reactor (Autoclave Engineers, Pittsburgh, Pa.) using 2.5 g catalyst (0.5% by weight of the total reaction mass), 60.5 g PMIDA (12.1% by weight of the total reaction mass), 1000 ppm formaldehyde, 5000 ppm formic acid, a total reaction mass of 500 g, a pressure of 110 psig, a temperature of 100° C., and an agitation rate of 1000 rpm. The oxygen feed rate for the first 22 minutes was 392 ml/min., and then 125 ml/min. until the PMIDA was essentially depleted.

Table 14 shows the results. In all the runs where a bismuth compound was added, the formaldehyde, formic acid, and NMG levels were less than those observed in the control.

All 4 experiments were conducted using a catalyst containing 5% by weight platinum and 0.5% by weight iron (this catalyst was prepared using a method similar to that described in Example 17). During each 6-run experiment, the same catalyst was used in each of the 6 runs (i.e., after the end of a run, the reaction product solution was separated and removed from the catalyst, and a new batch of PMIDA was then combined with the catalyst to begin a new run). The reaction was carried out in a 1000 ml stainless steel reactor (Autoclave Engineers) using 2.5 g catalyst (0.5% by weight of the total reaction mass), 60.5 g PMIDA (12.1% by weight of the total reaction mass), 1000 ppm formaldehyde, 5000 ppm formic acid, a total reaction mass of 500 g, a pressure of 110 psig, a temperature of 100° C., and an agitation rate of 1000 rpm. The oxygen feed rate for the first 22 minutes was 392 ml/min., and then 125 ml/min. until the PMIDA was essentially depleted.

In the control experiment, no bismuth was introduced into the reaction zone during any of the 6 runs. In the three other experiments, 0.034 grams of bismuth(III) oxide (i.e., $Bi_2O_3$) were introduced into the reaction medium at the beginning of the first reaction run. In one of these experiments, the

TABLE 14

Direct Addition of Various Sources and Amounts of Bismuth

| Amt. & source of Bi Added | Glyph. (%)** | PMIDA (%)** | $CH_2O$ (mg/g)*** | $HCO_2H$ (mg/g)*** | AMPA/ MAMPA (mg/g)*** | NMG (mg/g)*** | Run Time (min.) |
|---|---|---|---|---|---|---|---|
| 0 (control) | 8.2 | ND | 4.0 | 22.5 | 9.4 | 2.0 | 39.3 |
| 0.0074 g $(BiO)_2CO_3$ (100 ppm*) | 8.1 | ND | 2.6 | 3.8 | 10.9 | ND | 54.1 |
| 0.037 g $(BiO)_2CO_3$ (500 ppm) | 7.8 | ND | 1.8 | 1.4 | 14.5 | ND | 58.2 |
| 0.074 g $(BiO)_2CO_3$ (1000 ppm) | 7.7 | ND | 2.0 | 1.3 | 16.4 | ND | 60.2 |
| 0.0141 g $Bi(NO_3)_3 \cdot 5H_2O$ (100 ppm) | 8.1 | ND | 2.4 | 3.0 | 11.2 | ND | 53.2 |
| 0.070 g $Bi(NO_3)_3 \cdot 5H_2O$ (500 ppm) | 7.7 | ND | 1.9 | 1.4 | 14.4 | ND | 58.5 |
| 0.141 g $Bi(NO_3)_3 \cdot 5H_2O$ (1000 ppm) | 7.6 | ND | 2.0 | 1.2 | 16.2 | ND | 59.2 |
| 0.0067 g $Bi_2O_3$ (100 ppm) | 8.1 | ND | 2.5 | 3.5 | 13.9 | ND | 48 |
| 0.034 g $Bi_2O_3$ (500 ppm) | 7.6 | ND | 2.0 | 1.4 | 15.1 | ND | 58.7 |
| 0.067 g $Bi_2O_3$ (1000 ppm) | 7.6 | ND | 2.0 | 1.2 | 17.3 | ND | 60.6 |

*ppm means a ratio of Bi to PMIDA equaling 1:1,000,000
**(mass ÷ total reaction mass) × 100%
***mg ÷ grams of glyphosate produced
"ND" means none detected B. Effect of Bismuth addition on Subsequent PMIDA Oxidation batches Contacted with the Catalyst Four 6-run experiments (i.e., during each of the 4 experiments, 6 batch reactions were conducted in sequence) were conducted to determine the effect of (1) the initial bismuth addition on reaction runs subsequent to the initial bismuth addition, and (2) adding additional bismuth in one or more of the subsequent reaction runs.

bismuth oxide was only introduced into the reaction zone at the beginning of the first reaction run. In another experiment, 0.034 g of bismuth (III) oxide was introduced into the reaction medium at the beginning of the first and fourth reaction runs. In the final experiment, 0.034 g of bismuth(III) oxide was introduced into the reaction medium at the beginning of all 6 reaction runs.

Tables 15, 16, 17, and 18 show the results. The one-time addition of the bismuth oxide (data shown in Table 16)

tended to give the same beneficial effects as adding the bismuth oxide every three runs (data shown in Table 17) or even every run (data shown in Table 18).

TABLE 15

Control Experiment: 6-Run PMIDA Oxidation Reaction with No Bismuth Addition

| Sample (unless otherwise indicated, taken after approx. all PMIDA consumed) | Run 1 | Run 2 | Run 3 | Run 4 | Run 5 | Run 6 |
|---|---|---|---|---|---|---|
| Glyphosate (%)* | 8.2 | 8.4 | 8.4 | 8.5 | 8.5 | 8.4 |
| PMIDA (%)* | ND | 0.006 | 0.008 | ND | ND | ND |
| $CH_2O$ (mg/g)** | 3.1 | 2.4 | 2.0 | 2.6 | 3.2 | 3.8 |
| $HCO_2H$ (mg/g)** | 16 | 23 | 22 | 25 | 30 | 40 |
| AMPA/MAMPA (mg/g)** | 7.5 | 6.9 | 6.3 | 5.5 | 5.8 | 5.9 |
| NMG (mg/g)** | 0.5 | 1.7 | 1.4 | 1.6 | 2.8 | 4.9 |
| Time (min.) | 48.5 | 43.5 | 54.5 | 52.8 | 54.1 | 51.7 |

*(mass ÷ total reaction mass) × 100%
**mg ÷ grams of glyphosate produced
"ND" means none detected

TABLE 16

6-Run PMIDA Oxidation Reaction with Bismuth Addition at Beginning of First Run

| Sample (unless otherwise indicated, taken after approx. all PMIDA consumed) | Run 1 | Run 2 | Run 3 | Run 4 | Run 5 | Run 6 |
|---|---|---|---|---|---|---|
| Glyphosate (%)* | 7.8 | 8.6 | 8.5 | 8.6 | 8.6 | 7.7 |
| PMIDA (%)* | ND | ND | ND | ND | ND | 0.005 |
| $CH_2O$ (mg/g)** | 2.4 | 2.7 | 2.1 | 2.6 | 3.1 | 3.9 |
| $HCO_2H$ (mg/g)** | DBNQ | DBNQ | DBNQ | DBNQ | DBNQ | DBNQ |
| AMPA/MAMPA (mg/g)** | 15 | 11 | 10 | 9.9 | 8.6 | 10 |
| NMG (mg/g)** | ND | ND | ND | ND | ND | ND |
| Time (min.) | 60.1 | 62.4 | 64.1 | 62.6 | 66.9 | 62 |

*(mass ÷ total reaction mass) × 100%
**mg ÷ grams of glyphosate produced
"ND" means none detected
"DBNQ" means detected, but not quantified

TABLE 17

6-Run PMIDA Oxidation Reaction with Bismuth Addition at Beginning of 1st and 4th Runs

| Sample (unless otherwise indicated, taken after approx. all PMIDA consumed) | Run 1 | Run 2 | Run 3 | Run 4 | Run 5 | Run 6 |
|---|---|---|---|---|---|---|
| Glyphosate (%)* | 7.8 | 8.4 | 8.5 | 8.5 | 8.5 | 8.6 |
| PMIDA (%)* | ND | ND | ND | ND | ND | ND |
| $CH_2O$ (mg/g)* | 2.3 | 2.6 | 2.6 | 3.2 | 3.6 | 3.5 |
| $HCO_2H$ (mg/g)** | 3.4 | 3.1 | 3.2 | 2.9 | 3.3 | 3.5 |
| AMPA/MAMPA (mg/g)** | 14 | 11 | 10 | 11 | 9.3 | 8.9 |
| NMG (mg/g)** | ND | ND | ND | ND | ND | ND |
| Time (min.) | 57.4 | 63.2 | 64.3 | 64.9 | 66 | 64.5 |

*(mass ÷ total reaction mass) × 100%
**mg ÷ grams of glyphosate produced
"ND" means none detected

TABLE 18

6-Run PMIDA Oxidation Reaction with Bismuth Addition at Beginning of Every Run

| Sample (unless otherwise indicated, taken after approx. all PMIDA consumed) | Run 1 | Run 2 | Run 3 | Run 4 | Run 5 | Run 6 |
|---|---|---|---|---|---|---|
| Glyphosate (%)* | 7.8 | 8.5 | 8.2 | 8.3 | 8.3 | 8.3 |
| PMIDA (%)* | ND | ND | ND | ND | ND | ND |
| $CH_2O$ (mg/g)** | 2.4 | 2.8 | 3.2 | 2.9 | 3.4 | 4.0 |
| $HCO_2H$ (mg/g)** | ND | ND | ND | ND | ND | ND |
| AMPA/MAMPA (mg/g)** | 14 | 12 | 11 | 12 | 10 | 9.7 |
| NMG (mg/g)** | ND | ND | ND | ND | ND | ND |
| Time (min.) | 56.4 | 62.4 | 64.8 | 62.8 | 66 | 66.1 |

*(mass ÷ total reaction mass) × 100%
**mg ÷ grams of glyphosate produced
"ND" means none detected C. Effect of a One-time Bismuth Addition over 20 PMIDA Oxidation Runs using a Platinum/Iron/Carbon Catalyst Two 20-run experiments were conducted to determine the effect of a one-time bismuth addition on 20 PMIDA oxidation reaction runs.

Both experiments were conducted using a catalyst containing 5% by weight platinum and 0.5% by weight iron (this catalyst was prepared using a similar method to the method described in Example 17). During each experiment, the same catalyst was used in each of the 20 runs. The reaction was carried out in a 1000 ml stainless steel reactor (Autoclave Engineers) using 2.5 g catalyst (0.5% by weight of the total reaction mass), 60.5 g PMIDA (12.1% by weight of the total reaction mass), 1000 ppm formaldehyde, 5000 ppm formic acid, a total reaction mass of 500 g, a pressure of 110 psig, a temperature of 100° C., and an agitation rate of 1000 rpm. The oxygen feed rate for the first 22 minutes was 392 ml/min., and then 125 ml/min. until the PMIDA was essentially depleted. In the control experiment, no bismuth was introduced into the reaction zone during any of the 20 runs. In the other experiment, 0.034 grams of bismuth (III) oxide was introduced into the reaction medium at the beginning of the first reaction run.

Figure 3:
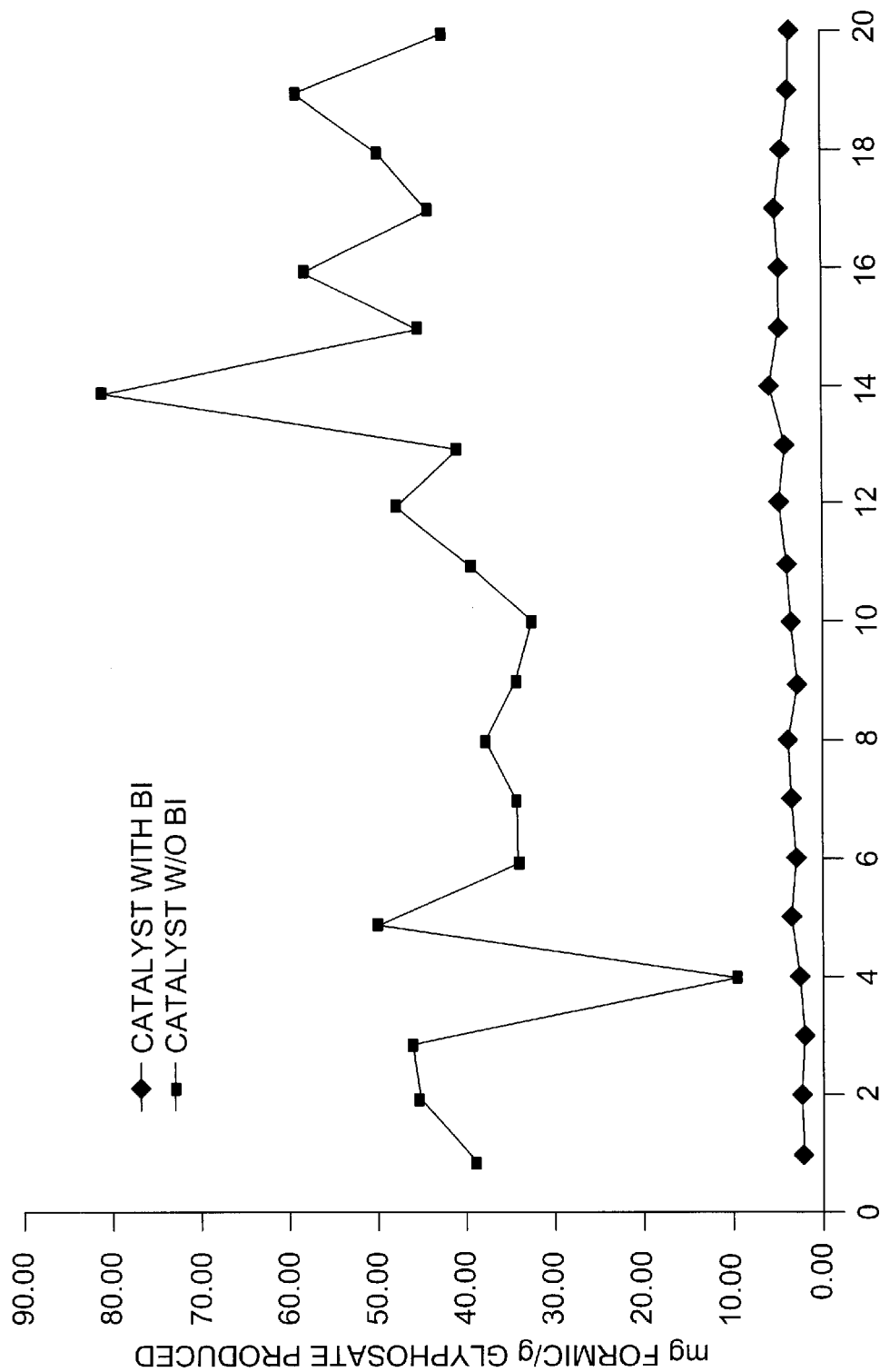
FIG. 3 shows the effect on the formic acid byproduct concentration profile over 20 reaction runs caused by a one-time introduction of bismuth oxide directly into a PMIDA oxidation reaction mixture. Here, the catalyst concentration in the reaction mixture was 0.5% by weight, and the catalyst contained 5% by weight platinum and 0.5% by weight iron.
Figure 4:
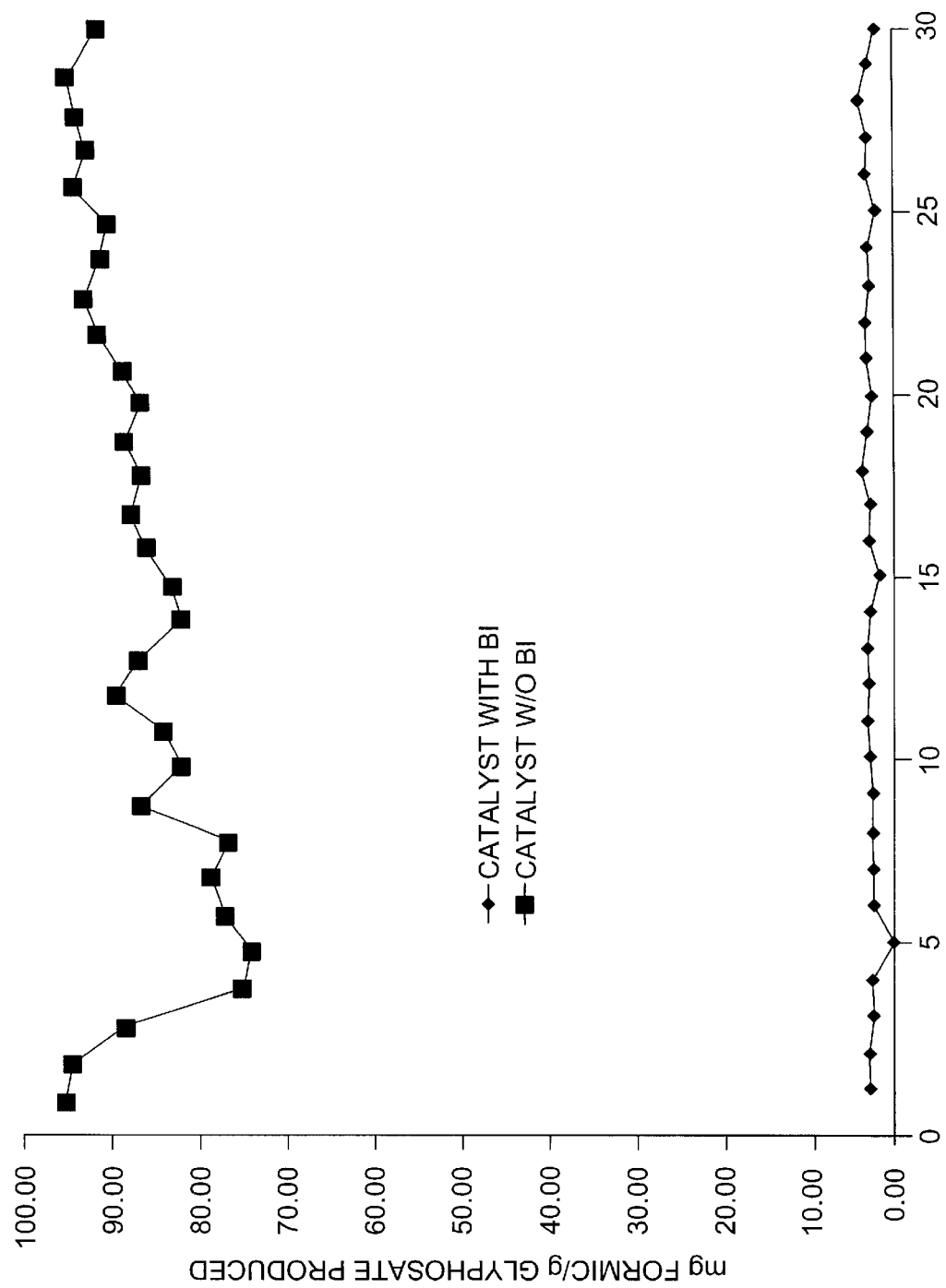
FIG. 4 shows the effect on the formic acid byproduct concentration profile over 30 reaction runs caused by a one-time introduction of bismuth oxide directly into a PMIDA oxidation reaction mixture. Here, the catalyst concentration in the reaction mixture was 0.75% by weight, and the catalyst contained 5% by weight platinum and 1% by weight tin.

FIG. 3 compares the resulting formic acid concentration profiles. The one-time introduction of bismuth into the reaction zone decreased the formic acid concentration over all 20 runs.

D. Effect of a One-time Bismuth Addition over 30 PMIDA Oxidation Runs using a Platinum/Tin/Carbon Catalyst Two 30-run experiments were conducted to determine the effect of a one-time bismuth addition on 30 PMIDA oxidation reaction runs.

Both experiments were conducted using a catalyst containing 5% by weight platinum and 1% by weight tin (this catalyst was prepared using a method similar to that described in Example 18). During each experiment, the same catalyst was used in each of the 30 runs. Each run was carried out in a 300 ml reactor (made of alloy metal, Hastelloy C, Autoclave Engineers) using 1.35 g catalyst (0.75% by weight of the total reaction mass), 21.8 g PMIDA (12.1% by weight of the total reaction mass), 1000 ppm formaldehyde, 5000 ppm formic acid, a total reaction mass of 180 g, a pressure of 90 psig, a temperature of 100° C., and an agitation rate of 900 rpm. The oxygen feed rate for the first 26 minutes was 141 ml/min., and then 45 ml/min. until the PMIDA was essentially depleted. In the control experiment, no bismuth was introduced into the reaction zone during any of the 30 runs. In the other experiment, 0.012 grams of bismuth (III) oxide was introduced into the reaction medium at the beginning of the first reaction run.

Figure 5:
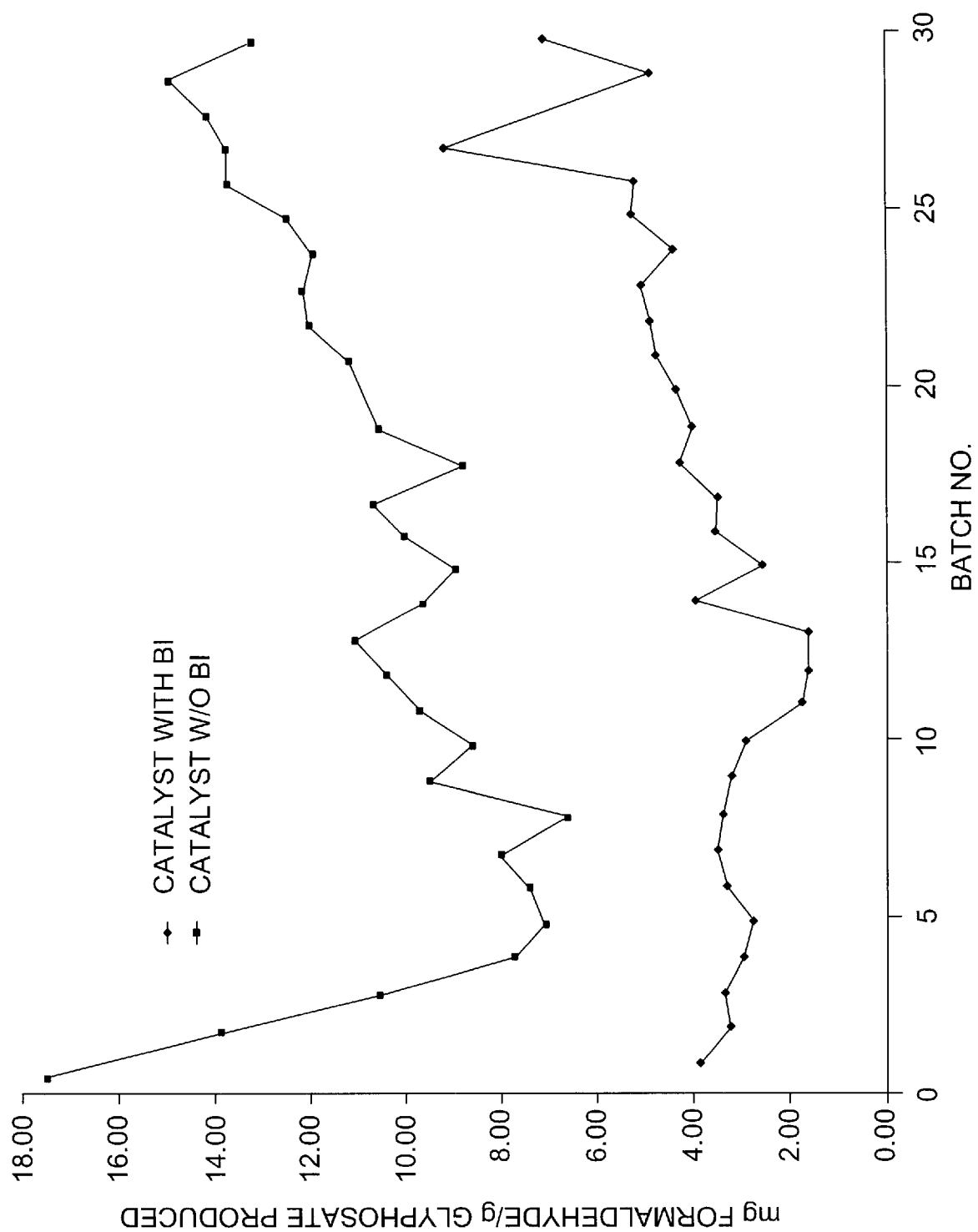
FIG. 5 shows the effect on the formaldehyde byproduct concentration profile over 30 reaction runs caused by a one-time introduction of bismuth oxide directly into a PMIDA oxidation reaction mixture. Here, the catalyst concentration in the reaction mixture was 0.75% by weight, and the catalyst contained 5% by weight platinum and 1% by weight tin.
Figure 6:
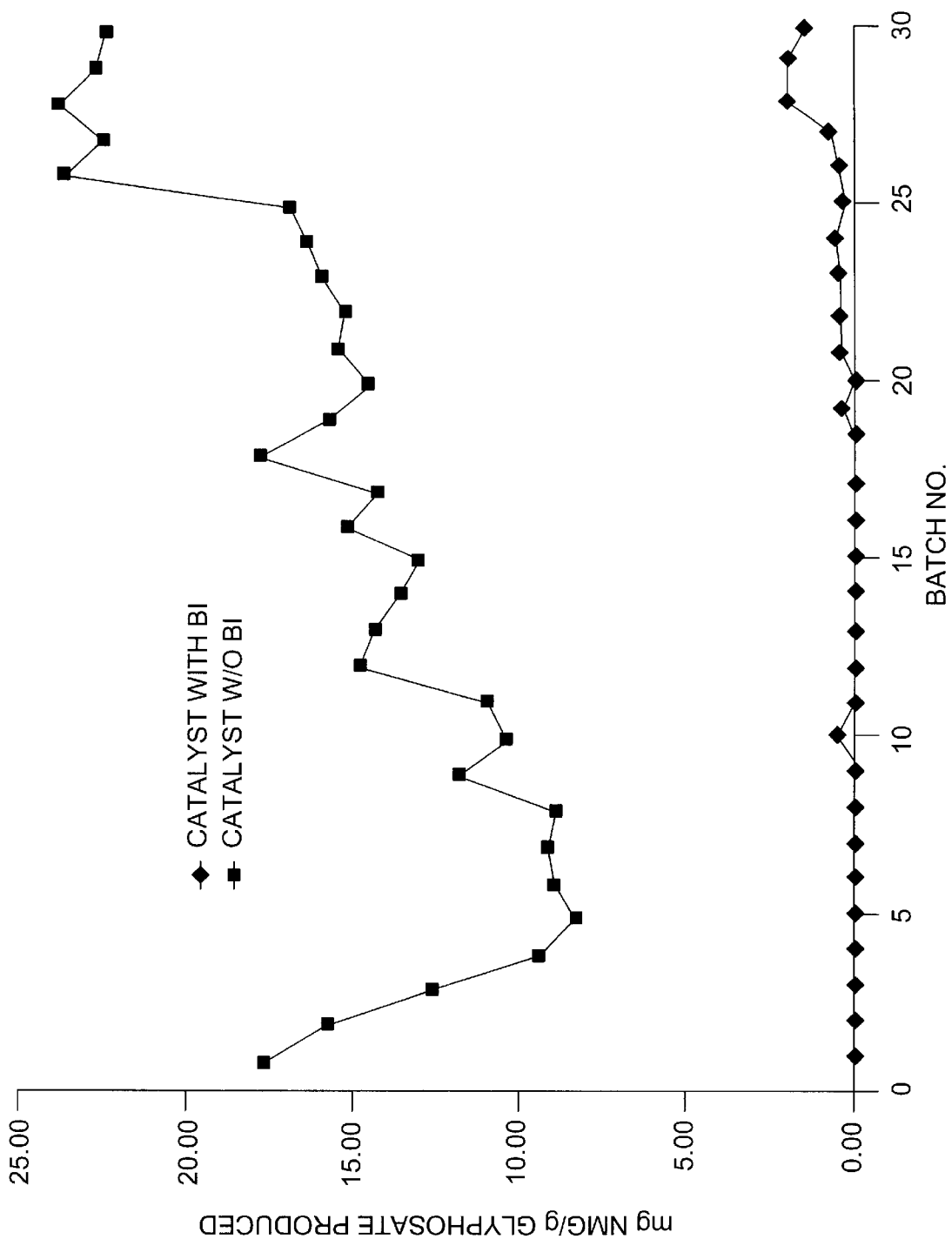
FIG. 6 shows the effect on the NMG byproduct concentration profile over 30 reaction runs caused by a one-time introduction of bismuth oxide directly into a PMIDA oxidation reaction mixture. Here, the catalyst concentration in the reaction mixture was 0.75% by weight, and the catalyst contained 5% by weight platinum and 1% by weight tin.

FIG. 3 compares the resulting formic acid concentration profiles, FIG. 5 compares the resulting formaldehyde concentration profiles, and FIG. 6 compares the resulting NMG concentration profiles. Even after 30 runs, the one-time introduction of bismuth into the reaction zone decreased the formic acid concentration by 98%, the formaldehyde concentration by 50%, and the NMG concentration by 90%.

E. Effect of Adding Bismuth to a Pt/Fe/C Catalyst that was Previously used in 132 Batch PMIDA Oxidation Reactions A 14-run experiment was conducted to determine the effect mixing bismuth with a used Pt/Fe/C catalyst. Before this experiment, the catalyst had been used to catalyze 129 batch PMIDA oxidation reactions. The fresh catalyst (i.e., the catalyst before it was used in the previous 129 PMIDA oxidation runs) was prepared using a method similar to the method described in Example 17, and contained 5% by weight platinum and 0.5% by weight iron.

The 14 PMIDA oxidation reaction runs were carried out in a 300 ml reactor (made of alloy metal, Hastelloy C, Autoclave Engineers) using 0.9 g of spent catalyst (0.5% by weight), 21.8 g PMIDA (12.1% by weight), 1000 ppm formaldehyde, 5000 ppm formic acid, a total reaction mass of 180 g, a pressure of 90 psig, a temperature of 100° C., and an agitation rate of 900 rpm. The oxygen feed rate for the first 26 minutes was 141 ml/min., and then 45 ml/min. until the PMIDA was essentially depleted. At the beginning of the 4th run, 0.012 grams of bismuth(III) oxide was introduced into the reaction zone.

Figure 7:
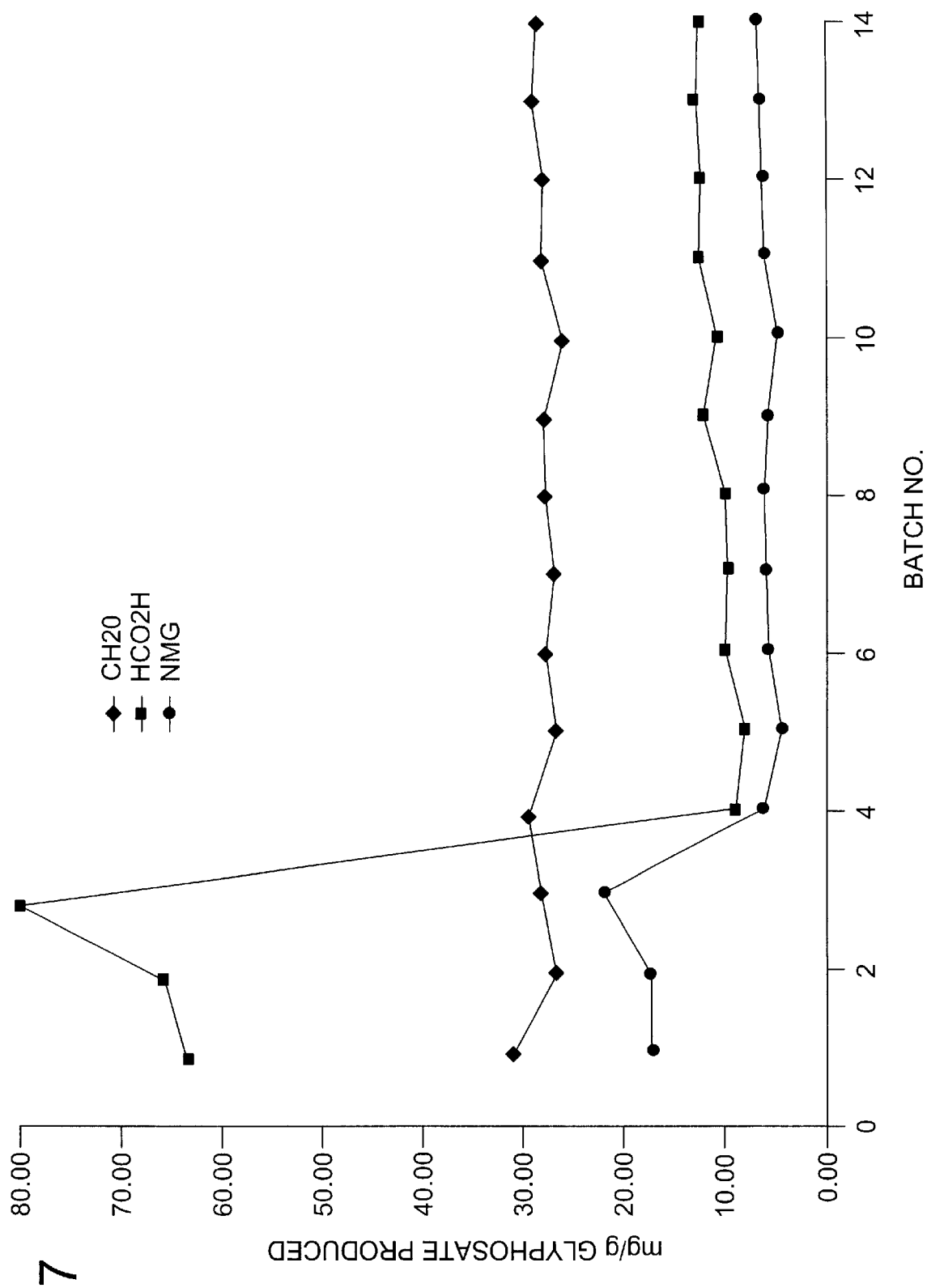
FIG. 7 shows the effect on formic acid, formaldehyde, and NMG production during a PMIDA oxidation reaction caused by mixing bismuth oxide with an oxidation catalyst that had been used in 133 previous batch PMIDA oxidation reactions. Here, the catalyst comprised 5% by weight platinum and 0.5% by weight iron on a carbon support.

FIG. 7 shows the effects that the bismuth addition at the 4th run had on the formic acid, formaldehyde, and NMG byproduct production.

F. Effect of Adding Bismuth to a Pt/Sn/C Catalyst that was Previously used in 30 Batch PMIDA Oxidation Reactions An 11-run experiment was conducted to determine the effect of mixing bismuth with a used Pt/Sn/C catalyst. The catalyst had previously been used to catalyze 30 batch PMIDA oxidation reactions. The fresh catalyst (i.e., the catalyst before it was used in the previous 30 PMIDA oxidation runs) was prepared using a method similar to that described in Example 18, and contained 5% by weight platinum and 1% by weight tin.

The 11 PMIDA oxidation reaction runs were carried out in a 300 ml reactor (made of alloy metal, Hastelloy C, Autoclave Engineers) using 1.35 g of used catalyst (0.75% by weight of the total reaction mass), 21.8 g PMIDA (12.1% by weight of the total reaction mass), 1000 ppm formaldehyde, 5000 ppm formic acid, a total reaction mass of 180 g, a pressure of 90 psig, a temperature of 100° C., and an agitation rate of 900 rpm. The oxygen feed rate for the first 26 minutes was 141 ml/min., and then 45 ml/min. until the PMIDA was essentially depleted. At the beginning of the 4th run, 0.012 grams of bismuth(III) oxide was introduced into the reaction zone.

Figure 8:
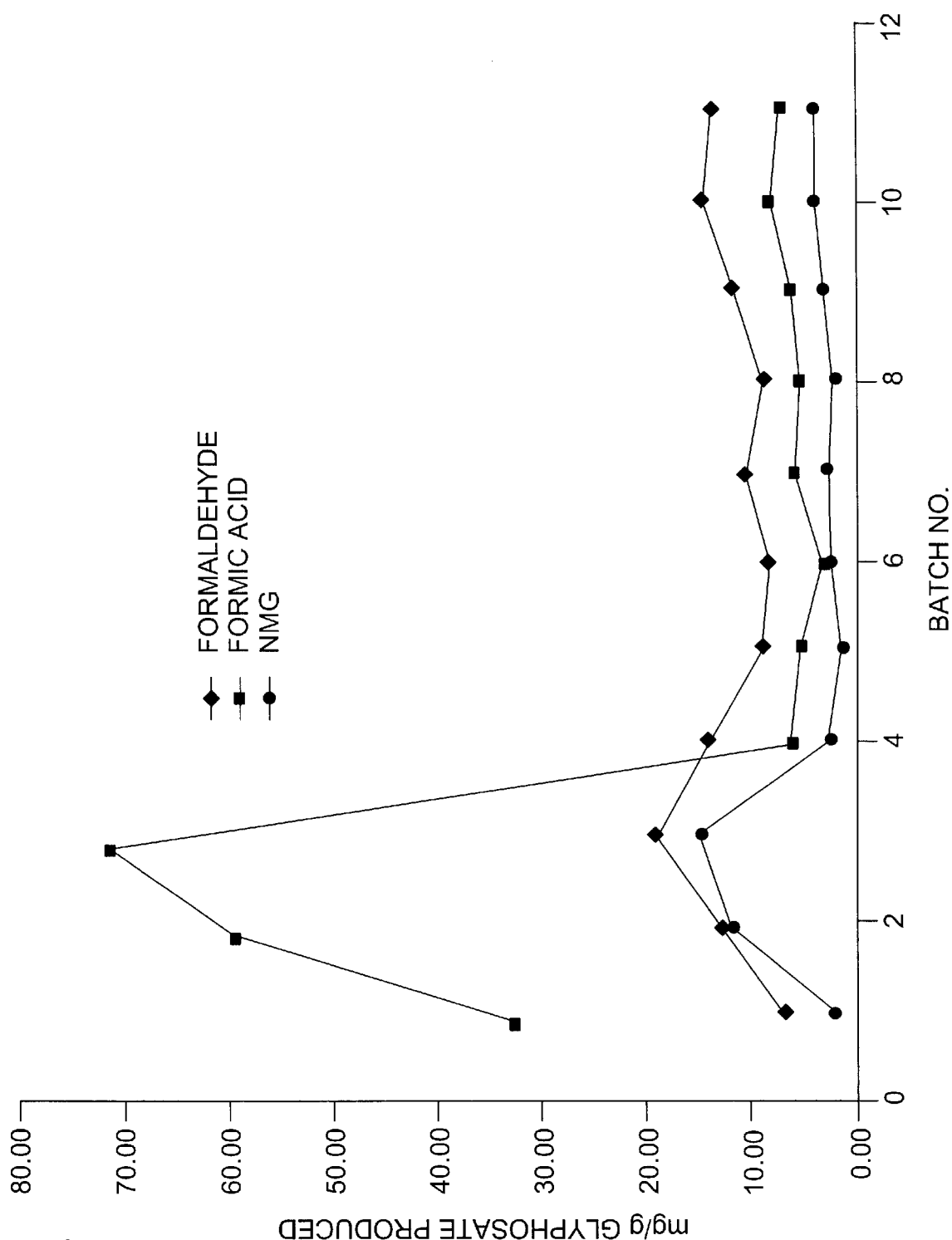
FIG. 8 shows the effect on formic acid, formaldehyde, and NMG production during a PMIDA oxidation reaction caused by mixing bismuth oxide with an oxidation catalyst that had been used in 30 previous batch PMIDA oxidation reactions. Here, the catalyst comprised 5% by weight platinum and 1% by weight tin on a carbon support.

FIG. 8 shows the effects that the bismuth addition at the 4th run had on the formic acid, formaldehyde, and NMG byproduct production.

G. Effect of Bismuth Addition on over 100 Subsequent PMIDA Oxidation Batches Contacted with the Catalyst Two 125-run experiments were conducted to determine the effect of bismuth addition on over 100 subsequent reaction runs using the same catalyst.

Both experiments were conducted using a catalyst containing 5% by weight platinum and 1% by weight tin (this catalyst was prepared using a method similar to that described in Example 18). During each experiment, the same catalyst was used in all the runs. The reaction was carried out in a stirred-tank reactor using 0.75% catalyst (by weight of the total reaction mass), 12.1% PMIDA (by weight of the total reaction mass), a pressure of 128 psig, and a temperature of 100° C. The oxygen feed rate for the first part of each batch reaction (the exact amount of time varied with each batch from 14.9 to 20.3 minutes, with times closer to 14.9 minutes being used for the earlier batches, and times closer to 20.3 minutes being used for the later batches) was 1.3 mg/min. per gram total reaction mass, and then 0.35 mg/min. per gram total reaction mass until the PMIDA was essentially depleted. A portion of the reaction product from each batch was evaporated off and returned to the reactor as a source of formaldehyde and formic acid to act as sacrificial reducing agents in the next batch reaction. The amounts of formaldehyde and formic acid recycled back to the reactor ranged from 100 to 330 ppm, and from 0 ppm to 2300 ppm (0 to 200 ppm formic acid after 25 batches following the addition of bismuth (III) oxide), respectively.

In the control experiment, no bismuth was introduced into the reaction zone during any of the 125 runs. In the other experiment, the catalyst was first used to catalyze 17 batches of PMIDA. After catalyzing the 17th batch, the catalyst was substantially separated from the reaction product, and the resulting catalyst mixture was transferred to a catalyst holding tank where 9.0 mg of bismuth (III) oxide per gram of catalyst were introduced into the catalyst mixture. The catalyst was then used to catalyze the oxidation of 107 subsequent batches of PMIDA.

Figure 9:
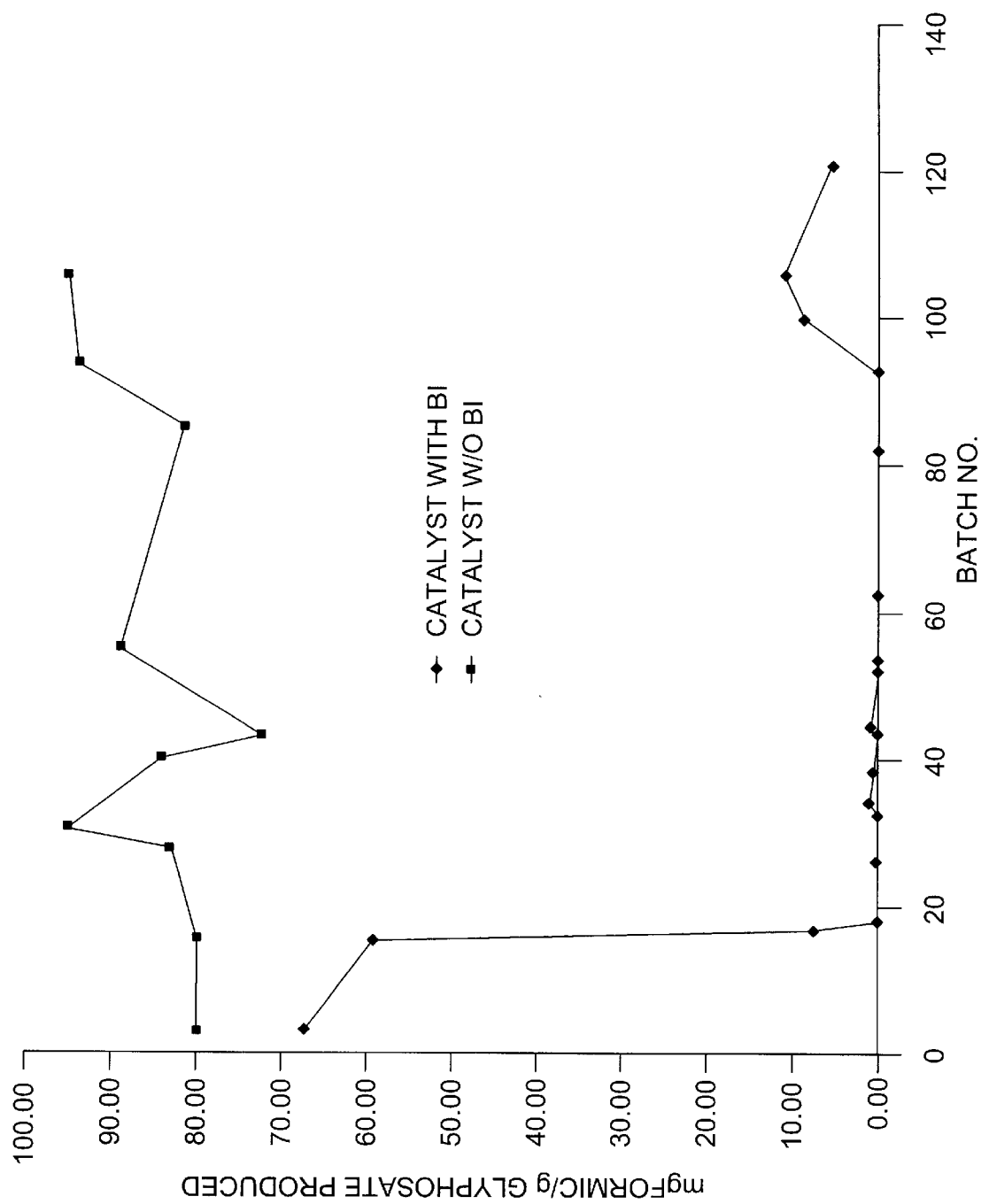
FIG. 9 shows the effect on the formic acid byproduct concentration profile over 107 reaction runs caused by a one-time mixing of bismuth oxide with a catalyst containing 5% by weight platinum and 1% by weight tin.
Figure 10:
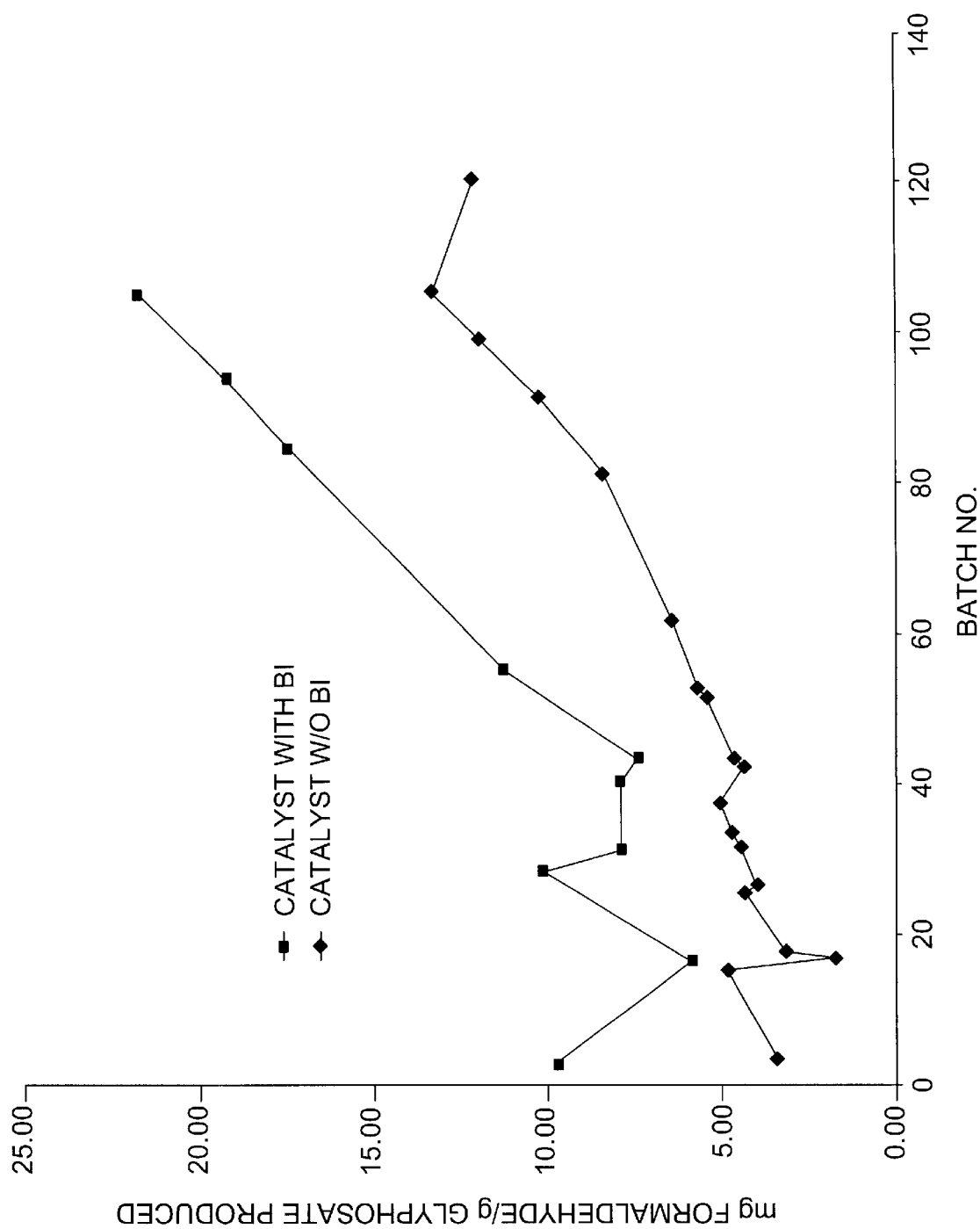
FIG. 10 shows the effect on the formaldehyde byproduct concentration profile over 107 reaction runs caused by a one-time mixing of bismuth oxide with a catalyst containing 5% by weight platinum and 1% by weight tin.
Figure 11:
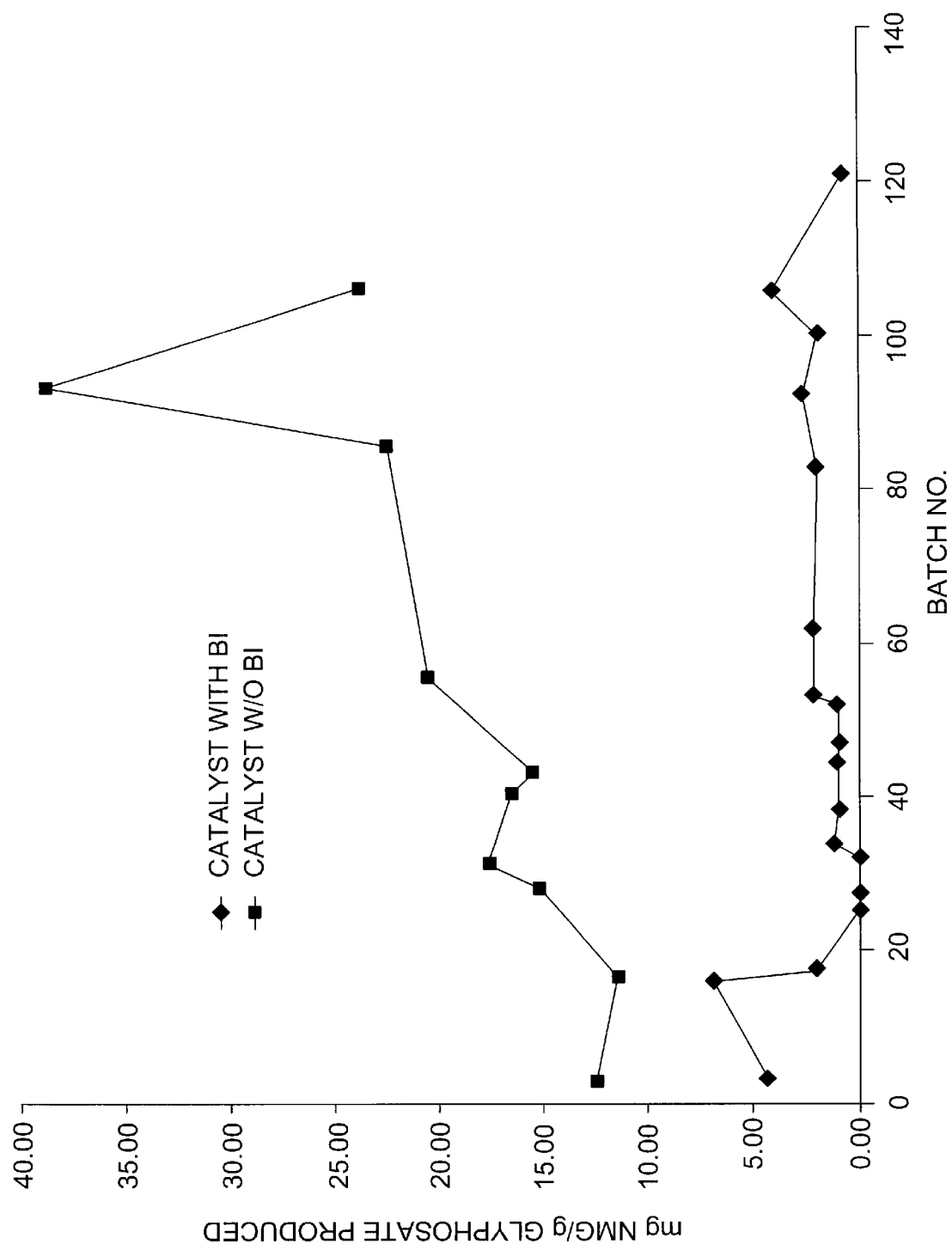
FIG. 11 shows the effect on the NMG byproduct concentration profile over 107 reaction runs caused by a one-time mixing of bismuth oxide with a catalyst containing 5% by weight platinum and 1% by weight tin.

FIG. 9 compares the resulting formic acid concentration profiles, FIG. 10 compares the resulting formaldehyde concentration profiles, and FIG. 11 compares the resulting NMG concentration profiles. Even after 107 runs, the one-time introduction of bismuth into a mixture with the catalyst decreased the formic acid and NMG concentrations by roughly 90%.

Example 21

Evaluation of Cadmium, Nickel, Copper, Molybdenum, Arsenic and Manganese as Supplemental Promoters Fourteen single-run oxidation experiments were conducted to determine the effects of the one-time additions of cadmium oxide, nickel oxide, copper carbonate, molybdenum oxide, arsenic oxide, and manganese oxide salts to a PMIDA oxidation reaction.

Results for the experiments as well as the control experiment are illustrated in Table 19.

TABLE 19

| Exp. No. | 1 | 2 | 3 | 4 | 5 | 6 | 7 | 8 |
|---|---|---|---|---|---|---|---|---|
| Metal Added | CdO (60 ppm) | CdO (120 ppm) | NiO (60 ppm) | NiO (120 ppm) | $CuCO_2.(OH)_2$ (60 ppm) | $CuCO_2.(OH)_2$ (120 ppm) | $MoO_2$ (60 ppm) | $MoO_2$ (120 ppm) |
| Run Time (min) | 42.4 | 57 | 55.4 | 55.1 | 64.3 | 67.2 | 62.9 | 54.4 |
| Glyphosate (%)* | 8.122 | 8.175 | 8.066 | 8.116 | 8.092 | 8.017 | 8.147 | 8.077 |
| PMIDA (%)* | 0.010 | 0.006 | ND | 0.002 | 0.002 | 0.002 | 0.002 | 0.003 |
| $CH_2O$ (%)* | 0.063 | 0.068 | 0.043 | 0.043 | 0.105 | 0.087 | 0.057 | 0.076 |
| $HCO_2H$ (%)* | 0.271 | 0.203 | 0.245 | 0.246 | 0.183 | 0.158 | 0.325 | 0.444 |
| AMPA/MAMPA (%)* | 0.056 | 0.081 | 0.046 | 0.046 | 0.070 | 0.148 | 0.051 | 0.054 |
| NMG (%)* | 0.025 | 0.014 | 0.018 | 0.019 | 0.024 | 0.004 | 0.016 | 0.020 |

| Run No. | 9 | 10 | 11 | 12 | 13 | 14 | Control |
|---|---|---|---|---|---|---|---|
| Metal Added | $As_2O_3$ (60 ppm) | $As_2O_3$ (120 ppm) | $Mn_2O_3$ (60 ppm) | $Mn_2O_3$ (120 ppm) | $As_2O_5.3H_2O$ (60 ppm) | $As_2O_5.3H_2O$ (120 ppm) | |
| Run Time (min) | 73.5 | 60.5 | 56.9 | 57 | 56.6 | 65.1 | 63 |
| Glyphosate (%)* | 7.889 | 7.878 | 7.668 | 7.644 | 8.274 | 8.409 | 8.198 |
| PMIDA (%)* | 0.101 | 0.396 | 0.002 | ND | 0.003 | 0.000 | 0.003 |
| $CH_2O$ (%)* | 0.562 | 0.851 | 0.076 | 0.104 | 0.045 | 0.048 | 0.041 |
| $HCO_2H$ (%)* | 0.365 | 0.541 | 0.256 | 0.299 | 0.239 | 0.208 | 0.271 |
| AMPA/MAMPA (%)* | 0.085 | 0.066 | 0.113 | 0.094 | 0.057 | 0.060 | 0.055 |
| NMG (%)* | 0.330 | 0.348 | 0.018 | 0.039 | 0.013 | 0.008 | 0.015 |

*(mass ÷ total reaction mass) × 100%
"ND" means none detected

The experiments were conducted using a catalyst containing 5% by weight platinum and 0.5% by weight iron. Each experiment was carried out in a 1 L reactor (made of stainless steel, Autoclave Engineers) using 2.5 g catalyst (0.5% by weight of the total reaction mass), 60.5 g PMIDA (12.1% by weight of the total reaction mass), 1000 ppm formaldehyde, 5000 ppm formic acid, a total reaction mass of 500 g, a pressure of 110 psig, a temperature of 100° C., and an agitation rate of 900 rpm. The oxygen feed rate for the first 22 minutes was 392 cc/min., and then 125 cc/min until the PMIDA was essentially depleted. In the control experiment, no metal was introduced. In the other experiments, metal was added to the reaction medium as follows:

Experiment 1—0.034 g (60 ppm) of cadmium oxide (CdO) was added; Experiment 2—0.069 g (120 ppm) of cadmium oxide (Cdo) was added; Experiment 3—0.038 g (60 ppm) of nickel(ous) oxide (NiO) was added; Experiment 4— 0.076 g (120 ppm) of nickel(ous) oxide (NiO) was added; Experiment 5—0.052 g (60 ppm) of copper (II) carbonate $(CuCO_2.(OH)_2)$ was added; Experiment 6—0.104 g (120 ppm) of copper (II) carbonate $(CuCO_2.(OH)_2)$ was added; Experiment 7—0.052 g (60 ppm) of molybdenum IV oxide $(MoO_2)$ was added; Experiment 8—0.104 g (120 ppm) of molybdenum IV oxide $(MoO_2)$ was added; Experiment 9—0.040 g (60 ppm) of arsenic (III) oxide $(As_2O_3)$ was added; Experiment 10—0.080 g (120 ppm) of arsenic (III) oxide $(As_2O_3)$ was added; Experiment 11—0.043 g (60 ppm) of manganese (III) oxide was added; Experiment 12—0.086 g (120 ppm) of manganese (III) oxide was added; Experiment 13—0.046 g (60 ppm) of arsenic (V) oxide hydrate $(As_2O_5.3H_2O)$ was added; and Experiment 14—0.092 g (120 ppm) of arsenic (V) oxide hydrate $(As_2O_5.3H_2O)$ was added.

Example 22

Evaluation of Silver, Cerium and Cobalt as Supplemental Promoters

Nine single-run oxidation experiments were conducted to determine the effects of the one-time additions of tellurium, silver oxide, cerium oxide, cobalt oxide and bismuth oxide salts to a PMIDA oxidation reaction.

The experiments were conducted using a catalyst containing 5% by weight platinum and 0.5% by weight iron. Each experiment was carried out in a 300 ml reactor (made of alloy metal, Hastelloy C, Autoclave Engineers) using 0.9 g catalyst (0.5% by weight of the total reaction mass), 21.8 g PMIDA (12.1% by weight of the total reaction mass), 1000 ppm formaldehyde, 5000 ppm formic acid, a total reaction mass of 180 g, a pressure of 90 psig, a temperature of 100° C., and an agitation rate of 900 rpm. The oxygen feed rate for the first 22 minutes was 141 cc/min., and then 45 cc/min until the PMIDA was essentially depleted. In the control experiment, no metal was introduced. In the other experiments, metal was added to the reaction medium as follows:

Experiment 1—0.013 g (60 ppm) of silver oxide (AgO) was added; Experiment 2—0.013 g (60 ppm) of cerium oxide $(CeO_2)$ was added; Experiment 3—0.027 g (120 ppm) of cerium oxide $(CeO_2)$ was added; Experiment 4— 0.015 g (60 ppm) of cobalt oxide $(Co_3O_4)$ was added; Experiment 5—0.030 g (120 ppm) of cobalt oxide $(Co_3O_4)$ was added; Experiment 6—60 ppm of tellurium was added; Experiment 7—120 ppm of tellurium was added; Experiment 8—0.0616 g (60 ppm) of $H_3BO_3$ was added; and Experiment 9—0.1232 g (120 ppm) of $H_3BO_3$ was added.

Results (except for Experiment 1 which was ineffective) are shown in Table 20.

TABLE 20

| Exp. No. | 2 | 3 | 4 | 5 | 6 | 7 | 8 | 9 | Control |
|---|---|---|---|---|---|---|---|---|---|
| Metal Added | $CeO_2$ (60 ppm) | $CeO_2$ (120 ppm) | $Co_3O_4$ (60 ppm) | $Co_3O_4$ (120 ppm) | Te (60 ppm) | Te (120 ppm) | $H_3BO_3$ (60 ppm) | $H_3BO_3$ (120 ppm) | |
| Run Time (min) | 45.7 | 44 | 43.7 | 44.6 | 29.4 | 29.5 | 47.8 | 44.6 | 44.5 |
| Glyphosate (%)* | 6.529 | 8.030 | 8.042 | 8.055 | 7.765 | 7.738 | 7.926 | 7.906 | 8.070 |
| PMIDA (%)* | 0.055 | 0.232 | 0.134 | 0.207 | 0.012 | 0.009 | 0.090 | 0.120 | 0.127 |
| $CH_2O$ (%)* | 0.071 | 0.072 | 0.085 | 0.093 | 0.783 | 0.810 | 0.070 | 0.074 | 0.065 |
| $HCO_2H$ (%)* | 0.409 | 0.432 | 0.422 | 0.438 | 0.039 | 0.040 | 0.261 | 0.314 | 0.334 |
| AMPA/MAMPA (%)* | 0.035 | 0.030 | 0.033 | 0.033 | 0.061 | 0.062 | 0.037 | 0.035 | 0.031 |
| NMG (%)* | 0.031 | 0.028 | 0.032 | 0.034 | 0.050 | 0.053 | 0.024 | 0.026 | 0.031 |

*(mass ÷ total reaction mass) × 100%
"ND" means none detected

Example 23

Evaluation of Titanium as a Supplemental Promoter

Four single-run oxidation experiments were conducted to determine the effects of the one-time addition of titanium oxide salt to a PMIDA oxidation reaction.

The experiments were conducted using a catalyst containing 5% by weight platinum and 0.5% by weight iron. Each experiment was carried out in a 300 ml reactor (made of alloy metal, Hastelloy C, Autoclave Engineers) using 0.9 g catalyst (0.5% by weight of the total reaction mass), 21.8 g PMIDA (12.1% by weight of the total reaction mass), 1000 ppm formaldehyde, 5000 ppm formic acid, a total reaction mass of 180 g, a pressure of 90 psig, a temperature of 100° C., and an agitation rate of 900 rpm. The oxygen feed rate for the first 22 minutes was 141 cc/min., and then 45 cc/min until the PMIDA was essentially depleted. In the control experiment, no metal was introduced. In the other experiments, 0.018 g (60 ppm) of titanium (IV) oxide ($TiO_2$) was added to the reaction medium in Experiment 1 and 0.036 g (120 ppm) of titanium (IV) oxide ($TiO_2$) was added to the reaction medium in Experiment 2. Results for the experiments as well as the control experiment are illustrated in Table 21.

TABLE 21

| Exp. No. | 1 | 2 | Control |
|---|---|---|---|
| Metal Added | $TiO_2$ (60 ppm) | $TiO_2$ (120 ppm) | |
| Run Time (min) | 38.8 | 36.8 | 44.5 |
| Glyphosate (%)* | 7.812 | 7.787 | 8.070 |
| PMIDA (%)* | 0.503 | 0.670 | 0.127 |
| $CH_2O$ (%)* | 0.071 | 0.079 | 0.065 |
| $HCO_2H$ (%)* | 0.463 | 0.513 | 0.334 |
| AMPA/MAMPA (%)* | 0.027 | 0.027 | 0.031 |
| NMG (%)* | 0.023 | 0.026 | 0.031 |

*(mass ÷ total reaction mass) × 100%
"ND" means none detected

Example 24

Evaluation of Vanadium, Gallium, Niobium, Tantalum, Selenium and Antimony as a Supplemental Promoter Thirteen single-run oxidation experiments were conducted to determine the effects of the one-time additions of vanadium oxide, gallium oxide, niobium oxide, tantalum oxide, selenium oxide, and antimony oxide salts to a PMIDA oxidation reaction.

The experiments were conducted using a catalyst containing 5% by weight platinum and 0.5% by weight iron. Each experiment was carried out in a 300 ml reactor (made of alloy metal, Hastelloy C, Autoclave Engineers) using 0.9 g catalyst (0.5% by weight of the total reaction mass), 21.8 g PMIDA (12.1% by weight of the total reaction mass), 1000 ppm formaldehyde, 5000 ppm formic acid, a total reaction mass of 180 g, a pressure of 90 psig, a temperature of 100° C., and an agitation rate of 900 rpm. The oxygen feed rate for the first 22 minutes was 141 cc/min., and then 45 cc/min until the PMIDA was essentially depleted. In the control experiment, no metal was introduced. In the other experiments, metal was added to the reaction medium as follows:

Experiment 1—0.019 g (60 ppm) of vanadium oxide ($V_2O_5$) was added; Experiment 2—0.039 g (120 ppm) of vanadium oxide ($V_2O_5$) was added; Experiment 3—0.015 g (60 ppm) of gallium oxide ($Ga_2O_3$) was added; Experiment 4—0.029 g (120 ppm) of gallium oxide ($Ga_2O_3$) was added; Experiment 5—0.015 g (60 ppm) of niobium oxide ($Nb_2O_5$) was added; Experiment 6—0.031 g (120 ppm) of niobium oxide ($Nb_2O_5$) was added; Experiment 7—0.013 g (60 ppm) of tantalum oxide($Ta_2O_5$) was added; Experiment 8—0.026 g (120 ppm) of tantalum oxide ($Ta_2O_5$) was added; Experiment 9—0.015 g (60 ppm) of selenium oxide ($SeO_2$) was added; Experiment 10—0.030 g (120 ppm) of selenium oxide ($SeO_2$) was added; Experiment 11—0.013 g (60 ppm) of antimony oxide ($Sb_2O_3$) was added; and Experiment 12—0.026 g (120 ppm) of antimony oxide ($Sb_2O_3$) was added.

Results for the experiments as well as the control experiment are illustrated in Table 22.

TABLE 22

| Exp. No. | 1 | 2 | 3 | 4 | 5 | 6 | 7 | 8 |
|---|---|---|---|---|---|---|---|---|
| Metal Added | $V_2O_5$ (60 ppm) | $V_2O_5$ (120 ppm) | $Ga_2O_3$ (60 ppm) | $Ga_2O_3$ (120 ppm) | $Nb_2O_5$ (60 ppm) | $Nb_2O_5$ (120 ppm) | $Ta_2O_5$ (60 ppm) | $Ta_2O_5$ (120 ppm) |

TABLE 22-continued

| Run Time (min) | 41.1 | 35.9 | 39.3 | 41.5 | 43.8 | 42.8 | 42.6 | 41.0 |
|---|---|---|---|---|---|---|---|---|
| Glyphosate (%)* | 7.200 | 6.981 | 8.082 | 8.127 | 8.170 | 8.252 | 8.116 | 7.989 |
| PMIDA (%)* | 0.086 | 0.264 | 0.326 | 0.302 | 0.221 | 0.191 | 0.303 | 0.380 |
| $CH_2O$ (%)* | 0.153 | 0.172 | 0.080 | 0.076 | 0.074 | 0.068 | 0.079 | 0.084 |
| $HCO_2H$ (%)* | 0.552 | 0.579 | 0.483 | 0.448 | 0.421 | 0.411 | 0.438 | 0.461 |
| AMPA/MAMPA (%)* | 0.214 | 0.252 | 0.028 | 0.030 | 0.032 | 0.030 | 0.029 | 0.029 |
| NMG (%)* | 0.080 | 0.117 | 0.033 | 0.030 | 0.032 | 0.032 | 0.034 | 0.036 |

| Exp. No. | 9 | 10 | 11 | 12 | Control |
|---|---|---|---|---|---|
| Metal Added | $SeO_2$ (60 ppm) | $SeO_2$ (120 ppm) | $Sb_2O_3$ (60 ppm) | $Sb_2O_3$ (120 ppm) | |
| Run Time (min) | 84 | 61.4 | 58.1 | 61.2 | 43.0 |
| Glyphosate (%)* | 3.705 | 2.848 | 8.096 | 8.191 | 8.076 |
| PMIDA (%)* | lg. peak | lg. peak | 0.020 | 0.201 | 0.251 |
| $CH_2O$ (%)* | 0.268 | 0.300 | 0.011 | 0.016 | 0.083 |
| $HCO_2H$ (%)* | 0.434 | 0.523 | 0.068 | 0.039 | 0.441 |
| AMPA/MAMPA (%)* | 0.035 | 0.022 | 0.054 | 0.054 | 0.031 |
| NMG (%)* | 0.032 | 0.025 | 0.003 | 0.007 | 0.030 |

*(mass ÷ total reaction mass) × 100%
"ND" means none detected

Example 25

Evaluation of Lanthanum, Rhenium and Ruthenium as a Supplemental Promoter

Six single-run oxidation experiments were conducted to determine the effects of the one-time additions of lanthanum oxide, rhenium oxide and ruthenium oxide salts to a PMIDA oxidation reaction.

The experiments were conducted using a catalyst containing 5% by weight platinum and 0.5% by weight iron. Each experiment was carried out in a 300 ml reactor (made of alloy metal, Hastelloy C, Autoclave Engineers) using 0.9 g catalyst (0.5% by weight of the total reaction mass), 21.8 g PMIDA (12.1% by weight of the total reaction mass), 1000 ppm formaldehyde, 5000 ppm formic acid, a total reaction mass of 180 g, a pressure of 90 psig, a temperature of 100° C., and an agitation rate of 900 rpm. The oxygen feed rate for the first 22 minutes was 141 cc/min., and then 45 cc/min until the PMIDA was essentially depleted. In the control experiment, no metal was introduced. In the other experiments, metal was added to the reaction medium as follows:

Experiment 1—0.013 g (60 ppm) of lanthanum oxide ($La_2O_3$) was added; Experiment 2—0.025 g (120 ppm) of lanthanum oxide ($La_2O_3$) was added; Experiment 3—0.013 g (60 ppm) of rhenium oxide ($ReO_2$) was added; Experiment 4—0.025 g (120 ppm) of rhenium oxide ($ReO_2$) was added; Experiment 5—0.014 g (60 ppm) of ruthenium oxide ($RuO_2$) was added; and Experiment 6—0.028 g (120 ppm) of ruthenium oxide ($RuO_2$) was added. Results are shown in Table 23.

TABLE 23

| Exp. No. | 1 | 2 | 3 | 4 | 5 | 6 | Control |
|---|---|---|---|---|---|---|---|
| Metal Added | $La_2O_3$ (60 ppm) | $La_2O_3$ (120 ppm) | $ReO_2$ (60 ppm) | $ReO_2$ (120 ppm) | $RuO_2$ (60 ppm) | $RuO_2$ (120 ppm) | |
| Run Time (min) | 58.2 | 44 | 43.7 | 48.7 | 43.5 | 44.1 | 44.5 |
| Glyphosate (%)* | 7.960 | 8.041 | 8.120 | 7.921 | 7.939 | 7.978 | 8.070 |
| PMIDA (%)* | 0.235 | 0.208 | 0.268 | 0.245 | 0.193 | 0.193 | 0.127 |
| $CH_2O$ (%)* | 0.082 | 0.089 | 0.073 | 0.061 | 0.070 | 0.063 | 0.065 |
| $HCO_2H$ (%)* | 0.356 | 0.350 | 0.391 | 0.376 | 0.417 | 0.395 | 0.334 |
| AMPA/MAMPA (%)* | 0.040 | 0.041 | 0.035 | 0.036 | 0.034 | 0.036 | 0.031 |
| NMG (%)* | 0.034 | 0.037 | 0.028 | 0.028 | 0.029 | 0.027 | 0.031 |

*(mass ÷ total reaction mass) × 100%
"ND" means none detected

Example 26

Effect of Two Supplemental Promoters

A sixteen-run oxidation experiment was conducted to determine the effects of the addition two supplemental promoters (bismuth followed by tellurium) for use in a PMIDA oxidation reaction.

The experiment was conducted using a catalyst containing 5% by weight platinum and 0.5% by weight iron. The experiments were carried out in a 1L reactor (made of stainless steel, Autoclave Engineers) using 3.75 g catalyst (0.75% by weight of the total reaction mass), 60.5 g PMIDA (12.1% by weight of the total reaction mass), 500 ppm formaldehyde, 500 ppm formic acid, a total reaction mass of 500 g, a pressure of 135 psig, a temperature of 100° C., and an agitation rate of 900 rpm. The oxygen feed rate for the first 22 minutes was 468 cc/min., and then 125 cc/min until the PMIDA was essentially depleted. In the control experiment, no metals were introduced as a supplemental promoter.

Figure 12:
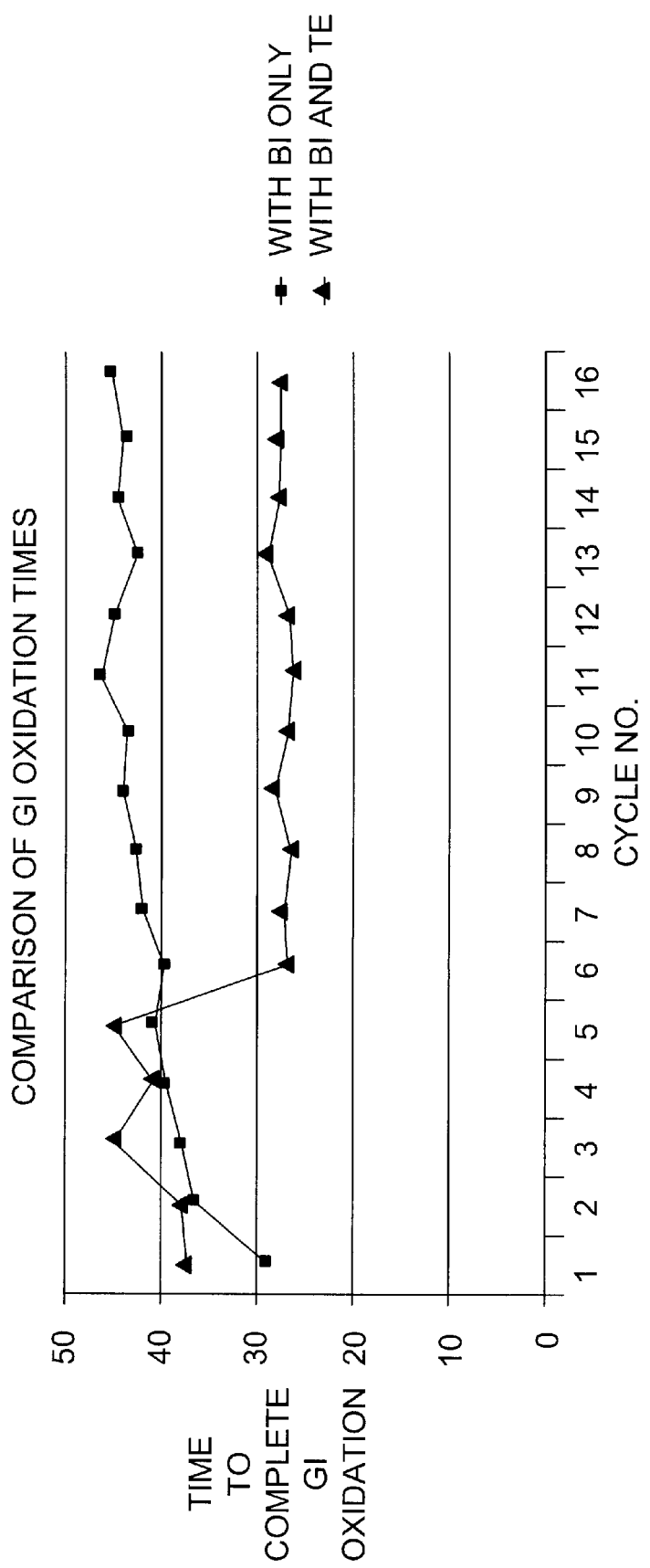
FIG. 12 shows the effect of two supplemental promoters by a comparison of N-(phosphonomethyl) iminodiacetic acid oxidation rates when bismuth versus bismuth and tellurium are used as supplemental promoters.
Figure 13:
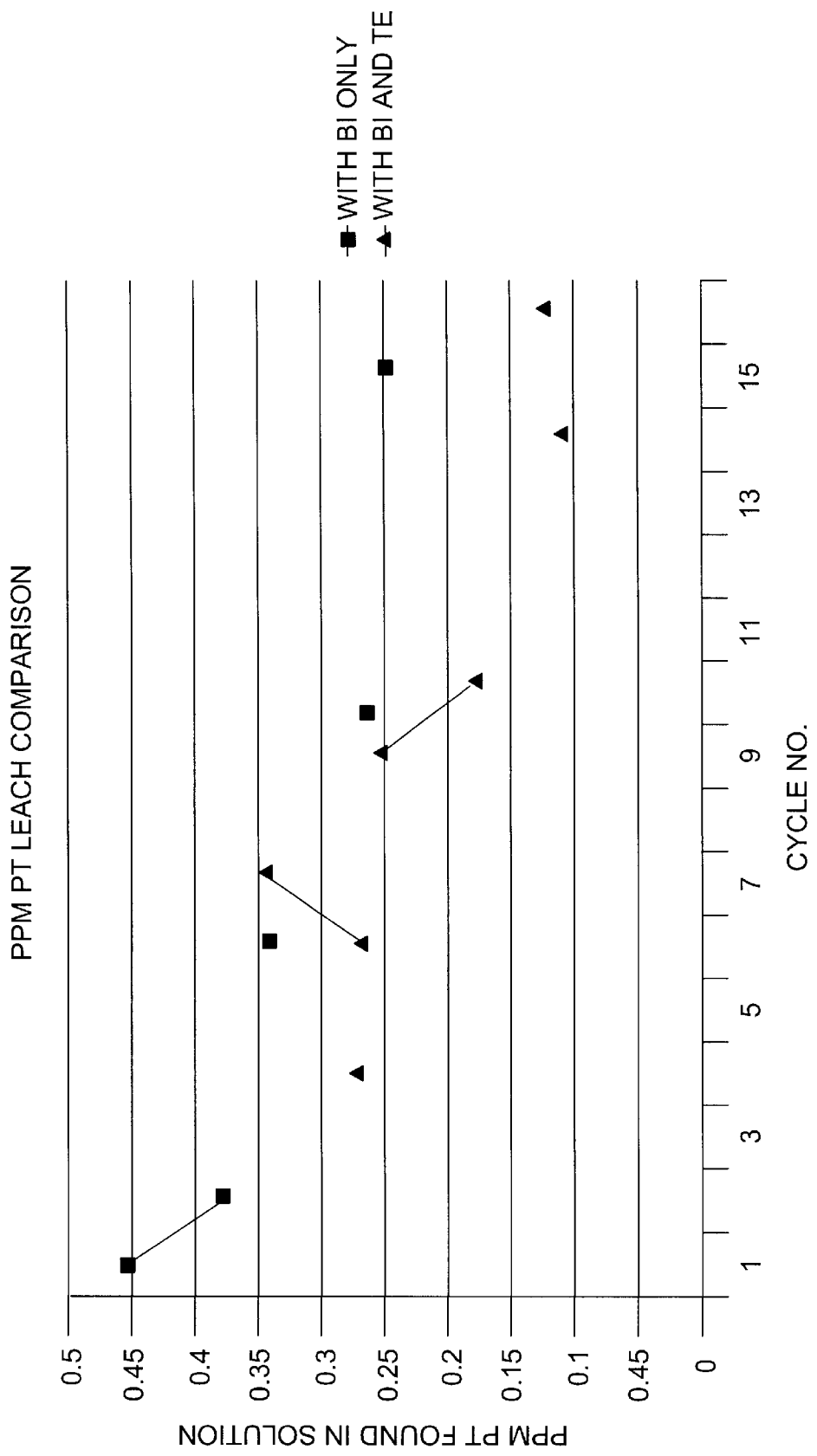
FIG. 13 shows the effect of using two supplemental promoters by a comparison of the amount of platinum leached from the catalyst when bismuth versus bismuth and tellurium are used as supplemental promoters.
Figure 14:
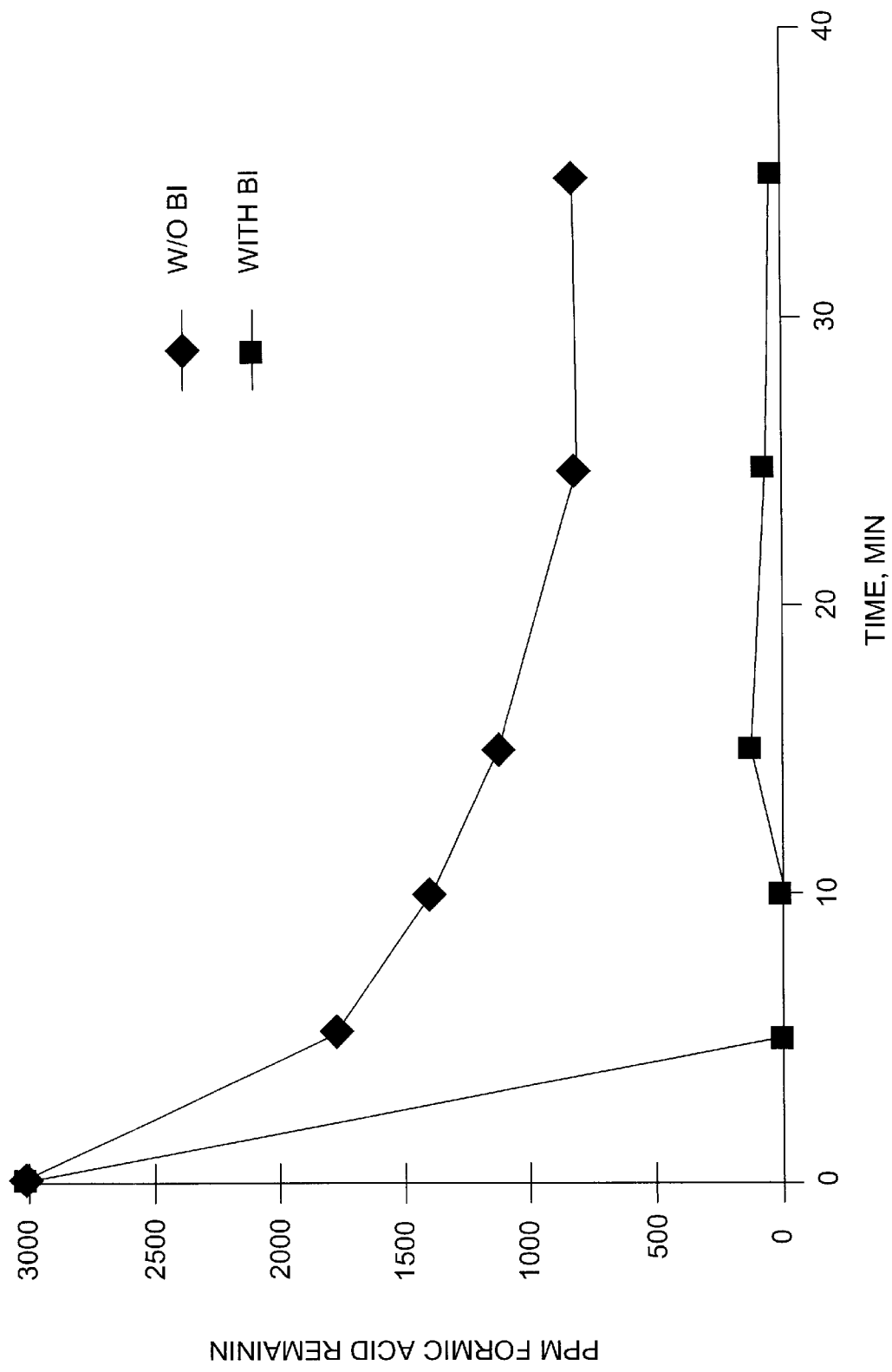
FIG. 14 shows the effect of a supplemental promoter in oxidizing an aqueous stream of formic acid and formaldehyde by a comparison of formic acid oxidation activity when bismuth is used as a supplemental promoter.
Figure 15:
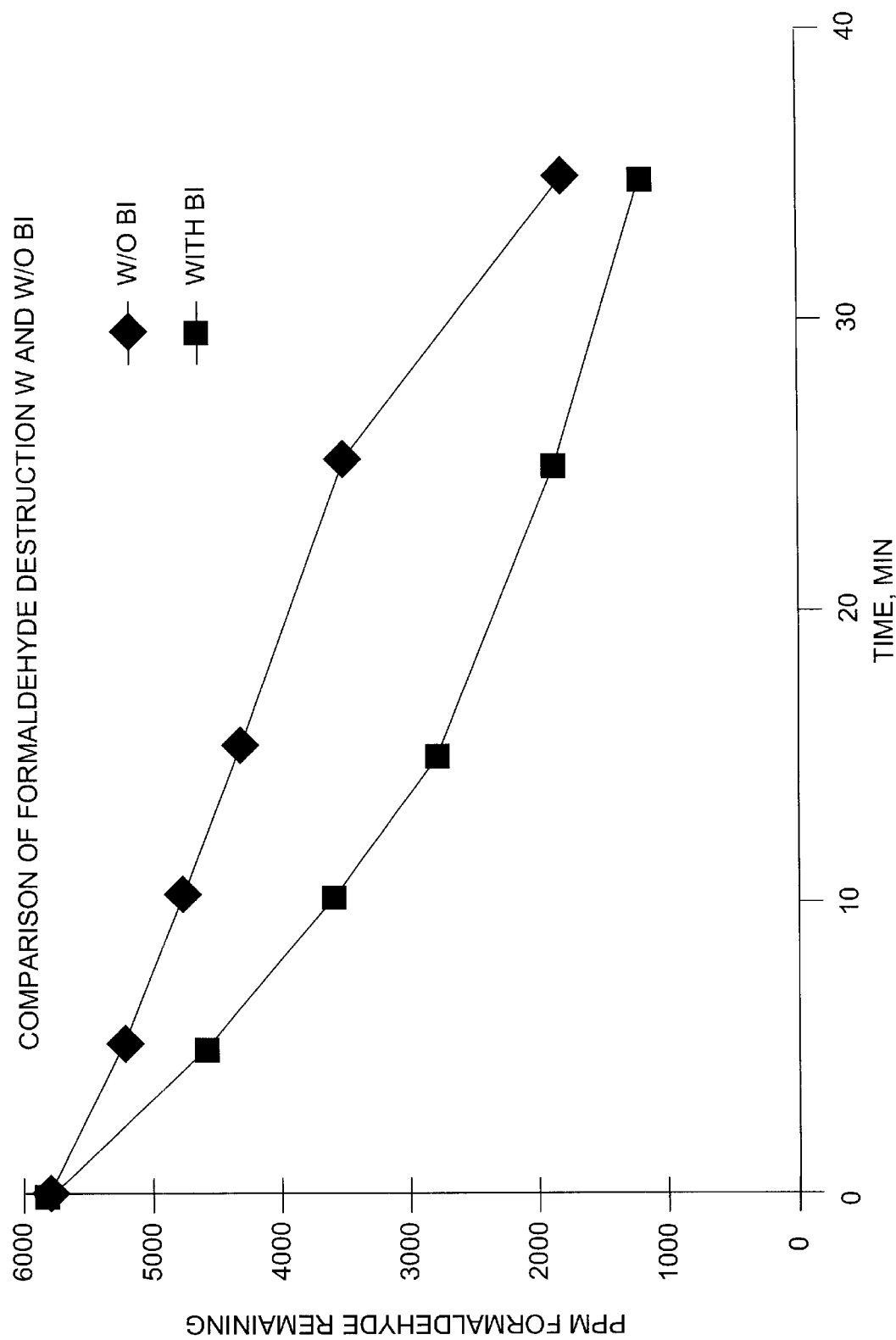
FIG. 15 shows the effect of a supplemental promoter in oxidizing an aqueous stream of formic acid and formaldehyde by a comparison of formaldehyde oxidation activity when bismuth is used as a supplemental promoter.

In adding the supplemental promoter, 0.034 g (60 ppm) of $Bi_2O_3$ was charged to the first reaction. After the 6th reaction run, 0.0375 g (60 ppm) of $Te(IV)O_2$ was charged to the reactor and the remaining ten experiments were evaluated. Oxidation results for the experiments are illustrated in Table 24. As shown in FIGS. 12 and 13, the addition of the second supplemental promoter, Te, reduced the time to complete the oxidation of PMIDA and reduced the amount of noble metal found in solution. Thus, the use of a second supplemental promoter is beneficial to increase the rate of PMIDA oxidation and to reduce the amount of noble metal leaching from the catalyst.

TABLE 25

Evaluation Method

| Task | Gas | Temperature | Hold time |
|---|---|---|---|
| Flow | He | RT to 150 @ 5° C./min | 30 |
| Flow | He | 120 to 30 @ 20° C./min | 5 |
| Evacuation | | 30° C. | 15 |
| Leak Test | | 30° C. | |
| Evacuation | | 30° C. | 15 |
| Flow | H2 | 30 to 150 @ 10° C./min | 15 |
| Evacuation | | 150° C. | 10 |
| Evacuation | | 150 to 30 @ 20° C./min | 30 |
| Leak Test | | 30° C. | |
| Evacuation | | 30° C. | 30 |
| Analysis | CO | 30° C. | |

TABLE 24

| Exp. No. | Run Time (min) | Glyphosate (%)* | PMIDA (%)* | $CH_2O$ (%)* | $HCO_2H$ (%)* | AMPA/MAMPA (%)* | NMG (%)* |
|---|---|---|---|---|---|---|---|
| 1 | 37.4 | 7.776 | 0.018 | 0.016 | 0.039 | 0.127 | 0.000 |
| 2 | 37.6 | 8.452 | 0.014 | 0.015 | 0.037 | 0.104 | 0.000 |
| 3 | 45 | 8.382 | 0.008 | 0.016 | 0.038 | 0.122 | 0.000 |
| 4 | 40.4 | 8.460 | 0.006 | 0.019 | 0.042 | 0.123 | 0.000 |
| 5 | 44.8 | 8.399 | 0.007 | 0.015 | 0.040 | 0.088 | 0.000 |
| 6 | 26.7 | 8.459 | 0.023 | 0.533 | 0.131 | 0.058 | 0.073 |
| 7 | 27.2 | 8.326 | 0.000 | 0.445 | 0.070 | 0.068 | 0.039 |
| 8 | 26 | 8.258 | 0.000 | 0.386 | 0.057 | 0.071 | 0.031 |
| 9 | 27.8 | 8.274 | 0.014 | 0.599 | 0.059 | 0.057 | 0.037 |
| 10 | 26.6 | 8.294 | 0.000 | 0.435 | 0.054 | 0.069 | 0.029 |
| 11 | 26.3 | 8.224 | 0.015 | 0.408 | 0.059 | 0.062 | 0.036 |
| 12 | 26.4 | 8.270 | 0.013 | 0.389 | 0.055 | 0.066 | 0.033 |
| 13 | 28.6 | 8.279 | 0.023 | 0.462 | 0.056 | 0.049 | 0.043 |
| 14 | 27.5 | 8.314 | 0.015 | 0.412 | 0.053 | 0.061 | 0.037 |
| 15 | 27.8 | 8.243 | 0.020 | 0.454 | 0.052 | 0.060 | 0.042 |
| 16 | 27.4 | 8.294 | 0.016 | 0.430 | 0.055 | 0.063 | 0.042 |

*(mass ÷ total reaction mass) × 100%

Example 27

Comparison of CO Chemisorption for Bi-doped Catalyst

Several samples of the 5% Pt/0.5% Fe on carbon catalyst used in the above examples were studied using CO chemisorption measurements to determine the number of active sites. The catalyst samples analyzed were taken from PMIDA oxidation reactions. The catalyst samples had been previously used in from 6 to 35 previous reaction cycles with the addition of a bismuth supplemental promoter. A sample of the same catalyst run 6 times without the addition of Bi was used as a reference sample.

A Micromeritics ASAP2010C static chemisorption instrument was used to collect the volume adsorbed versus pressure data used to determine the μmol CO adsorbed and the dispersion. The catalyst samples were weighed using a Mettler AT261 analytical balance. Approximately 0.2500 gm of sample was used in the chemisorption experiments. Standard 10 mm I.D. flow through sample tubes held the sample and quartz wool plugs aided in restricting sample movement. The samples were degassed under vacuum overnight at 150° C. before analysis. Ultra high purity nitrogen gas was used as the backfill gas. Analysis of these samples was performed using the ASAP 2010 unit 2 gas chemisorption instrument from Micromeritics.

TABLE 26

5% Pt/0.5% Fe Chemisorption Results

| Sample ID | CO chemisorption (umol CO/gm cat) | Dispersion (%) |
|---|---|---|
| 6 runs w/o Bi | 19.6 | 7.6 |
| 6 runs w/Bi | 7.6 | 3.0 |
| 20 runs w/Bi | 11.8 | 4.6 |
| 35 runs w/Bi | 7.5 | 2.9 |

The CO chemisorption results showed a decrease in the amount of adsorption in the samples treated with Bi when compared to a sample which had not been treated with Bi. The Bi treated samples had a CO chemisorption as low as 7.5 μmol CO/g catalyst. The untreated sample had a CO chemisorption of 19.6 μmol CO/g catalyst.

Example 28

Effect of The Simultaneous Addition of Two Supplemental Promoters

Seven single-run oxidation experiments were conducted to determine the effects of the simultaneous addition of two supplemental promoters (bismuth and tellurium) for use in a PMIDA oxidation reaction.

The experiments were conducted using a catalyst containing 5% by weight platinum and 0.65% by weight iron.

The experiments were carried out in a 1 L reactor (made of stainless steel, Autoclave Engineers) using 2.5 g catalyst (0.5% by weight of the total reaction mass), 60.5 g PMIDA (12.1% by weight of the total reaction mass), 1000 ppm formaldehyde, 5000 ppm formic acid, a total reaction mass of 500 g, a pressure of 110 psig, a temperature of 100° C., and an agitation rate of 900 rpm. The oxygen feed rate for the first 22 minutes was 392 cc/min., and then 125 cc/min until the PMIDA was essentially depleted.

The experiments included adding supplemental promoter to the reaction medium as follows:

1. No supplemental promoter was added in Experiment 1 as to establish a baseline with the above catalyst;
2. 0.0075 g (12 ppm) tellurium dioxide was added in Experiment 2;
3. 0.0075 g (12 ppm) tellurium dioxide and 0.0067 g (12 ppm) bismuth oxide were added in Experiment 3;
4. 0.015 g (24 ppm) tellurium dioxide was added in Experiment 4;
5. 0.015 g (24 ppm) tellurium dioxide and 0.0067 g (12 ppm) bismuth oxide were added in Experiment 5;
6. 0.030 g (48 ppm) tellurium dioxide was added in Experiment 6;
7. 0.030 g (48 ppm) tellurium dioxide and 0.0067 g (12 ppm) bismuth oxide were added to Experiment 7.

Results are shown in Table 27.

TABLE 27

| Exp. No. | Run Time (min) | Glyphosate (%)* | PMIDA (%)* | CH$_2$O (%)* | HCO$_2$H (%)* | AMPA/MAMPA (%)* | NMG (%)* |
|---|---|---|---|---|---|---|---|
| 1 | 38.3 | 8.030 | 0.014 | 0.043 | 0.437 | 0.042 | 0.031 |
| 2 | 64.9 | 8.270 | 0.014 | 0.041 | ND | 0.065 | 0.005 |
| 3 | 64.3 | 7.920 | 0.017 | 0.030 | ND | 0.067 | ND |
| 4 | 42.7 | 8.130 | 0.021 | 0.465 | 0.057 | 0.084 | 0.055 |
| 5 | 35.3 | 7.790 | 0.008 | 0.504 | 0.052 | 0.072 | 0.039 |
| 6 | 37.4 | 8.160 | 0.011 | 0.553 | 0.073 | 0.097 | 0.073 |
| 7 | 30 | 8.140 | 0.029 | 0.560 | 0.065 | 0.127 | 0.047 |

*(mass ÷ total reaction mass) × 100%
ND = "not detected"

Example 29

Effect of a Supplemental Promoter on the Catalytic Oxidation of Formic Acid and Formaldehyde Two single-run oxidation experiments were conducted to determine the effects of a supplemental promoter for use in the catalytic oxidation of an aqueous stream of formic acid and formaldehyde.

The experiment was conducted using a catalyst containing 5% by weight platinum and 0.5% by weight iron. The experiments were carried out in a 300 ml reactor (made of alloyed metal, Hastelloy C, Autoclave Engineers) using 0.28 g catalyst, 5800 ppm formaldehyde, 3800 ppm formic acid, a total reaction mass of 180 g, a pressure of 100 psig, a temperature of 100° C., and an agitation rate of 900 rpm. The oxygen feed rate was 100 cc/min.

The experiment consisted of three single-run oxidation experiments run for 35 minutes each. Samples were collected and analyzed for In the first experiment, the aqueous formic acid and formaldehyde were catalytically oxidized with no supplemental promoter added, so as to establish a baseline. In the second experiment, 30 ppm of bismuth was added as a supplemental promoter and, in the third experiment, 30 ppm of tellurium was added as a supplemental promoter. Comparisons of the formic acid and formaldehyde destruction from the addition of bismuth and tellurium are shown in FIGS. 14, 15, 16 and 17.

The present invention is not limited to the above embodiments and can be variously modified. The above description of the preferred embodiment is intended only to acquaint others skilled in the art with the invention, its principles, and its practical application so that others skilled in the art may adapt and apply the invention in its numerous forms, as may be best suited to the requirements of a particular use.

With reference to the use of the word(s) "comprise" or "comprises" or "comprising" in this entire specification (including the claims below), Applicants note that unless the context requires otherwise, those words are used on the basis and clear understanding that they are to be interpreted inclusively, rather than exclusively, and that Applicants intend each of those words to be so interpreted in construing this entire specification.

We claim:

1. A process for the preparation of N-(phosphonomethyl) glycine or a salt thereof, the process comprising:

oxidizing N-(phosphonomethyl) iminodiacetic acid in an aqueous reaction medium in the presence of an oxidation catalyst comprising a noble metal on a carbon support, thereby producing an aqueous reaction mixture comprising N-(phosphonomethyl) glycine, formic acid or formaldehyde;

separating oxidation catalyst from said reaction mixture to produce a filtrate comprising N-(phosphonomethyl) glycine, formic acid or formaldehyde;

evaporating water, formic acid or formaldehyde from said filtrate to produce an overhead vapor stream;

condensing water, formic acid or formaldehyde from said overhead vapor stream and forming an aqueous treatment mixture containing water, formic acid or formaldehyde;

contacting said aqueous treatment mixture with an oxidizing agent in the presence of a noble metal catalyst on a carbon support and a promoter metal comprising a metal effective to promote oxidation of formic acid or formaldehyde, thereby forming a treated condensate by oxidizing formic acid or formaldehyde contained in said treatment mixture; and recycling treated condensate incorporating it into an aqueous medium for N-(phosphonomethyl) iminodiacetic acid in the further oxidation thereof to N-(phosphonomethyl) glycine or a salt thereof.

2. A process as set forth in claim 1 wherein a supplemental promoter metal is present in the aqueous reaction medium in which N-(phosphonomethyl) iminodiacetic acid or a salt thereof is oxidized to N-(phosphonomethyl) glycine or a salt thereof.

3. A process as set forth in claim 2 wherein said supplemental promoter metal comprises bismuth or tellurium.

4. A process as set forth in claim 1 wherein the oxidation of formic acid or formaldehyde contained in said condensate is conducted in the presence of a supplemental promoter metal.

5. A process as set forth in claim 4 wherein said supplemental promote metal comprises bismuth or tellurium.

6. A process for making N-(phosphonomethyl) glycine or a salt thereof, the process comprising:

mixing a supplemental promoter metal with an oxidation catalyst in a liquid medium to form a promoted catalyst mixture comprising said oxidation catalyst, said supplemental promoter metal and the liquid medium, the oxidation catalyst comprising a noble metal on a carbon support; and oxidizing N-(phosphonomethyl) iminodiacetic acid or a salt thereof in an aqueous reaction medium in the presence of the oxidation catalyst, the aqueous reaction medium comprising said promoted catalyst mixture, thereby producing an aqueous reaction mixture comprising N-(phosphonomethyl) glycine or a salt thereof.

7. A process as set forth in claim 6 wherein the supplemental promoter metal and the oxidation catalyst are mixed in the reaction medium.

8. A process as set forth in claim 6 wherein said promoted catalyst mixture is prepared separately from the reaction medium.

9. A process as set forth in claim 8 wherein said promoted catalyst mixture is prepared in a catalyst holding tank.

10. A process as set forth in claim 8 wherein said promoted catalyst mixture is prepared in a catalyst recycle tank.

11. A process as set forth in claim 6 wherein the mass ratio of the supplemental promoter metal to the catalyst is at least about 1:15,000.

12. A process as set forth in claim 6, wherein the supplemental promoter metal increases the selectivity of the catalyst for making N-(phosphonomethyl) glycine or the salt thereof from N-(phosphonomethyl) iminodiacetic acid or the salt thereof.

13. A process as set forth in claim 6, wherein the supplemental promoter metal reduces noble metal leaching from the carbon support.

14. A process as set forth in claim 6, wherein the supplemental promoter metal increases the activity of the catalyst for oxidizing N-(phosphonomethyl) iminodiacetic acid or the salt thereof.

15. A process as set forth in claim 6, wherein said N-(phosphonomethyl) iminodiacetic acid or a salt thereof is oxidized at a temperature of from about 60° to about 150° C., said N-(phosphonomethyl) iminodiacetic acid or a salt thereof having a concentration of about 12 to about 18% as measured by weight of the total reaction mass.

16. A process as set forth in claim 15, wherein said N-(phosphonomethyl) iminodiacetic acid or a salt thereof is oxidized at a temperature of from about 100° to about 130° C.

17. A process as set forth in claim 6, wherein the supplemental promoter metal comprises bismuth, lead, germanium, tellurium, titanium, copper or nickel.

18. A process as set forth in claim 17, wherein the supplemental promoter metal comprises bismuth or tellurium.

19. A process as set forth in claim 18, wherein the supplemental promoter metal comprises bismuth.

20. A process as set forth in claim 18, wherein the supplemental promoter metal comprises tellurium.

21. A process as set forth in claim 17, wherein said promoted catalyst mixture is formed by mixing two supplemental promoter metals with the oxidation catalyst.

22. A process as set forth in claim 21, wherein the supplemental promoter metals comprise bismuth, titanium or tellurium.

23. A process as set forth in claim 22, wherein the supplemental promoter metals comprise bismuth and tellurium.

24. A process as set forth in claim 6 further comprising contacting the aqueous reaction mixture with a second supplemental promoter metal after partial conversion of the N-(phosphonomethyl) iminodiacetic acid or a salt thereof to an oxidation product thereof.

25. A process as set forth in claim 6, wherein the supplemental promoter metals comprise bismuth, titanium or tellurium.

26. A process as set forth in claim 24, wherein the first supplemental promoter metal comprises bismuth and the second supplemental promoter metal comprises tellurium.

27. A process as set forth in claim 6, wherein the oxidation catalyst mixed with the supplemental promoter metal in the liquid medium is used.

\* \* \* \* \*